United States Patent
Batt et al.

(10) Patent No.: US 7,381,738 B2
(45) Date of Patent: Jun. 3, 2008

(54) SUBSTITUTED BICYCLOALKYLAMINE DERIVATIVES AS MODULATORS OF CHEMOKINE RECEPTOR ACTIVITY

(75) Inventors: Douglas G. Batt, Wilmington, DE (US); Percy H. Carter, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 312 days.

(21) Appl. No.: 11/060,250

(22) Filed: Feb. 17, 2005

(65) Prior Publication Data

US 2005/0227960 A1    Oct. 13, 2005

Related U.S. Application Data

(60) Provisional application No. 60/545,921, filed on Feb. 19, 2004.

(51) Int. Cl.
- A61K 31/403 (2006.01)
- A61K 31/5377 (2006.01)
- A61K 31/4709 (2006.01)
- C07D 209/52 (2006.01)
- C07D 413/12 (2006.01)
- C07D 215/42 (2006.01)
- C07D 215/46 (2006.01)

(52) U.S. Cl. ............ 514/412; 514/235.2; 514/314; 544/143; 546/169; 548/515

(58) Field of Classification Search ............ 514/235.2, 514/412, 314; 544/143; 546/169; 548/515
See application file for complete search history.

(56) References Cited

U.S. PATENT DOCUMENTS

| | | | |
|---|---|---|---|
| 5,869,496 A | 2/1999 | Hale et al. | |
| 6,011,052 A | 1/2000 | Padia et al. | |
| 6,013,644 A | 1/2000 | Mills et al. | |
| 2005/0054626 A1* | 3/2005 | Carter et al. | 514/210.01 |
| 2005/0192276 A1* | 9/2005 | Batt et al. | 514/232.5 |
| 2005/0197325 A1* | 9/2005 | Batt et al. | 514/210.01 |
| 2005/0197373 A1* | 9/2005 | Batt et al. | 514/381 |

FOREIGN PATENT DOCUMENTS

| | | |
|---|---|---|
| WO | WO 94/29309 | 12/1994 |
| WO | WO 97/44329 | 11/1997 |
| WO | WO 98/06703 | 2/1998 |
| WO | WO 99/07351 | 2/1999 |
| WO | WO 99/07678 | 2/1999 |
| WO | WO 99/25686 | 5/1999 |
| WO | WO 99/40913 | 8/1999 |
| WO | WO 99/40914 | 8/1999 |
| WO | WO 02/50019 A2 | 6/2000 |
| WO | WO 00/46196 | 8/2000 |
| WO | WO 00/69815 | 11/2000 |
| WO | WO 00/69820 | 11/2000 |
| WO | WO02/060859 A2 | 8/2002 |
| WO | WO02/070523 A1 | 9/2002 |
| WO | WO 02/081449 A1 | 10/2002 |
| WO | WO03/091245 A1 | 11/2003 |
| WO | WO03/092568 A1 | 11/2003 |
| WO | WO03/093231 A2 | 11/2003 |
| WO | WO03/099773 A1 | 12/2003 |
| WO | WO03/101970 A1 | 12/2003 |
| WO | WO03/105853 A1 | 12/2003 |
| WO | WO 03101970 A1 * | 12/2003 |
| WO | WO2004/007472 A1 | 1/2004 |
| WO | WO2004/009550 A1 | 1/2004 |
| WO | WO2004/009588 A1 | 1/2004 |
| WO | WO 2004/010942 A2 | 2/2004 |
| WO | WO2004/010943 A2 | 2/2004 |
| WO | WO 2004/011418 A1 | 2/2004 |
| WO | WO 2004/011427 A2 | 2/2004 |
| WO | WO 2004/011443 A1 | 2/2004 |
| WO | WO2004/012671 A2 | 2/2004 |

OTHER PUBLICATIONS

Quinones et al. J. Mol. Med. 2005, 83, 672-681.*
Feria et al. Expert Opin. Ther. Patents 2006, 16(1), 49-57.*
Forbes, Ian T. et al., "CCR2B Receptor Antagonists:Conversion of a Weak HTS Hit to a Potent Lead Compound", Bioorg. Med. Chem. Lett. vol. 10, pp. 1803-1806 (2000).
Mirzadegan, Tara et al., "Indentification of the Binding Site for a Novel Class of CCR2b Chemokine Receptor Antagonists", The Journal of Biological Chemistry vol. 275 No. 33, pp. 25562-25571 (2000).
Baba, et al "A small-molecule, nonpeptide CCR5 antagonist with highly potent and selective anti-HIV-1 activity", Proc. Natl. Acad. Sci, vol. 96, pp. 5698-5703 (1999).

(Continued)

Primary Examiner—Rebecca Anderson
Assistant Examiner—Jason M Nolan
(74) Attorney, Agent, or Firm—Terrance J. Bogie

(57) ABSTRACT

The present application describes modulators of MCP-1 of formula (I):

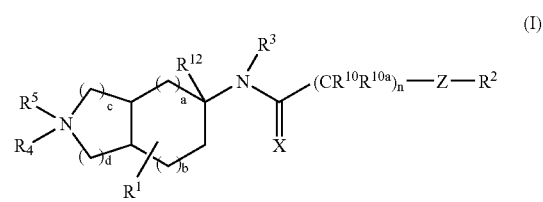

or stereoisomers or pharmaceutically acceptable salts thereof, wherein X, Z, a, b, c, d, n, $R^1$, $R^2$, $R^3$, $R^4$, $R^5$, $R^{10}$, $R^{10a}$, and $R^{12}$, are as defined herein. In addition, methods of treating and preventing inflammatory diseases such as asthma and allergic diseases, as well as autoimmune pathologies such as rheumatoid arthritis and atherosclerosis using modulators of formula (I) are disclosed.

7 Claims, No Drawings

OTHER PUBLICATIONS

Luster, M.D., Ph.D. Andrew D., "Chemokines-Chemotactic Cytokines that Mediate Inflammation", The New England Journal of Medicine, vol. 338, pp. 436-445.

Trivedi et al., "Chemokines: Targets for Novel Therapeutics", Ann. Reports Med. Chem., vol. 35, pp. 191-200 (2000).

* cited by examiner

SUBSTITUTED BICYCLOALKYLAMINE DERIVATIVES AS MODULATORS OF CHEMOKINE RECEPTOR ACTIVITY

This application claims the benefit of U.S. Provisional Application No. 60/545,921, filed Feb. 19, 2004, incorporated herein by reference in its entirety.

FIELD OF THE INVENTION

This invention relates generally to modulators of chemokine receptor activity, pharmaceutical compositions containing the same, and methods of using the same as agents for treatment and prevention of inflammatory diseases, allergic and autoimmune diseases, and in particular, asthma, rheumatoid arthritis, atherosclerosis, and multiple sclerosis.

BACKGROUND OF THE INVENTION

Chemokines are chemotactic cytokines, of molecular weight 6-15 kDa, that are released by a wide variety of cells to attract and activate, among other cell types, macrophages, T and B lymphocytes, eosinophils, basophils and neutrophils (reviewed in: Luster, *New Eng. J. Med.* 1998, 338, 436-445 and Rollins, *Blood* 1997, 90, 909-928). There are two major classes of chemokines, CXC and CC, depending on whether the first two cysteines in the amino acid sequence are separated by a single amino acid (CXC) or are adjacent (CC). The CXC chemokines, such as interleukin-8 (IL-8), neutrophil-activating protein-2 (NAP-2) and melanoma growth stimulatory activity protein (MGSA) are chemotactic primarily for neutrophils and T lymphocytes, whereas the CC chemokines, such as RANTES, MIP-1α, MIP-1β, the monocyte chemotactic proteins (MCP-1, MCP-2, MCP-3, MCP-4, and MCP-5) and the eotaxins (-1 and -2) are chemotactic for, among other cell types, macrophages, T lymphocytes, eosinophils, dendritic cells, and basophils. There also exist the chemokines lymphotactin-1, lymphotactin-2 (both C chemokines), and fractalkine (a $CX_3C$ chemokine) that do not fall into either of the major chemokine subfamilies.

The chemokines bind to specific cell-surface receptors belonging to the family of G-protein-coupled seven-transmembrane-domain proteins (reviewed in: Horuk, *Trends Pharm. Sci.* 1994, 15, 159-165) which are termed "chemokine receptors." On binding their cognate ligands, chemokine receptors transduce an intracellular signal though the associated trimeric G proteins, resulting in, among other responses, a rapid increase in intracellular calcium concentration, changes in cell shape, increased expression of cellular adhesion molecules, degranulation, and promotion of cell migration. There are at least ten human chemokine receptors that bind or respond to CC chemokines with the following characteristic patterns (reviewed in Zlotnik and Oshie *Immunity* 2000, 12, 121): CCR-1 (or "CKR-1" or "CC-CKR-1") [MIP-1α, MCP-3, MCP-4, RANTES] (Ben-Barruch, et al., *Cell* 1993, 72, 415-425, and Luster, *New Eng. J. Med.* 1998, 338, 436-445); CCR-2A and CCR-2B (or "CKR-2A"/"CKR-2B" or "CC-CKR-2A"/"CC-CKR-2B") [MCP-1, MCP-2, MCP-3, MCP-4, MCP-5] (Charo, et al., *Proc. Natl. Acad. Sci. USA* 1994, 91, 2752-2756, and Luster, *New Eng. J. Med.* 1998, 338, 436-445); CCR-3 (or "CKR-3" or "CC-CKR-3") [eotaxin-1, eotaxin-2, RANTES, MCP-3, MCP-4] (Combadiere, et al., *J. Biol. Chem.* 1995, 270, 16491-16494, and Luster, *New Eng. J. Med.* 1998, 338, 436-445); CCR-4 (or "CKR-4" or "CC-CKR-4") [TARC, MDC] (Power, et al., *J. Biol. Chem.* 1995, 270, 19495-19500, and Luster, *New Eng. J. Med.* 1998, 338, 436-445); CCR-5 (or "CKR-5" OR "CC-CKR-5") [MIP-1α, RANTES, MIP-1β] (Sanson, et al., *Biochemistry* 1996, 35, 3362-3367); CCR-6 (or "CKR-6" or "CC-CKR-6") [LARC] (Baba, et al., *J. Biol. Chem.* 1997, 272, 14893-14898); CCR-7 (or "CKR-7" or "CC-CKR-7") [ELC] (Yoshie et al., *J. Leukoc. Biol.* 1997, 62, 634-644); CCR-8 (or "CKR-8" or "CC-CKR-8") [I-309] (Napolitano et al., *J. Immunol.*, 1996, 157, 2759-2763); CCR-10 (or "CKR-10" or "CC-CKR-10") [MCP-1, MCP-3] (Bonini, et al., *DNA and Cell Biol.* 1997, 16, 1249-1256); and CCR-11 [MCP-1, MCP-2, and MCP-4] (Schweickert, et al., *J. Biol. Chem.* 2000, 275, 90550).

Mammalian cytomegaloviruses, herpesviruses and poxviruses have also been shown to express, in infected cells, proteins with the binding properties of chemokine receptors (reviewed in: Wells and Schwartz, *Curr. Opin. Biotech.* 1997, 8, 741-748). Human CC chemokines, such as RANTES and MCP-3, can cause rapid mobilization of calcium via these virally encoded receptors. Receptor expression may be permissive for infection by allowing for the subversion of normal immune system surveillance and response to infection. Additionally, human chemokine receptors, such as CXCR4, CCR2, CCR3, CCR5 and CCR8, can act as co-receptors for the infection of mammalian cells by microbes as with, for example, the human immunodeficiency viruses (HIV).

The chemokines and their cognate receptors have been implicated as being important mediators of inflammatory, infectious, and immunoregulatory disorders and diseases, including asthma and allergic diseases, as well as autoimmune pathologies such as rheumatoid arthritis and atherosclerosis (reviewed in: P. H. Carter, *Current Opinion in Chemical Biology* 2002, 6, 510; Trivedi et al, *Ann. Reports Med. Chem.* 2000, 35, 191; Saunders and Tarby, *Drug Disc. Today* 1999, 4, 80; Premack and Schall, *Nature Medicine* 1996, 2, 1174). Various studies performed to date support these implications. For example, studies completed to date have indicated that the antagonisum of the MCP-1/CC2 interaction may be useful in treating rheumatoid arthritis; ameliorate chronic polyadjuvant-induced arthritis (Youssef et al., *J. Clin. Invest.* 2000, 106, 361); collagen-induced arthritis (see Ogata et al., *J. Pathol.* 1997, 182, 106); streptococcal cell wall-induced arthritis (Schimmer et al., *J. Immunol.* 1998, 160, 1466); MRL-1pr mouse model of arthritis (Gong et al., *J. Exp. Med.* 1997, 186, 131); atherosclerosis (Rezaie-Majd et al, *Arterioscler. Thromb. Vasc. Biol.* 2002, 22, 1194-1199; Gu et al., *Mol. Cell* 1998, 2, 275; Gosling et al., *J. Clin. Invest.* 1999, 103, 773; Boring et al, *Nature* 1998, 394, 894; and Ni et al. *Circulation* 2001, 103, 2096-2101); multiple sclerosis (Iarlori et al., *J. Neuroimmunol.* 2002, 123, 170-179; Kennedy et al., *J. Neuroimmunol.* 1998, 92, 98; Fife et al., *J. Exp. Med.* 2000, 192, 899; and Izikson et al., *J. Exp. Med.* 2000, 192, 1075); organ transplant rejection (Reynaud-Gaubert et al., *J. of Heart and Lung Transplant.*, 2002, 21, 721-730; Belperio et al., *J. Clin. Invest.* 2001, 108, 547-556; and Belperio et al., *J. Clin. Invest.* 2001, 108, 547-556); asthma (Gonzalo et al., *J. Exp. Med.* 1998, 188, 157; Lukacs, et al., *J. Immunol.* 1997, 158, 4398; and Lu et al., *J. Exp. Med.* 1998, 187, 601); kidney disease (Lloyd et al., *J. Exp. Med.* 1997, 185, 1371; and Tesch et al., *J. Clin. Invest.* 1999, 103, 73); lupus erythematosus (Tesch et al., *J. Exp. Med.* 1999, 190, 1813); colitis (Andres et al., *J. Immunol.* 2000, 164, 6303); alveolitis (Jones, et al., *J. Immunol.* 1992, 149, 2147); cancer (Salcedo et al., *Blood* 2000, 96, 34-40); restinosis (Roque et al. *Arterioscler. Thromb. Vasc. Biol.* 2002, 22, 554-559); inflammatory bowel disease (Reinecker et al., *Gastroenterology* 1995, 108, 40; and Grimm et al., *J. Leukoc. Biol.* 1996, 59, 804); brain trauma (King et al., *J. Neuroimmunol.* 1994, 56, 127; and Berman et al., *J. Immunol.* 1996, 156, 3017); transplant arteriosclerosis (Russell et al., *Proc. Natl. Acad. Sci. USA* 1993, 90, 6086); idiopathic pulmonary fibrosis (Antoniades et al., *Proc. Natl. Acad. Sci. USA* 1992, 89, 5371); psoriasis (Deleuran et al., *J. Dermatol. Sci.* 1996, 13, 228; and Gillitzer et al., *J. Invest. Dermatol.* 1993, 101, 127); and HIV and HIV-1-associated dementia (Garzino-Demo, WO 99/46991; Doranz et al., *Cell* 1996, 85, 1149; Connor et al., *J. Exp. Med.* 1997, 185, 621; and Smith et al., *Science* 1997, 277, 959). Similarly, demonstration of the importance of the MCP-1/CCR-2 interaction has been reported in the literature. For example, Lu et al., *J. Exp. Med.* 1998, 187, 601; Boring et al., *J. Clin. Invest.* 1997, 100, 2552; Kuziel et al., *Proc. Natl. Acad. Sci. USA* 1997, 94, 12053; and Kurihara et al., *J. Exp. Med.* 1997, 186, 1757.

Small molecules including ureido-substituted cyclic amines, arylalkyl cyclic amines, acyclic diamines, cyclic diamines, 4,4-disubstituted piperidines, 1,2,3,4-tetrahydroisoquinolines, imidazolium compounds, 1,4-disubstituted piperazines, piperidines, bicyclic piperidines, substituted furo[2,3,-B]pyridines, and diazabicyclic compounds have been reported in the literature as antagonists of MCP-1 and/or CCR receptors. For example, Trivedi et al, *Ann. Reports Med. Chem.* 2000, 35, 191; Shiota et al., WO 99/25686; Shiota et al., WO 00/69815; C. Tarby and W. Moree, WO 00/69820; P. Carter and R. Cherney, WO 02/50019; R. Cherney, WO 02/060859; Matsumoto et al., WO 03/091245; Jiao et al., WO 03/093231; Axten et al., WO 03/101970; Pennell et al., WO 03/105853; Blumberg et al., WO 04/009550; Blumberg et al., WO 04/009588; Toupence et al., WO 04/012671; and Colon-Cruz et al., WO-02/070523. Similarly, MCP-1 and/or CCR receptor antagonistic indolopiperidines quaternary amines, spiropiperidines, 2-substituted indoles and benzimidazoles, pyrazolone derivatives, dialkylhomopiperazines, N,N-dialkylhomopiperazines, bicyclic pyrroles, tetrahydropyranyl cyclopentyl tetrahyropyridopyridines, N-aryl sulfonamides, pyrimidyl sulphone amides, 3,4-diamine-3-cyclobutene-1,2-diones, substituted heterocyclic compounds, substituted benzanilides, bipiperidinyl derivatives, and 5-aryl pentadienamides have been reported in the literature. For example, Forbes et al., *Bioorg. Med. Chem. Lett.* 2000, 10, 1803; Mirzadegan et al., *J. Biol. Chem.* 2000, 275, 25562; Baba et al., *Proc. Natl. Acad. Sci.* 1999, 96, 5698; A. Faull and J. Kettle, WO 00/46196; Barker et al., WO 99/07351; Barker et al., WO 99/07678; Padia et al., U.S. Pat. No. 6,011,052; Connor et al., WO 98/06703; Shiota et al., WO 97/44329; Barker et al., WO 99/40913; Barker et al., WO 99/40914; Jiao et al., WO 03/092568; Fleming et al., WO 03/99773; Habashita et al., WO 04/007472; Ebden et al., WO 04/011443; Taveras et al., WO 04/011418; Bondinell et al., WO 04/010942, WO 04/010943 and WO 04/011427; Albert et al., WO 02/081449; and Carson, et al., Cambridge Health Tech Institute Chemokine Symposium, McLean, Va., USA, 1999.

However, the foregoing reference compounds are readily distinguished structurally from the present invention by virtue of substantial differences in the terminal functionality, the attachment functionality, the core functionality, and/or nature of the bicyclic ring system. Accordingly, the prior art does not disclose nor suggest the unique combination of structural fragments that embody the novel compounds described herein. Furthermore, the prior art does not disclose or suggest that the compounds of the present invention would be effective as MCP-1 antagonists.

It should be noted that CCR-2 is also the receptor for the chemokines MCP-2, MCP-3, MCP-4, and MCP-5 (Luster, *New Eng. J. Med.* 1998, 338, 436-445). Since it is believed that the compounds of formula (I) described herein antagonize MCP-1 by binding to the CCR-2 receptor, it may be that these compounds of formula (I) are also effective antagonists of the actions of MCP-2, MCP-3, MCP-4, and MCP-5 that are mediated by CCR-2. Accordingly, when reference is made herein to "antagonism of MCP-1," it is to be assumed that this is equivalent to "antagonism of chemokine stimulation of CCR-2."

SUMMARY OF THE INVENTION

Accordingly, the present invention provides novel antagonists or partial agonists/antagonists of MCP-1 receptor activity, or pharmaceutically acceptable salts or prodrugs thereof.

The present invention provides pharmaceutical compositions comprising a pharmaceutically acceptable carrier and a therapeutically effective amount of at least one of the compounds of the present invention or a pharmaceutically acceptable salt or prodrug form thereof.

The present invention provides a method for treating rheumatoid arthritis, multiple sclerosis, and atherosclerosis, comprising administering to a host in need of such treatment a therapeutically effective amount of at least one of the compounds of the present invention or a pharmaceutically acceptable salt or prodrug form thereof.

The present invention provides a method for treating inflammatory diseases, comprising administering to a host in need of such treatment a therapeutically effective amount of at least one of the compounds of the present invention or a pharmaceutically acceptable salt or prodrug form thereof.

The present invention provides novel cyclic derivatives for use in therapy.

The present invention provides the use of novel cyclic derivatives for the manufacture of a medicament for the treatment of inflammatory diseases.

These and other features of the invention, which will become apparent during the following detailed description, have been achieved by the inventors' discovery that compounds of formula (I):

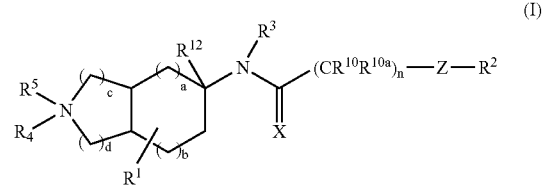

or stereoisomers or pharmaceutically acceptable salts thereof, wherein X, Z, a, b, c, d, n, $R^1$, $R^2$, $R^3$, $R^4$, $R^5$, $R^{10}$, $R^{10a}$, and $R^{12}$, are defined below, are effective modulators of MCP-1 and chemokine activity.

DETAILED DESCRIPTION OF THE PRESENT INVENTION

In one embodiment, the present invention provides novel compounds of formula (I):

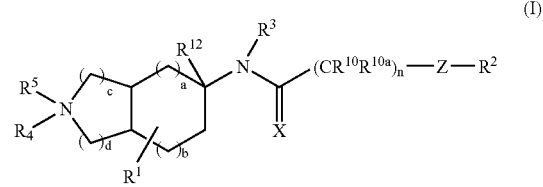

or a stereoisomer or a pharmaceutically acceptable salt thereof, wherein:

X is selected from O or S;

Z is selected from a bond, —C(O)—, —C(O)NR$^8$—, —NR$^8$—, —NR$^8$—CR$^{14}$R$^{14}$—, —NR$^8$C(O)—, —NR$^8$C(O)NH—, —NR$^8$C(S)NH—, —NR$^8$SO$_2$—, —NR$^8$SO$_2$NH—, —OC(O)NR$^8$—, —NR$^8$C(O)O—, —(CR$^{25}$R$^{25}$)$_u$—, —CR$^{14}$=CR$^{14}$—, —CR$^{25}$R$^{25}$C(O)—, —C(O)CR$^{25}$R$^{25}$—, —CR$^{25}$R$^{25}$C(=N—OR$^{14}$)—, —O—CR$^{14}$R$^{14}$—, —CR$^{14}$R$^{14}$—O—, —O—, —CHR$^{14}$—NR$^8$—, —S(O)$_p$—, —S(O)$_p$—CR$^{14}$R$^{14}$—, and —S(O)$_p$—NR$^8$—;

R$^1$ is selected from H, R$^6$, C$_{1-6}$ alkyl substituted with 0-3 R$^6$, C$_{2-6}$ alkenyl substituted with 0-3 R$^6$, C$_{2-6}$ alkynyl substituted with 0-3 R$^6$, C$_{6-10}$ aryl group substituted with 0-5 R$^6$, and a 5-10 membered heteroaryl system containing 1-4 heteroatoms selected from N, O, and S, substituted with 0-3 R$^6$;

R$^2$ is selected from a C$_{6-10}$ aryl group substituted with 0-5 R$^7$ and a 5-10 membered heteroaryl system containing 1-4 heteroatoms selected from N, O, and S, substituted with 0-3 R$^7$;

R$^3$ is selected from H, methyl, and ethyl;

R$^4$ is absent, taken with the nitrogen to which it is attached to form an N-oxide, or selected from C$_{1-8}$ alkyl, C$_{2-8}$ alkenyl, C$_{2-8}$ alkynyl, (CR'R')$_r$C$_{3-6}$ cycloalkyl, (CR'R')$_q$C(O)R$^{4b}$, (CR'R')$_q$C(O)NR$^{4a}$R$^{4a}$, (CR'R')$_q$C(O)OR$^{4b}$, and a (CR'R')$_r$—C$_{3-10}$ carbocyclic residue substituted with 0-3 R$^{4c}$;

R$^{4a}$, at each occurrence, is independently selected from H, C$_{1-6}$ alkyl, (CR'R')$_r$C$_{3-6}$ cycloalkyl, and phenyl;

alternatively, two R$^{4a}$s, together with the N to which they are attached, join to form a 3-8 membered heterocycle containing 0-1 additional heteroatoms selected from N, O and S;

R$^{4b}$, at each occurrence, is independently selected from C$_{1-6}$ alkyl, C$_{2-8}$ alkenyl, (CR'R')$_r$C$_{3-6}$ cycloalkyl, C$_{2-8}$ alkynyl, and phenyl;

R$^{4c}$, at each occurrence, is independently selected from C$_{1-6}$ alkyl, C$_{2-8}$ alkenyl, C$_{2-8}$ alkynyl, C$_{3-6}$ cycloalkyl, Cl, F, Br, I, CN, NO$_2$, (CF$_2$)$_r$CF$_3$, (CR'R')$_r$OC$_{1-5}$ alkyl, (CR'R')$_r$OH, (CR'R')$_r$SC$_{1-5}$ alkyl, (CR'R')$_r$NR$^{4a}$R$^{4a}$, and (CR'R')$_r$phenyl;

R$^5$ is selected from H, C$_{1-6}$ alkyl substituted with 0-2 R$^{5e}$, —C(O)R$^{5b}$, —C(O)OR$^{5b}$, —C(O)NR$^{5f}$R$^{5f}$, a C$_{3-10}$ carbocyclic residue substituted with 0-5 R$^{5e}$, and a 5-10 membered heterocyclic system containing 1-4 heteroatoms selected from N, O, and S, substituted with 0-3 R$^{5e}$;

R$^{5b}$, at each occurrence, is selected from C$_{1-6}$ alkyl substituted with 0-3 R$^{5e}$, C$_{3-8}$ alkenyl substituted with 0-2 R$^{5e}$, C$_{3-8}$ alkynyl substituted with 0-2 R$^{5e}$, a (CR'R')$_r$—C$_{3-6}$ carbocyclic residue substituted with 0-2 R$^{5e}$, and a (CR'R')$_r$-5-6 membered heterocyclic system containing 1-4 heteroatoms selected from N, O, and S, substituted with 0-3 R$^{5e}$;

R$^{5e}$, at each occurrence, is selected from C$_{1-6}$ alkyl, C$_{2-8}$ alkenyl, C$_{2-8}$ alkynyl, C$_{3-6}$ cycloalkyl, Cl, F, Br, I, CN, NO$_2$, (CF$_2$)$_r$CF$_3$, (CR'R')$_r$OC$_{1-5}$ alkyl, OH, SH, (CR'R')$_r$SC$_{1-5}$ alkyl, (CR'R')$_r$NR$^{5f}$R$^{5f}$, a (CR'R')$_r$C$_{3-6}$ carbocyclic residue substituted with 0-3 R$^{6e}$, and a (CR'R')$_r$-5-6 membered heterocyclic system containing 1-4 heteroatoms selected from N, O, and S, substituted with 0-2 R$^{6e}$;

R$^{5f}$, at each occurrence, is selected from H, C$_{1-6}$ alkyl, and C$_{3-6}$ cycloalkyl;

alternatively, two R$^{5f}$s, together with the N to which they are attached, join to form a 3-8 membered heterocycle containing 0-1 additional heteroatoms selected from N, O and S;

R$^6$, at each occurrence, is selected from C$_{1-8}$ alkyl, C$_{2-8}$ alkenyl, C$_{2-8}$ alkynyl, (CR'R')$_r$C$_{3-6}$ cycloalkyl, Cl, Br, I, F, NO$_2$, CN, (CR'R')$_r$NR$^{6a}$R$^{6a}$, (CR'R')$_r$OH, (CR'R')$_r$O(CR'R')$_r$R$^{6d}$, (CR'R')$_r$SH, (CR'R')$_r$C(O)H, (CR'R')$_r$S(CR'R')$_r$R$^{6d}$, (CR'R')$_r$SC(O)(CR'R')$_r$R$^{6a}$, (CR'R')$_r$C(O)OH, (CR'R')$_r$C(O)(CR'R')$_r$R$^{6a}$, (CR'R')$_r$C(O)NR$^{6a}$R$^{6a}$, (CR'R')$_r$NR$^{6f}$C(O) (CR'R')$_r$R$^{6a}$, (CR'R')$_r$C(O)O(CR'R')$_r$R$^{6d}$, (CR'R')$_r$OC(O)(CR'R')$_r$R$^{6a}$, (CR'R')$_r$OC(O)NR$^{6a}$(CR'R')$_r$R$^{6d}$, (CR'R')$_r$NR$^{6a}$C(O)NR$^{6a}$(CR'R')$_r$R$^{6d}$, (CR'R')$_r$NR$^{6a}$C(S)NR$^{6a}$(CR'R')$_r$R$^{6d}$, (CR'R')$_r$NR$^{6f}$C(O)O(CR'R')$_r$R$^{6a}$, (CR'R')$_r$C(=NR$^{6f}$)NR$^{6a}$R$^{6a}$, (CR'R')$_r$NHC(=NR$^{6f}$)NR$^{6f}$R$^{6f}$, (CR'R')$_r$S(O)$_p$(CR'R')$_r$R$^{6a}$, (CR'R')$_r$S(O)$_2$NR$^{6a}$R$^{6a}$, (CR'R')$_r$NR$^{6f}$S(O)$_2$NR$^{6a}$R$^{6a}$, (CR'R')$_r$NR$^{6f}$S(O)$_2$(CR'R')$_r$R$^{6a}$, C$_{1-6}$ haloalkyl, C$_{2-8}$ alkenyl substituted with 0-3 R$^1$, C$_{2-8}$ alkynyl substituted with 0-3 R', (CR'R')$_r$phenyl substituted with 0-3 R$^{6e}$, and a (CR'R')$_r$-5-6 membered heterocyclic system containing 1-2 heteroatoms selected from N, O, and S, substituted with 0-2 R$^{6e}$;

alternatively, two R$^{6s}$ on adjacent atoms on R$^1$ may join to form a cyclic acetal;

R$^{6a}$, at each occurrence, is selected from H, methyl, C$_{2-6}$ alkyl substituted with 0-2 R$^{6e}$, C$_{3-8}$ alkenyl substituted with 0-2 R$^{6e}$, C$_{3-8}$ alkynyl substituted with 0-2 R$^{6e}$, a (CR'R')$_r$—C$_{3-10}$ carbocyclic residue substituted with 0-5 R$^{6e}$, and a (CR'R')$_r$-5-10 membered heterocyclic system containing 1-4 heteroatoms selected from N, O, and S, substituted with 0-2 R$^{6e}$;

alternatively, two R$^{6a}$s, together with the N to which they are attached, join to form a 3-8 membered heterocycle containing 0-1 additional heteroatoms selected from N, O, and S;

R$^{6d}$, at each occurrence, is selected from C$_{3-8}$ alkenyl substituted with 0-2 R$^{6e}$, C$_{3-8}$ alkynyl substituted with 0-2 R$^{6e}$, methyl, CF$_3$, C$_{2-4}$ alkyl substituted with 0-3 R$^{6e}$, C$_{2-4}$ haloalkyl, a (CR'R')$_r$—C$_{3-10}$ carbocyclic residue substituted with 0-3 R$^{6e}$, and a (CR'R')$_r$-5-6 membered heterocyclic system containing 1-4 heteroatoms selected from N, O, and S, substituted with 0-3 R$^{6e}$;

R$^{6e}$, at each occurrence, is selected from C$_{1-6}$ alkyl, C$_{2-8}$ alkenyl, C$_{2-8}$ alkynyl, (CR'R')$_r$C$_{3-6}$ cycloalkyl, Cl, F, Br, I, CN, NO$_2$, (CF$_2$)$_r$CF$_3$, (CR'R')$_r$OC$_{1-5}$ alkyl, OH, SH, (CR'R')$_r$SC$_{1-5}$ alkyl, (CR'R')$_r$NR$^{6f}$R$^{6f}$, and (CR'R')$_r$phenyl;

R$^{6f}$, at each occurrence, is selected from H, C$_{1-5}$ alkyl, and C$_{3-6}$ cycloalkyl, and phenyl;

alternatively, two R$^{6f}$s, together with the N to which they are attached, join to form a 3-8 membered heterocycle containing 0-1 additional heteroatoms selected from N, O and S;

R$^7$, at each occurrence, is selected from C$_{1-8}$ alkyl, C$_{2-8}$ alkenyl, C$_{2-8}$ alkynyl, (CR'R')$_r$C$_{3-6}$ cycloalkyl, Cl, Br, I, F, NO$_2$, CN, (CR'R')$_r$NR$^{7a}$R$^{7a}$, (CR'R')$_r$OH, (CR'R')$_r$O(CR'R')$_r$R$^{7d}$, (CR'R')$_r$SH, (CR'R')$_r$C(O)H, (CR'R')$_r$S(CR'R')$_r$R$^{7d}$, (CR'R')$_r$C(O)OH, (CR'R')$_r$C(O)(CR'R')$_r$R$^{7b}$, (CR'R')$_r$C(O)NR$^{7a}$R$^{7a}$, (CR'R')$_r$NR$^{7f}$C(O)(CR'R')$_r$R$^{7b}$, (CR'R')$_r$C(O)O(CR'R')$_r$R$^{7d}$, (CR'R')$_r$OC(O)(CR'R')$_r$R$^{7b}$, (CR'R')$_r$OC(O)NR$^{7a}$(CR'R')$_r$R$^{7a}$, (CR'R')$_r$NR$^{7a}$C(O)NR$^{7a}$(CR'R')$_r$R$^{7a}$, (CR'R')$_r$NR$^{7f}$C(O)O(CR'R')$_r$R$^{7d}$, (CR'R')$_r$C(=NR$^{7f}$)NR$^{7a}$R$^{7a}$, (CR'R')$_r$NHC(=NR$^{7f}$)NR$^{7f}$R$^{7f}$, (CR'R')$_r$S(O)$_p$(CR'R')$_r$R$^{7b}$, (CR'R')$_r$S(O)$_2$NR$^{7a}$R$^{7a}$, (CR'R')$_r$NR$^{7a}$S(O)$_2$NR$^{7a}$R$^{7a}$, (CR'R')$_r$NR$^{7f}$S(O)$_2$(CR'R')$_r$R$^{7b}$, C$_{1-6}$ haloalkyl, C$_{2-8}$ alkenyl substituted with 0-3 R', $C_{2-8}$ alkynyl substituted with 0-3 R', a $(CR'R')_r$—$C_{3-10}$ carbocyclic residue substituted with 0-3 $R^{7e}$, and a $(CR'R')_r$-5-10 membered heterocyclic system containing 1-4 heteroatoms selected from N, O, and S, substituted with 0-3 $R^{7e}$;

alternatively, two $R^{7s}$ on adjacent atoms on $R^2$ may join to form a cyclic acetal;

$R^{7a}$, at each occurrence, is independently selected from H, methyl substituted with 0-1 $R^{7g}$, $C_{2-6}$ alkyl substituted with 0-2 $R^{7e}$, $C_{3-8}$ alkenyl substituted with 0-2 $R^{7e}$, $C_{3-8}$ alkynyl substituted with 0-2 $R^{7e}$, a $(CR'R')_r$—$C_{3-10}$ carbocyclic residue substituted with 0-5 $R^{7e}$, and a $(CR'R')_r$-5-10 membered heterocyclic system containing 1-4 heteroatoms selected from N, O, and S, substituted with 0-2 $R^{7e}$;

alternatively, two $R^{7a}$s, together with the N to which they are attached, join to form a 3-8 membered heterocycle containing 0-1 additional heteroatoms selected from N, O and S;

$R^{7b}$, at each occurrence, is selected from $C_{1-6}$ alkyl substituted with 0-2 $R^{7e}$, $C_{3-8}$ alkenyl substituted with 0-2 $R^{7e}$, $C_{3-8}$ alkynyl substituted with 0-2 $R^{7e}$, a $(CR'R')_rC_{3-6}$ carbocyclic residue substituted with 0-3 $R^{7e}$, and a $(CR'R')_r$-4-6 membered heterocyclic system containing 1-4 heteroatoms selected from N, O, and S, substituted with 0-2 $R^{7e}$;

$R^{7d}$, at each occurrence, is selected from $C_{3-8}$ alkenyl substituted with 0-2 $R^{7e}$, $C_{3-8}$ alkynyl substituted with 0-2 $R^{7e}$, methyl, $CF_3$, $C_{2-4}$ haloalkyl, $C_{2-6}$ alkyl substituted with 0-3 $R^{7e}$, a $(CR'R')_r$—$C_{3-10}$ carbocyclic residue substituted with 0-3 $R^{7e}$, and a $(CR'R')_r$-5-6 membered heterocyclic system containing 1-4 heteroatoms selected from N, O, and S, substituted with 0-3 $R^{7e}$;

$R^{7e}$, at each occurrence, is selected from $C_{1-6}$ alkyl, $C_{2-8}$ alkenyl, $(CR'R')_r$cyclopropyl, Cl, F, Br, CN, $(CF_2)_rCF_3$, $(CR'R')_rOC_{1-5}$ alkyl, OH, $C(O)OC_{1-5}$ alkyl, $(CR'R')_rNR^{7f}R^{7f}$, and acetyl;

$R^{7f}$, at each occurrence, is selected from H, $C_{1-5}$ alkyl, and $C_{3-6}$ cycloalkyl, and phenyl;

alternatively, two $R^{7f}$s, together with the N to which they are attached, join to form a 3-8 membered heterocycle containing 0-1 additional heteroatoms selected from N, O and S;

$R^{7g}$ is independently selected from —C(O)$R^{7b}$, —C(O)O$R^{7d}$, —C(O)NR$^{7f}R^{7f}$, and $(CR'R')_r$phenyl;

R', at each occurrence, is independently selected from H, methyl, and $C_{2-6}$ alkyl;

alternatively, two R's, along with the carbon atom to which they are attached, join to form a cyclopropyl ring;

$R^8$ is selected from H, $C_{1-4}$ alkyl, and $C_{3-4}$ cycloalkyl;

$R^{10}$ and $R^{10a}$ are independently selected from H and $C_{1-4}$ alkyl substituted with 0-1 $R^{10b}$, alternatively, $R^{10}$ and $R^{10a}$ can join to form a $C_{3-6}$ cycloalkyl;

$R^{10b}$, at each occurrence, is independently selected from —OH, —SH, NR$^{10c}$R$^{10c}$, —C(O)NR$^{10c}$R$^{10c}$, and —NHC(O)R$^{10c}$;

$R^{10c}$ is selected from H, $C_{1-4}$ alkyl and $C_{3-6}$ cycloalkyl;

alternatively, two $R^{10c}$s, together with the N to which they are attached, join to form a 3-8 membered heterocycle containing 0-1 additional heteroatoms selected from N, O and S;

$R^{12}$ is selected from H and $C_{1-4}$ alkyl;

$R^{14}$, at each occurrence, is independently selected from H and $C_{1-4}$alkyl;

alternatively, two $R^{14}$s, along with the carbon atom to which they are attached, join to form a $C_{3-6}$ carbocyclic ring;

$R^{25}$, at each occurrence, is independently selected from H, $C_{1-4}$alkyl, OH, $NH_2$, —O—$C_{1-4}$ alkyl, NR$^{25a}$R$^{25a}$, C(O)NR$^{25a}$R$^{25a}$, NR$^{25a}$C(O)R$^{25b}$, NR$^{25a}$C(O)OR$^{25b}$, OC(O)NR$^{25a}$R$^{25a}$, and (CHR)$_r$C(O)OR$^{25b}$;

alternatively, two $R^{25s}$, along with the carbon atom or atoms to which they are attached, join to form a $C_{3-6}$ carbocyclic ring;

$R^{25a}$, at each occurrence, is independently selected from H, and $C_{1-4}$ alkyl;

alternatively, two $R^{25a}$s, together with the N to which they are attached, join to form a 3-8 membered heterocycle containing 0-1 additional heteroatoms selected from N, O and S;

$R^{25b}$, at each occurrence, is independently selected from H, $C_{1-4}$ alkyl, $C_{3-6}$ alkenyl, and $C_{3-6}$ alkynyl;

a is selected from 0 and 1;
b is selected from 0, 1, 2 and 3; with the proviso that a+b is selected from 1, 2 and 3;
c is selected from 0 and 1;
d is selected from 1, 2 and 3;
with the proviso that c+d is selected from 2 and 3;
n is selected from 1 and 2;
p, at each occurrence, is independently selected from 0, 1, and 2;
q, at each occurrence, is independently selected from 1, 2, 3, and 4;
r, at each occurrence, is independently selected from 0, 1, 2, 3, and 4; and
u is selected from 1, 2 and 3.

Some preferred compounds of the present invention are those in which

X is selected from O or S;

Z is selected from a bond, —C(O)NR$^8$—, —NR$^8$—, —NR$^8$C(O)—, —NR$^8$C(O)NH—, —NR$^8$SO$_2$—, —(CR$^{25}$R$^{25}$)$_u$—, —CR$^{14}$=CR$^{14}$—, and —CR$^{25}$R$^{25}$C(O)—;

$R^1$ is selected from H, $R^6$, $C_{1-6}$ alkyl substituted with 0-3 $R^6$, $C_{6-10}$ aryl group substituted with 0-5 $R^6$, and a 5-10 membered heteroaryl system containing 1-4 heteroatoms selected from N, O, and S, substituted with 0-3 $R^6$;

$R^2$ is selected from a $C_{6-10}$ aryl group substituted with 0-5 $R^7$ and a 5-10 membered heteroaryl system containing 1-4 heteroatoms selected from N, O, and S, substituted with 0-3 $R^7$;

$R^3$ is selected from H and methyl;

$R^4$ is absent, taken with the nitrogen to which it is attached to form an N-oxide, or $C_{1-8}$ alkyl;

$R^5$ is selected from H and $C_{1-6}$ alkyl substituted with 0-2 $R^{5e}$;

$R^{5e}$, at each occurrence, is selected from $C_{1-6}$ alkyl, $C_{2-8}$ alkenyl, $C_{2-8}$ alkynyl, $C_{3-6}$ cycloalkyl, F, $(CF_2)_rCF_3$, $(CR'R')_rOC_{1-5}$ alkyl, and $(CR'R')_rNR^{5f}R^{5f}$;

$R^{5f}$, at each occurrence, is selected from H and $C_{1-6}$ alkyl;

alternatively, two $R^{5f}$s, together with the N to which they are attached, join to form a 3-8 membered heterocycle containing 0-1 additional heteroatoms selected from N, O and S;

$R^6$, at each occurrence, is selected from $C_{1-8}$ alkyl, $C_{2-8}$ alkenyl, $C_{2-8}$ alkynyl, $(CR'R')_rC_{3-6}$ cycloalkyl, $(CR'R')_rNR^{6a}R^{6a}$, $(CR'R')_rOH$, $(CR'R')_rO(CR'R')_rR^{6d}$, $(CR'R')_rS(CR'R')_rR^{6d}$, $(CR'R')_rC(O)(CR'R')_rR^{6a}$, $(CR'R')_rC(O)NR^{6a}R^{6a}$, $(CR'R')_rNR^{6f}C(O)(CR'R')_rR^{6a}$, $(CR'R')_rC(O)O(CR'R')_rR^{6d}$, $(CR'R')_rOC(O)(CR'R')_rR^{6a}$, $(CR'R')_rOC(O)NR^{6a}(CR'R')_rR^{6d}$, $(CR'R')_rNR^{6a}C(O)NR^{6a}(CR'R')_rR^{6d}$, $(CR'R')_rNR^{6f}C(O)O(CR'R')_rR^{6a}$, $(CR'R')_rS(O)_p(CR'R')_rR^{6a}$, $(CR'R')_rNR^{6f}S(O)_2NR^{6a}R^{6a}$, $(CR'R')_rNR^{6f}S(O)_2(CR'R')_rR^{6a}$, $C_{1-6}$ haloalkyl, $(CR'R')_r$phenyl substituted with 0-3 $R^{6e}$, and a (CR'R')$_r$-5-6 membered heterocyclic system containing 1-2 heteroatoms selected from N, O, and S, substituted with 0-2 R$^{6e}$;

R$^{6a}$, at each occurrence, is selected from H, methyl, C$_{2-6}$ alkyl substituted with 0-2 R$^{6e}$, C$_{3-8}$ alkenyl substituted with 0-2 R$^{6e}$, C$_{3-8}$ alkynyl substituted with 0-2 R$^{6e}$, a (CR'R')$_r$—C$_{3-1}$ carbocyclic residue substituted with 0-5 R$^{6e}$, and a (CR'R')$_r$-5-10 membered heterocyclic system containing 1-4 heteroatoms selected from N, O, and S, substituted with 0-2 R$^{6e}$;

alternatively, two R$^{6a}$s, together with the N to which they are attached, join to form a 3-8 membered heterocycle containing 0-1 additional heteroatoms selected from N, O, and S;

R$^{6d}$, at each occurrence, is selected from methyl, CF$_3$, C$_{2-6}$ alkyl substituted with 0-3 R$^{6e}$, a (CR'R')$_r$—C$_{3-10}$ carbocyclic residue substituted with 0-3 R$^{6e}$, and a (CR'R')$_r$-5-6 membered heterocyclic system containing 1-4 heteroatoms selected from N, O, and S, substituted with 0-3 R$^{6e}$;

R$^{6e}$, at each occurrence, is selected from C$_{1-6}$ alkyl, Cl, F, (CF$_2$)$_r$CF$_3$, and (CR'R')$_r$OC$_{1-5}$ alkyl;

R$^{6f}$, at each occurrence, is selected from H and C$_{1-5}$ alkyl;

R$^7$, at each occurrence, is selected from C$_{1-8}$ alkyl, Cl, Br, F, CN, (CR'R')$_r$NR$^{7a}$R$^{7a}$, (CR'R')$_r$OH, (CR'R')$_r$O(CR'R')$_r$R$^{7d}$, (CR'R')$_r$C(O)(CR'R')$_r$R$^{7b}$, (CR'R')$_r$C(O)NR$^{7a}$R$^{7a}$, (CR'R')$_r$NR$^{7f}$C(O)(CR'R')$_r$R$^{7b}$, (CR'R')$_r$OC(O)NR$^{7a}$(CR'R')$_r$R$^{7a}$, (CR'R')$_r$NR$^{7a}$C(O)NR$^{7a}$(CR'R')$_r$R$^{7a}$, (CR'R')$_r$NR$^{7f}$C(O)O(CR'R')$_r$R$^{7d}$, (CR'R')$_r$S(O)$_p$(CR'R')$_r$R$^{7b}$, (CR'R')$_r$S(O)$_2$NR$^{7a}$R$^{7a}$, (CR'R')$_r$NR$^{7a}$S(O)$_2$NR$^{7a}$R$^{7a}$, (CR'R')$_r$NR$^{7f}$S(O)$_2$(CR'R')$_r$R$^{7b}$, C$_{1-6}$ haloalkyl, a (CR'R')$_r$—C$_{3-10}$ carbocyclic residue substituted with 0-3 R$^{7e}$, and a (CR'R')$_r$-5-10 membered heterocyclic system containing 1-4 heteroatoms selected from N, O, and S, substituted with 0-3 R$^{7e}$;

R$^{7a}$, at each occurrence, is independently selected from H, methyl substituted with 0-1 R$^{7g}$, C$_{2-6}$ alkyl substituted with 0-2 R$^{7e}$, a (CR'R')$_r$—C$_{3-10}$ carbocyclic residue substituted with 0-5 R$^{7e}$, and a (CR'R')$_r$-5-10 membered heterocyclic system containing 1-4 heteroatoms selected from N, O, and S, substituted with 0-2 R$^{7e}$;

alternatively, two R$^{7a}$s, together with the N to which they are attached, join to form a 3-8 membered heterocycle containing 0-1 additional heteroatoms selected from N, O and S;

R$^{7b}$, at each occurrence, is selected from C$_{1-6}$ alkyl substituted with 0-2 R$^{7e}$, C$_{3-8}$ alkenyl substituted with 0-2 R$^{7e}$, a (CR'R')$_r$C$_{3-6}$ carbocyclic residue substituted with 0-3 R$^{7e}$, and a (CR'R')$_r$-4-6 membered heterocyclic system containing 1-4 heteroatoms selected from N, O, and S, substituted with 0-2 R$^{7e}$;

R$^{7d}$, at each occurrence, is selected from methyl, C$_{2-6}$ alkyl substituted with 0-3 R$^{7e}$, a (CR'R')$_r$—C$_{3-10}$ carbocyclic residue substituted with 0-3 R$^{7e}$, and a (CR'R')$_r$-5-6 membered heterocyclic system containing 1-4 heteroatoms selected from N, O, and S, substituted with 0-3 R$^{7e}$;

R$^{7e}$, at each occurrence, is selected from C$_{1-6}$ alkyl, C$_{2-8}$ alkenyl, Cl, F, Br, CN, (CF$_2$)$_r$CF$_3$, (CR'R')$_r$OC$_{1-5}$ alkyl, OH, C(O)OC$_{1-5}$ alkyl, (CR'R')$_r$NR$^{7f}$R$^{7f}$, and acetyl;

R$^{7f}$, at each occurrence, is selected from H and C$_{1-5}$ alkyl;

alternatively, two R$^{7f}$s, together with the N to which they are attached, join to form a 3-8 membered heterocycle containing 0-1 additional heteroatoms selected from N, O and S;

R$^{7g}$ is independently selected from —C(O)R$^{7b}$, —C(O)OR$^{7d}$, —C(O)NR$^{7f}$R$^{7f}$, and (CR'R')$_r$phenyl;

R', at each occurrence, is independently, selected from H, methyl, and C$_{2-6}$ alkyl;

R$^8$ is selected from H, C$_{1-4}$ alkyl, and C$_{3-4}$ cycloalkyl;

R$^{10}$ and R$^{10a}$ are independently selected from H and C$_{1-4}$ alkyl substituted with 0-1 R$^{10b}$, alternatively, R$^{10}$ and R$^{10a}$ can join to form a C$_{3-6}$ cycloalkyl;

R$^{10b}$, at each occurrence, is independently selected from —OH, —SH, NR$^{10c}$R$^{10c}$, —C(O)NR$^{10c}$R$^{10c}$, and —NHC(O)R$^{10c}$;

R$^{10c}$ is selected from H, C$_{1-4}$ alkyl and C$_{3-6}$ cycloalkyl;

alternatively, two R$^{10c}$s, together with the N to which they are attached, join to form a 3-8 membered heterocycle containing 0-1 additional heteroatoms selected from N, O and S;

R$^{12}$ is selected from H and C$_{1-4}$ alkyl;

R$^{14}$, at each occurrence, is independently selected from H and C$_{1-4}$alkyl;

alternatively, two R$^{14}$s, along with the carbon atom to which they are attached, join to form a C$_{3-6}$ carbocyclic ring;

R$^{25}$, at each occurrence, is independently selected from H, C$_{1-4}$alkyl, OH, NH$_2$, —O—C$_{1-4}$ alkyl, NR$^{25a}$R$^{25a}$, C(O)NR$^{25a}$R$^{25a}$, NR$^{25a}$C(O)R$^{25b}$, NR$^{25a}$C(O)OR$^{25b}$, OC(O)NR$^{25a}$R$^{25a}$, and (CHR)$_r$C(O)OR$^{25b}$;

alternatively, two R$^{25}$s, along with the carbon atom or atoms to which they are attached, join to form a C$_{3-6}$ carbocyclic ring;

R$^{25a}$, at each occurrence, is independently selected from H, and C$_{1-4}$ alkyl, alternatively, two R$^{25a}$s, together with the N to which they are attached, join to form a 3-8 membered heterocycle containing 0-1 additional heteroatoms selected from N, O and S;

R$^{25b}$, at each occurrence, is independently selected from H, C$_{1-4}$ alkyl, C$_{3-6}$ alkenyl, and C$_{3-6}$ alkynyl;

a is selected from 0 and 1;

b is selected from 0 and 1;

with the proviso that a+b is selected from 1 and 2;

c is selected from 0 and 1;

d is selected from 1 and 2;

with the proviso that c+d is selected from 2 and 3;

n is selected from 1 and 2;

p, at each occurrence, is independently selected from 0, 1, and 2;

q, at each occurrence, is independently selected from 1 and 2;

r, at each occurrence, is independently selected from 0, 1, and 2; and u is selected from 1, 2 and 3.

Some particularly preferred compounds are those in which

X is O;

Z is selected from a bond, —C(O)NR$^8$—, —NR$^8$— and —NR$^8$C(O)—;

R$^1$ is selected from H, R$^6$, and C$_{1-6}$ alkyl substituted with 0-3 R$^6$;

R$^2$ is selected from a C$_{6-10}$ aryl group substituted with 0-5 R$^7$, wherein the aryl group is selected from phenyl and naphthyl, and a 5-10 membered heteroaryl system containing 1-4 heteroatoms selected from N, O, and S, substituted with 0-3 R$^7$, wherein the heteroaryl is selected from indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolinyl, isoxazolyl, oxazolyl, phthalazinyl, pyrazinyl, pyrazolyl, pyrazolotriazinyl, pyridazinyl, pyridyl, pyridinyl, pyrimidinyl, pyrrolyl, quinazolinyl, quinolinyl, thiazolyl, thienyl, and tetrazolyl;

$R^3$ is H;

$R^4$ is absent, taken with the nitrogen to which it is attached to form an N-oxide, or $C_{1-8}$ alkyl;

$R^5$ is selected from H and $C_{1-6}$ alkyl;

$R^6$, at each occurrence, is selected from $C_{1-8}$ alkyl, $(CR'R')_r$$NR^{6a}R^{6a}$, $(CR'R')_r$OH, $(CR'R')_r$O$(CR'R')_r$$R^{6d}$, $(CR'R')_r$C(O)$(CR'R')_r$$R^{6a}$, $(CR'R')_r$C(O)$NR^{6a}R^{6a}$, $(CR'R')_r$$NR^{6f}$C(O)$(CR'R')_r$$R^{6a}$, and $(CR'R')_r$S(O)$_p$$(CR'R')_r$$R^{6a}$;

$R^{6a}$, at each occurrence, is selected from H, methyl, $C_{2-6}$ alkyl substituted with 0-2 $R^{6e}$, $C_{3-8}$ alkenyl substituted with 0-2 $R^{6e}$, $C_{3-8}$ alkynyl substituted with 0-2 $R^{6e}$, a $(CR'R')_r$—$C_{3-10}$ carbocyclic residue substituted with 0-5 $R^{6e}$, and a $(CR'R')_r$-5-10 membered heterocyclic system containing 1-4 heteroatoms selected from N, O, and S, substituted with 0-2 $R^{6e}$;

alternatively, two $R^{6a}$s, together with the N to which they are attached, join to form a 3-8 membered heterocycle containing 0-1 additional heteroatoms selected from N, O and S;

$R^{6d}$, at each occurrence, is selected from methyl and $C_{2-6}$ alkyl substituted with 0-3 $R^{6e}$;

$R^{6e}$, at each occurrence, is selected from $C_{1-6}$ alkyl, Cl, F, $(CF_2)_rCF_3$, and $(CR'R')_rOC_{1-5}$ alkyl;

$R^{6f}$, at each occurrence, is selected from H and $C_{1-5}$ alkyl;

$R^7$, at each occurrence, is selected from $C_{1-8}$ alkyl, Cl, Br, F, CN, $(CR'R')_rNR^{7a}R^{7a}$, $(CR'R')_rOH$, $(CR'R')_rO(CR'R')_rR^{7d}$, $(CR'R')_rC(O)(CR'R')_rR^{7b}$, $(CR'R')_rC(O)NR^{7a}R^{7a}$, $(CR'R')_rNR^{7f}C(O)(CR'R')_rR^{7b}$, $(CR'R')_rOC(O)NR^{7a}(CR'R')_rR^{7a}$, $(CR'R')_rNR^{7a}C(O)NR^{7a}(CR'R')_rR^{7a}$, $(CR'R')_rNR^{7f}C(O)O(CR'R')_rR^{7d}$, $(CR'R')_rS(O)_p(CR'R')_rR^{7b}$, $(CR'R')_rS(O)_2NR^{7a}R^{7a}$, $(CR'R')_rNR^{7f}S(O)_2(CR'R')_rR^{7b}$, $C_{1-6}$ haloalkyl, and a $(CR'R')_r$—$C_{3-10}$ carbocyclic residue substituted with 0-3 $R^{7e}$;

$R^{7a}$, at each occurrence, is independently selected from H, methyl, $C_{2-6}$ alkyl, a $(CR'R')_r$—$C_{3-10}$ carbocyclic residue substituted with 0-5 $R^{7e}$, and a $(CR'R')_r$-5-10 membered heterocyclic system containing 1-4 heteroatoms selected from N, O, and S, substituted with 0-2 $R^{7e}$;

alternatively, two $R^{7a}$s, together with the N to which they are attached, join to form a 3-8 membered heterocycle containing 0-1 additional heteroatoms selected from N, O and S;

$R^{7b}$, at each occurrence, is selected from $C_{1-6}$ alkyl, $C_{3-8}$ alkenyl, a $(CR'R')_rC_{3-6}$ carbocyclic residue substituted with 0-3 $R^{7e}$, and a $(CR'R')_r$-4-6 membered heterocyclic system containing 1-4 heteroatoms selected from N, O, and S, substituted with 0-2 $R^{7e}$;

$R^{7d}$, at each occurrence, is selected from methyl, $C_{2-6}$ alkyl, a $(CR'R')_r$—$C_{3-10}$ carbocyclic residue substituted with 0-3 $R^{7e}$, and a $(CR'R')_r$-5-6 membered heterocyclic system containing 1-4 heteroatoms selected from N, O, and S, substituted with 0-3 $R^{7e}$;

$R^{7e}$, at each occurrence, is selected from $C_{1-6}$ alkyl, $C_{2-8}$ alkenyl, Cl, F, Br, CN, $(CF_2)_rCF_3$, $(CR'R')_rOC_{1-5}$ alkyl, $C(O)OC_{1-5}$ alkyl, $(CR'R')_rNR^{7f}R^{7f}$, and acetyl;

$R^{7f}$, at each occurrence, is selected from H and $C_{1-4}$ alkyl;

R', at each occurrence, is independently, selected from H and methyl;

$R^8$ is H;

$R^{10}$ and $R^{10a}$ are independently selected from H and $C_{1-4}$ alkyl;

$R^{12}$ is H;

$R^{14}$, at each occurrence, is H;

$R^{25}$, at each occurrence, is independently selected from H, OH, and $NH_2$;

a is 1;

b is 0;

c is 1;

d is 1;

n is 1;

p, at each occurrence, is independently selected from 0, 1, and 2;

q, at each occurrence, is 1;

r, at each occurrence, is independently selected from 0 and 1; and u is selected from 1 and 2.

Some more particularly preferred compounds are those in which

X is O;

Z is selected from a bond and —$NR^8$—;

$R^1$ is selected from H, $R^6$, and $C_{1-6}$ alkyl substituted with 0-2 $R^6$;

$R^2$ is a 5-10 membered heteroaryl system containing 1-4 heteroatoms selected from N, O, and S, substituted with 0-3 $R^7$, wherein the heteroaryl is selected from indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolinyl, isoxazolyl, oxazolyl, phthalazinyl, pyrazinyl, pyrazolyl, pyrazolotriazinyl, pyridazinyl, pyridyl, pyridinyl, pyrimidinyl, pyrrolyl, quinazolinyl, quinolinyl, thiazolyl, thienyl, and tetrazolyl;

$R^3$ is H;

$R^4$ is absent, taken with the nitrogen to which it is attached to form an N-oxide, or $C_{1-8}$ alkyl;

$R^5$ is selected from H and $C_{1-6}$ alkyl;

$R^6$, at each occurrence, is selected from $C_{1-4}$ alkyl, $(CH_2)_rNR^{6a}R^{6a}$, $(CH_2)_rOH$, $(CH_2)_rO(CH_2)_rR^{6d}$, $(CH_2)_rC(O)(CH_2)_rR^{6a}$, $(CH_2)_rC(O)NR^{6a}R^{6a}$, $(CH_2)_rNR^{6f}C(O)(CH_2)_rR^{6a}$, and $(CH_2)_rS(O)_p(CH_2)_rR^{6a}$;

$R^{6a}$, at each occurrence, is selected from H, $C_{1-4}$ alkyl, phenyl substituted with 0-3 $R^{6e}$, and a 5-10 membered heterocyclic system containing 1-4 heteroatoms selected from N, O, and S, substituted with 0-2 $R^{6e}$;

alternatively, two $R^{6a}$s, together with the N to which they are attached, join to form a heterocycle wherein the heterocycle is selected from azetidinyl, pyrrolyl, piperidinyl, and morpholinyl;

$R^{6d}$, at each occurrence, is selected from $C_{1-4}$ alkyl;

$R^{6e}$, at each occurrence, is selected from $C_{1-4}$ alkyl, Cl, F, $(CF_2)_rCF_3$, and $(CH_2)_rOC_{1-4}$ alkyl;

$R^{6f}$, at each occurrence, is selected from H, methyl and ethyl;

$R^7$ is selected from $C_{1-6}$ alkyl, phenyl substituted with 0-3 $R^{7e}$, Cl, Br, I, F, CN, $NO_2$, $NR^{7a}R^{7a}$, NHC(O)NHR$^{7a}$, $NR^{7a}C(O)R^{7b}$, $NR^{7a}C(O)OR^{7d}$, $CF_3$, $CF_2CF_3$, $CHF_2$, $CH_2F$, $OCF_3$, $C(O)R^{7b}$, $C(O)OR^{7d}$, NHC(O)NR$^{7a}R^{7a}$, NHS(O)$_2R^{7b}$,

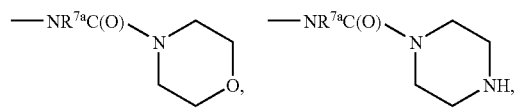

-continued

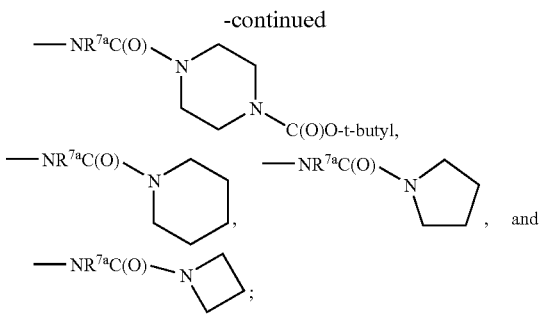

$R^{7a}$, at each occurrence, is independently selected from H and $C_{1-4}$ alkyl;
alternatively, two $R^{7a}$s, together with the N to which they are attached, join to form a heterocycle wherein the heterocycle is selected from azetidinyl, pyrrolyl, piperidinyl, and morpholinyl;
$R^{7b}$, at each occurrence, is selected from $C_{1-6}$ alkyl, a $(CH_2)_rC_{3-6}$ carbocyclic residue substituted with 0-3 $R^{7e}$, and a $(CH_2)_r$-5-6 membered heterocyclic system containing 1-4 heteroatoms selected from N, O, and S, substituted with 0-2 $R^{7e}$;
$R^{7d}$, at each occurrence, is selected from $C_{1-6}$ alkyl, a $(CH_2)_r$—$C_{3-6}$ carbocyclic residue substituted with 0-3 $R^{7e}$, and a $(CH_2)_r$-5-6 membered heterocyclic system containing 1-4 heteroatoms selected from N, O, and S, substituted with 0-2 $R^{7e}$;
$R^{7e}$, at each occurrence, is selected from $C_{1-6}$ alkyl, Cl, F, Br, CN, $(CF_2)_rCF_3$, $(CH_2)_rOC_{1-4}$ alkyl, $C(O)OC_{1-4}$ alkyl, $(CH_2)_rNR^{7f}R^{7f}$, and acetyl;
$R^{7f}$, at each occurrence, is selected from H, and $C_{1-4}$ alkyl;
$R^8$ is H;
$R^{10}$ and $R^{10a}$ are independently selected from H and $C_{1-4}$ alkyl;
$R^{12}$ is H;
$R^{14}$, at each occurrence, is H;
a is 1;
b is 0;
c is 1;
d is 1;
n is 1;
p, at each occurrence, is independently selected from 0, 1, and 2; and
r, at each occurrence, is independently selected from 0 and 1.

Some additional more particularly preferred compounds are those in which
X is 0;
Z is selected from —C(O)NR$^8$— and —NR$^8$C(O)—;
$R^1$ is selected from H, $R^6$, and $C_{1-6}$ alkyl substituted with 0-2 $R^6$;
$R^2$ is selected from a $C_{6-10}$ aryl group substituted with 0-3 $R^7$, wherein the aryl group is selected from phenyl and naphthyl, and a 5-10 membered heteroaryl system containing 1-4 heteroatoms selected from N, O, and S, substituted with 0-3 $R^7$, wherein the heteroaryl is selected from indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolinyl, isoxazolyl, oxazolyl, phthalazinyl, pyrazinyl, pyrazolyl, pyrazolotriazinyl, pyridazinyl, pyridyl, pyridinyl, pyrimidinyl, pyrrolyl, quinazolinyl, quinolinyl, thiazolyl, thienyl, and tetrazolyl;
$R^3$ is H;
$R^4$ is absent, taken with the nitrogen to which it is attached to form an N-oxide, or $C_{1-8}$ alkyl;
$R^5$ is selected from H and $C_{1-6}$ alkyl;
$R^6$, at each occurrence, is selected from $C_{1-4}$ alkyl, $(CH_2)_r NR^{6a}R^{6a}$, $(CH_2)_rOH$, $(CH_2)_rO(CH_2)_rR^{6d}$, $(CH_2)_rC(O)(CH_2)_rR^{6a}$, $(CH_2)_rC(O)NR^{6a}R^{6a}$, $(CH_2)_rNR^{6f}C(O)(CH_2)_r$ $R^{6a}$, and $(CH_2)_rS(O)_p(CH_2)_rR^{6a}$;
$R^{6a}$, at each occurrence, is selected from H, $C_{1-4}$ alkyl, phenyl substituted with 0-3 $R^{6e}$, and a 5-10 membered heterocyclic system containing 1-4 heteroatoms selected from N, O, and S, substituted with 0-2 $R^{6e}$;
alternatively, two $R^{6a}$s, together with the N to which they are attached, join to form a heterocycle wherein the heterocycle is selected from azetidinyl, pyrrolyl, piperidinyl, and morpholinyl;
$R^{6d}$, at each occurrence, is selected from $C_{1-4}$ alkyl;
$R^{6e}$, at each occurrence, is selected from $C_{1-4}$ alkyl, Cl, F, $(CF_2)_rCF_3$, and $(CH_2)_rOC_{1-4}$ alkyl;
$R^{6f}$, at each occurrence, is selected from H, methyl and ethyl;
$R^7$ is selected from $C_{1-6}$ alkyl, phenyl substituted with 0-3 $R^{7e}$, Cl, Br, I, F, CN, $NO_2$, $NR^{7a}R^{7a}$, $NHC(O)NHR^{7a}$, $NR^{7a}C(O)R^{7b}$, $NR^{7a}C(O)OR^{7d}$, $CF_3$, $CF_2CF_3$, $CHF_2$, $CH_2F$, $OCF_3$, $C(O)R^{7b}$, $C(O)OR^{7d}$, $NHC(O)NR^{7a}R^{7a}$, $NHS(O)_2R^{7b}$,

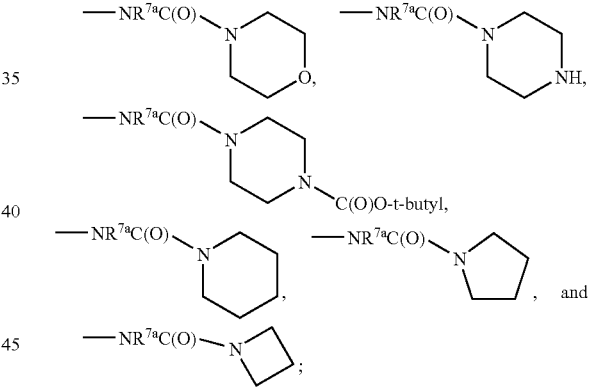

$R^{7a}$, at each occurrence, is independently selected from H and $C_{1-4}$ alkyl;
alternatively, two $R^{7a}$s, together with the N to which they are attached, join to form a heterocycle wherein the heterocycle is selected from azetidinyl, pyrrolyl, piperidinyl, and morpholinyl;
$R^{7b}$, at each occurrence, is selected from $C_{1-6}$ alkyl, a $(CH_2)_rC_{3-6}$ carbocyclic residue substituted with 0-3 $R^{7e}$, and a $(CH_2)_r$-5-6 membered heterocyclic system containing 1-4 heteroatoms selected from N, O, and S, substituted with 0-2 $R^{7e}$;
$R^{7d}$, at each occurrence, is selected from $C_{1-6}$ alkyl, a $(CH_2)_r$—$C_{3-6}$ carbocyclic residue substituted with 0-3 $R^{7e}$, and a $(CH_2)_r$-5-6 membered heterocyclic system containing 1-4 heteroatoms selected from N, O, and S, substituted with 0-2 $R^{7e}$;
$R^{7e}$, at each occurrence, is selected from $C_{1-6}$ alkyl, Cl, F, Br, CN, $(CF_2)_rCF_3$, $(CH_2)_rOC_{1-4}$ alkyl, $C(O)OC_{1-4}$ alkyl, $(CH_2)_rNR^{7f}R^{7f}$, and acetyl;

$R^{7f}$, at each occurrence, is selected from H, and $C_{1-4}$ alkyl;
$R^8$ is H;
$R^{10}$ and $R^{10a}$ are independently selected from H and $C_{1-4}$ alkyl;
$R^{12}$ is H;
$R^{14}$, at each occurrence, is H;
a is 1;
b is 0;
c is 1;
d is 1;
n is 1;
p, at each occurrence, is independently selected from 0, 1, and 2; and
r, at each occurrence, is independently selected from 0 and 1.

In another embodiment, the present invention is directed to a pharmaceutical composition, comprising a pharmaceutically acceptable carrier and a therapeutically effective amount of a compound of Formula (I). The preferred, particularly preferred, more particularly preferred, and even more particularly preferred compounds set forth above can be used in this embodiment.

In another embodiment, the present invention is directed to a method for modulation of chemokine or chemokine receptor activity comprising administering to a patient in need thereof a therapeutically effective amount of a compound of Formula (I). The preferred, particularly preferred, more particularly preferred, and even more particularly preferred compounds set forth above can be used in this embodiment.

In another embodiment, the present invention is directed to a method for modulation of CCR-2 receptor activity comprising administering to a patient in need thereof a therapeutically effective amount of a compound of Formula (I). The preferred, particularly preferred, more particularly preferred, and even more particularly preferred compounds set forth above can be used in this embodiment.

In another embodiment, the present invention is directed to a method for modulation of MCP-1, MCP-2, MCP-3 and MCP-4, and MCP-5 activity, preferably modulation of MCP-1 activity, that is mediated by the CCR2 receptor comprising administering to a patient in need thereof a therapeutically effective amount of a compound of Formula (I). The preferred, particularly preferred, more particularly preferred, and even more particularly preferred compounds set forth above can be used in this embodiment.

In another embodiment, the present invention is directed to a method for treating disorders, comprising administering to a patient in need thereof a therapeutically effective amount of a compound of Formula (I), said disorders being selected from osteoarthritis, aneurysm, fever, cardiovascular effects, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerularnephritis, asthma, multiple sclerosis, artherosclerosis, rheumatoid arthritis, restinosis, organ transplantation, and cancer; preferably, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerularnephritis, asthma, multiple sclerosis, artherosclerosis, and rheumatoid arthritis, restinosis, organ transplantation, and cancer; more preferably, alveolitis, colitis, systemic lupus erythematosus, nephrotoxic serum nephritis, glomerularnephritis, asthma, multiple sclerosis, artherosclerosis, and rheumatoid arthritis, restinosis, organ transplantation, and cancer; most preferably asthma, multiple sclerosis, artherosclerosis, rheumatoid arthritis, restinosis, organ transplantation, and cancer. The preferred, particularly preferred, more particularly preferred, and even more particularly preferred compounds set forth above can be used in this embodiment.

In another embodiment, the present invention is directed to a method for treating inflammatory diseases, preferably, inflammatory diseases which are at least partially mediated by CCR-2, comprising administering to a patient in need thereof a therapeutically effective amount of a compound of Formula (I). The preferred, particularly preferred, more particularly preferred, and even more particularly preferred compounds set forth above can be used in this embodiment.

In another embodiment, the present invention is directed to a method for modulation of CCR2 activity comprising administering to a patient in need thereof a therapeutically effective amount of a compound of Formula (I). The preferred, particularly preferred, more particularly preferred, and even more particularly preferred compounds set forth above can be used in this embodiment.

In another embodiment, the present invention is directed the use of a compound of Formula (I) in the preparation of a medicament for the treatment of osteoarthritis, aneurysm, fever, cardiovascular effects, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerularnephritis, asthma, multiple sclerosis, artherosclerosis, and rheumatoid arthritis. The preferred, particularly preferred, more particularly preferred, and even more particularly preferred compounds set forth above can be used in this embodiment.

In another embodiment, the present invention is directed to a compound of formula (I) for use in therapy.

The preferred, particularly preferred, more particularly preferred, and even more particularly preferred compounds set forth above can be used in this embodiment.

In another embodiment, the present invention is directed to a pharmaceutical composition comprising a compound of formula (I)

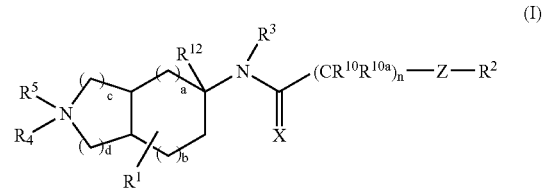

or stereoisomers or pharmaceutically acceptable salts thereof, wherein X, Z, a, b, c, d, n, $R^1$, $R^2$, $R^3$, $R^4$, $R^5$, $R^{10}$, $R^{10a}$, and $R^{12}$, are as defined above, and one or more active ingredients. The preferred, particularly preferred, more particularly preferred, and even more particularly preferred compounds set forth above can be used in this embodiment.

In another embodiment, the present invention is directed to a method for modulation of chemokine or chemokine receptor activity comprising administering to a patient in need thereof a therapeutically effective amount of a pharmaceutical composition comprised of a compound of Formula (I) and one or more active ingredients. The preferred, particularly preferred, more particularly preferred, and even more particularly preferred compounds set forth above can be used in this embodiment.

In another embodiment, the present invention is directed to a method for modulation of CCR-2 receptor activity comprising administering to a patient in need thereof a therapeutically effective amount of a pharmaceutical composition comprised of a compound of Formula (I) and one or more active ingredients. The preferred, particularly preferred, more particularly preferred, and even more particularly preferred compounds set forth above can be used in this embodiment.

In yet another embodiment, the present invention is directed to a method for modulation of MCP-1, MCP-2, MCP-3 and MCP-4, and MCP-5 activity, preferably, modulation of MCP-1 activity, that is mediated by the CCR2 receptor comprising administering to a patient in need thereof a therapeutically effective amount of a pharmaceutical composition comprised of a compound of Formula (I) and one or more active ingredients. The preferred, particularly preferred, more particularly preferred, and even more particularly preferred compounds set forth above can be used in this embodiment.

In another embodiment, the present invention is directed to a method for treating a disorder, comprising administering to a patient in need thereof a therapeutically effective amount of a pharmaceutical composition comprised of a compound of Formula (I) and one or more active ingredients, wherein said disorder is selected from osteoarthritis, aneurysm, fever, cardiovascular effects, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerularnephritis, asthma, multiple sclerosis, artherosclerosis, rheumatoid arthritis, restinosis, organ transplantation, and cancer; preferably, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerularnephritis, asthma, multiple sclerosis, artherosclerosis, and rheumatoid arthritis, restinosis, organ transplantation, and cancer; more preferably, alveolitis, colitis, systemic lupus erythematosus, nephrotoxic serum nephritis, glomerularnephritis, asthma, multiple sclerosis, artherosclerosis, and rheumatoid arthritis, restinosis, organ transplantation, and cancer; and most preferably, asthma, multiple sclerosis, artherosclerosis, rheumatoid arthritis; restinosis, organ transplantation, and cancer. The preferred, particularly preferred, more particularly preferred, and even more particularly preferred compounds set forth above can be used in this embodiment.

In yet another embodiment, the present invention, is directed to a method for treating inflammatory diseases, preferably, inflammatory diseases which are at least partially mediated by CCR-2, comprising administering to a patient in need thereof a therapeutically effective amount of a pharmaceutical composition comprised of a compound of Formula (I) and one or more active ingredients. The preferred, particularly preferred, more particularly preferred, and even more particularly preferred compounds set forth above can be used in this embodiment.

In another embodiment, the present invention is directed to a method for modulation of CCR2 activity comprising administering to a patient in need thereof a therapeutically effective amount of a pharmaceutical composition comprised of a compound of Formula (I) and one or more active ingredients. The preferred, particularly preferred, more particularly preferred, and even more particularly preferred compounds set forth above can be used in this embodiment.

In another embodiment, the present invention is directed to the use of a pharmaceutical composition comprised of a compound of Formula (I) and one or more active ingredients in the preparation of a medicament for the treatment of osteoarthritis, aneurysm, fever, cardiovascular effects, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerularnephritis, asthma, multiple sclerosis, artherosclerosis, and rheumatoid arthritis. The preferred, particularly preferred, more particularly preferred, and even more particularly preferred compounds set forth above can be used in this embodiment.

In still yet another embodiment, the present invention is directed to the use of a pharmaceutical composition comprised of a compound of Formula (I) and one or more active ingredients in therapy. The preferred, particularly preferred, more particularly preferred, and even more particularly preferred compounds set forth above can be used in this embodiment.

The invention may be embodied in other specific forms without departing from the spirit or essential attributes thereof. This invention also encompasses all combinations of alternative aspects of the invention noted herein. It is understood that any and all embodiments of the present invention may be taken in conjunction with any other embodiment to describe additional embodiments of the present invention. Furthermore, any elements of an embodiment may be combined with any and all other elements from any of the embodiments to describe additional embodiments.

Definitions

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

One enantiomer of a compound of Formula I may display superior activity compared with the other. Thus, all of the stereochemistries are considered to be a part of the present invention. When required, separation of the racemic material can be achieved by HPLC using a chiral column or by a resolution using a resolving agent such as camphonic chloride as in Steven D. Young, et al, *Antimicrobial Agents and Chemotheraphy*, 1995, 2602-2605.

The term "substituted," as used herein, means that any one or more hydrogens on the designated atom or ring is replaced with a selection from the indicated group, provided that the designated atom's or ring atom's normal valency is not exceeded, and that the substitution results in a stable compound. When a substitent is keto (i.e., =O), then 2 hydrogens on the atom are replaced.

When any variable (e.g., $R^{10}$) occurs more than one time in any constituent or formula for a compound, its definition at each occurrence is independent of its definition at every other occurrence. Thus, for example, if a group is shown to be substituted with 0-2 $R^{10}$, then said group may optionally be substituted with up to two $R^{10}$ groups and $R^{10}$ at each occurrence is selected independently from the definition of $R^{10}$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "$C_{1-8}$ alkyl" is intended to include both branched and straight-chain saturated aliphatic hydrocarbon groups having the specified number of carbon atoms, examples of which include, but are not limited to, methyl, ethyl, n-propyl, i-propyl, n-butyl, i-butyl, sec-butyl, t-butyl, pentyl, and hexyl. $C_{1-8}$ alkyl, is intended to include $C_1$, $C_2$, $C_3$, $C_4$, $C_5$, $C_6$, $C_7$, and $C_8$ alkyl groups. "Alkenyl" is intended to include hydrocarbon chains of either a straight or branched configuration and one or more unsaturated carbon-carbon bonds which may occur in any stable point along the chain, such as ethenyl, propenyl, and the like. "Alkynyl" is intended to include hydrocarbon chains of either a straight or branched configuration and one or more unsaturated triple carbon-carbon bonds which may occur in any stable point along the chain, such as ethynyl, propynyl, and the like. "$C_{3-6}$ cycloalkyl" is intended to include saturated ring groups having the specified number of carbon atoms in the ring, including mono-, bi-, or poly-cyclic ring systems, such as cyclopropyl, cyclobutyl, cyclopentyl, cyclohexyl, and cycloheptyl in the case of $C_7$ cycloalkyl. $C_{3-6}$ cycloalkyl, is intended to include $C_3$, $C_4$, $C_5$, and $C_6$ cycloalkyl groups "Halo" or "halogen" as used herein refers to fluoro, chloro, bromo, and iodo; and "haloalkyl" is intended to include both branched and straight-chain saturated aliphatic hydrocarbon groups, for example $CF_3$, having the specified number of carbon atoms, substituted with 1 or more halogen (for example —$C_vF_w$ where v=1 to 3 and w=1 to (2v+1)).

As used herein, the term "5-6-membered cyclic ketal" is intended to mean 2,2-disubstituted 1,3-dioxolane or 2,2-disubstituted 1,3-dioxane and their derivatives.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin).

As used herein, the term "heterocycle" or "heterocyclic system" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom, which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. As used herein, the term "aromatic heterocyclic system" or "heteroaryl" is intended to mean a stable 5- to 7-membered monocyclic or bicyclic or 7- to 10-membered bicyclic heterocyclic aromatic ring which consists of carbon atoms and from 1 to 4 heterotams independently selected from the group consisting of N, O and S and is aromatic in nature.

Examples of heterocycles include, but are not limited to, 1H-indazole, 2-pyrrolidonyl, 2H,6H-1,5,2-dithiazinyl, 2H-pyrrolyl, 1H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, indazolyl, indolenyl, indolinyl, indolizinyl, indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. In another aspect of the invention, the heterocycles include, but are not limited to, pyridinyl, thiophenyl, furanyl, indazolyl, benzothiazolyl, benzimidazolyl, benzothiaphenyl, benzofuranyl, benzoxazolyl, benzisoxazolyl, quinolinyl, isoquinolinyl, imidazolyl, indolyl, isoidolyl, piperidinyl, piperidonyl, 4-piperidonyl, piperonyl, pyrrazolyl, 1,2,4-triazolyl, 1,2,3-triazolyl, tetrazolyl, thiazolyl, oxazolyl, pyrazinyl, and pyrimidinyl. Also included are fused ring and spiro compounds containing, for example, the above heterocycles.

Examples of heteroaryls are 1H-indazole, 2H,6H-1,5,2-dithiazinyl, indolyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, indazolyl, indolenyl, indolinyl, indolizinyl, indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyrazolotriazinyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. In another aspect of the invention, examples of heteroaryls are indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, pyrazinyl, pyrazolyl, pyrazolotriazinyl, pyridazinyl, pyridyl, pyridinyl, pyrimidinyl, pyrrolyl, quinazolinyl, quinolinyl, thiazolyl, thienyl, and tetrazolyl.

As used herein, the term "cyclic acetal" or or the phrase when two variables "join to form a cyclic acetal" is intended to mean the substituent —O—CH$_2$—O—.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers which release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

In addition, compounds of the formula I are, subsequent to their preparation, preferably isolated and purified to obtain a composition containing an amount by weight equal to or greater than 99% formula I compound ("substantially pure" compound I), which is then used or formulated as described herein. Such "substantially pure" compounds of the formula I are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to inhibit MCP-1 or effective to treat or prevent inflammatory disorders.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Third Edition, Wiley and Sons, 1999).

Chemokine antagonists can be derived from compounds of formula 1.1, as shown in Schemes 1 and 2. Thus, compounds of formula 1.3 can be derived from compounds of formula 1.1 through coupling to acids of formula 1.2. Likewise, compounds of formula 1.5 are available through initial alkylation of 1.1 to 1.4 and subsequent coupling with acids of formula 1.2.

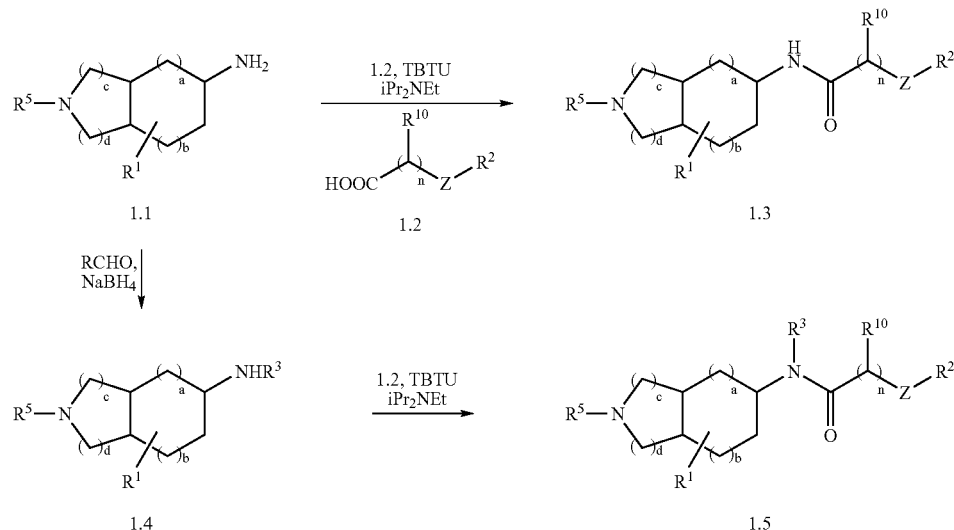

Scheme 1

Other compounds of formula 1.3 can be synthesized using alternative methods, as shown in Scheme 2 (see 2.4, 2.5, and 2.6, all of which are variants of formula 1.3). Thus, coupling of the amine 1.1 with protected amino acid 2.1 affords amide 2.2. This can be deprotected to form amine 2.3, which is easily, derivatized through reaction of an isocyanate to give urea 2.4. Alternatively, amine 2.3 can be arylated (see D. Zim & S. L. Buchwald, *Organic Letters*, 2003, 5, 2413 and T. Wang, D. R. Magnia, & L. G. Hamann, ibid, 897, and references cited therein) to give compound 2.5. Alternatively, amine 2.3 can be arylated with iminoyl chlorides to give 2.6. One skilled in the art would realize that an $R^3$ group could be incorporated into compounds of formulas 2.4, 2.5, and 2.6 simply by starting with compound 1.4. Likewise, one skilled in the art would realize that an $R^8$ group could be incorporated into compounds of formulas 2.4, 2.5, and 2.6 simply by starting with an appropriately N-alkylated, N-protected amino acid.

Scheme 2

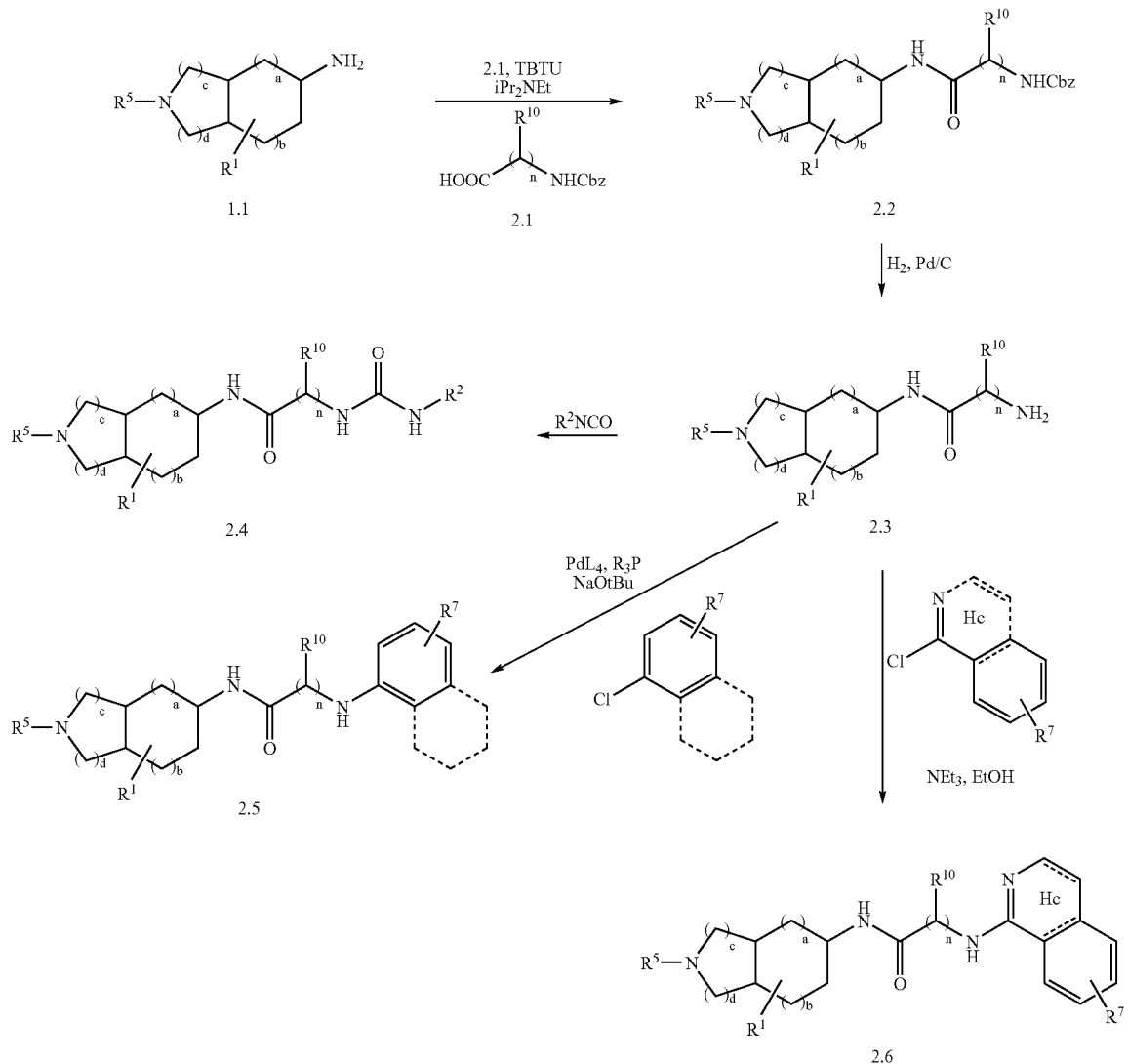

Based on the chemistry described in Schemes 1 and 2, the synthesis of the compounds of this invention can be simplified to the synthesis of compounds of formula 1.1, together with the synthesis of compounds of formula 1.2. The synthesis of the reagents shown in Scheme 2 (i.e. reagents other than 1.2 that can derivatize 1.1) is generally not necessary (given commercial availability) or is readily achieved through chemistry well known to one skilled in the art.

A variety of compounds of formula 1.2 are commercially available, or are derived readily from commercially available materials. Other derivatives of formula 1.2 may be synthesized as shown in Scheme 3 (see 3.3, 3.6, and 3.8, all of which are equivalent to compounds of formula 1.2). Thus, compounds of formula 3.1 are readily converted into a wide variety of compounds of formula 3.3 (see also P. H. Carter and R. J. Cherney, WO 02/50019, 2002, which is hereby incorporated by reference). A series of malonamide variants of formula 1.2 (such as 3.6) are synthesized from commercially available malonic acid mono-esters 3.4, which can be coupled to commercially available amines to provide the malonamides 3.5; deprotection (hydrolysis with lithium hydroxide (LiOH) or potassium hydroxide (KOH); or hydrogenolysis with palladium on carbon (Pd/C) and hydrogen ($H_2$) affords the carboxylates 3.6. A series of heterocyclic variants of 1.2 (such as 3.8) are also synthesized from malonic acid monoesters 3.4. Coupling to mixed anilines 3.9 affords the amides 3.7. These amides (where X=OH, SH, $NH_2$, $NHR^{5a}$) can be cyclized (Takeuchi et al., *Bioorg. Med. Chem. Lett.*, 2000, 2347; Nawwar et al., *Collect. Czech. Chem. Commun.*, 1995, 2200; Hisano et al., *Chem. Pharm. Bull.*, 1982, 2996) and then deprotected (hydrolysis with LiOH or KOH; or hydrogenolysis with Pd/C and $H_2$) to give compounds of formula 3.8. Compounds of formula 3.8 can also be made directly through the condensation of acids 3.4 and bifunctionalized anilines 3.9 (Trapani et al., *Eur. J. Med. Chem.*, 1992, 39; Baudet et al., *Helv. Chim. Acta.*, 1970, 1683; McKinnon et al., *Can J. Chem.*, 1988, 2339; Nivalkar et al., *Synth. Commun.*, 1996, 3535), followed by appropriate ester deprotection.

Scheme 3.

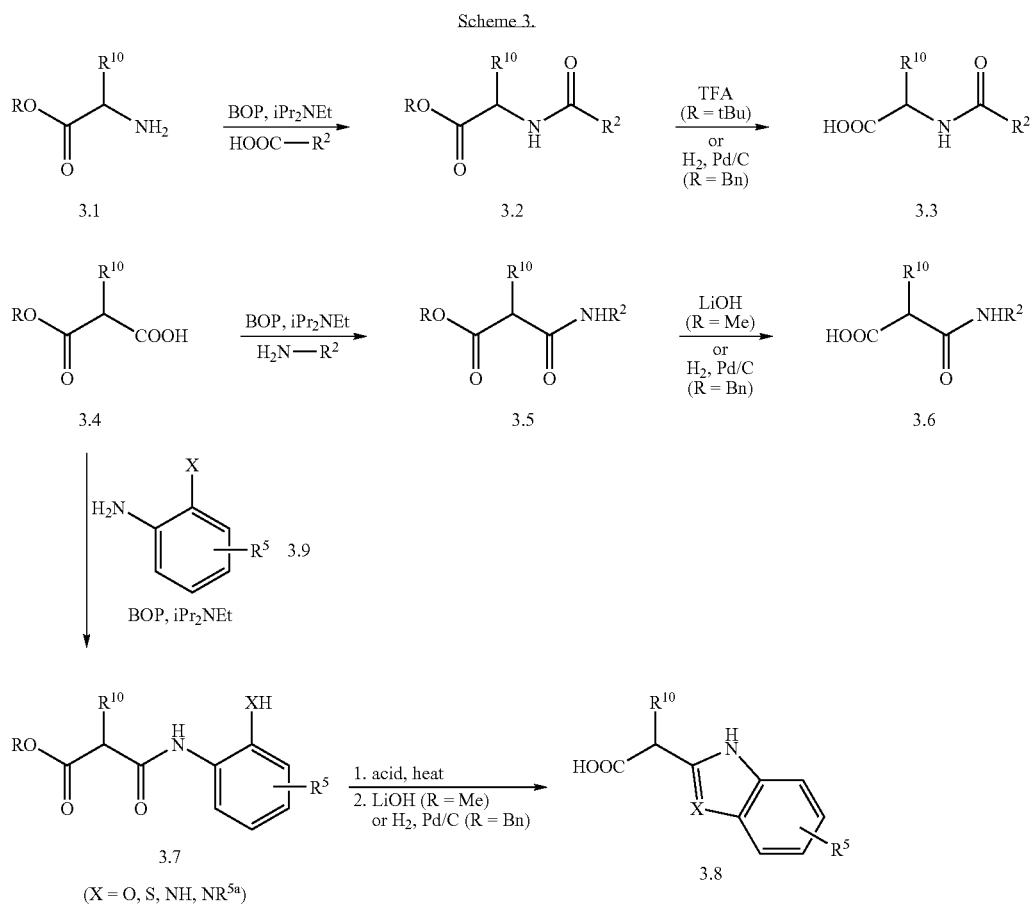

(X = O, S, NH, NR$^{5a}$)

Although amines of formula 1.1 are shown as unprotected amines, they may be synthesized with the amine in protected form. Also, although amines of formula 1.1 are shown with the cyclic amine bearing a substituent R$^5$, they may be synthesized with R$^5$ replaced with an appropriate protecting group, in which case removal of the protecting group and introduction of R$^5$ in a subsequent step can be achieved, requiring only minor adjustments to the chemistry of Schemes 1 and 2.

The bicyclic diamines 1.1 and protected forms thereof can be prepared using a variety of methods, such as those described in Schemes 4 and 6 (wherein P denotes either an appropriate amine protecting group, or a group R$^5$). One method, shown in Scheme 4, involves conversion of a carboxylic acid (R=OH), acid chloride (R=Cl) or mixed anhydride (R=OC(=O)-alkyl or OC(=O)O-alkyl) 4.1 into an acyl azide 4.2, followed by thermal rearrangement to the isocyanate 4.3, commonly referred to as the Curtius rearrangement. Treatment of the intermediate isocyanate with water can provide the amine 4.4 (a protected variant of 1.1) directly. Alternatively, treatment of the intermediate isocyanate with an alcohol such as benzyl alcohol can provide the carbamate 4.5, which can be deprotected to provide 4.4. Some examples of the use of the Curtius rearrangement to effect transformations analogous to those shown in Scheme 4 have been reported by J. Altman and D. Ben-Ishai, *Tetrahedron Asymmetry*, 1994, 5,887; K. Ninomiya, T. Shioiri and S. Yamada, *Tetrahedron*, 1974, 30, 2151; L. M. Gustavson and A. Srinivasan, *Synth. Commun.*, 1991, 21, 265; R. Pires and K. Burger, *Synthesis*, 1996, 1277; and E. Neufellner, H. Kapeller and H. Griengl, *Tetrahedron* 1998, 54, 11043.

A related method for achieving the transformation of a carboxylic acid derivative to an amine as shown in Scheme 4 involves treatment of an amide 4.1 (R=NH$_2$) with an oxidizing agent such as sodium hypobromite or I,I-bis-(trifluoroacetoxy)iodobenzene to provide the amine 4.4, a reaction commonly referred to as the Hofmann rearrangement. This transformation is reviewed by Wallis and Lane, *Org. Reactions*, 1946, 3, 267; and a more recent example was reported by Radhakrishna et al., *J. Org. Chem.*, 1979, 44, 1746.

Scheme 4

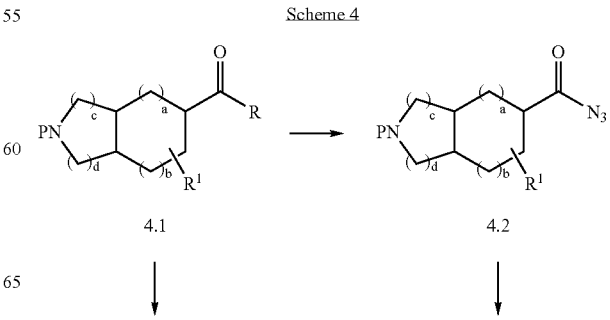

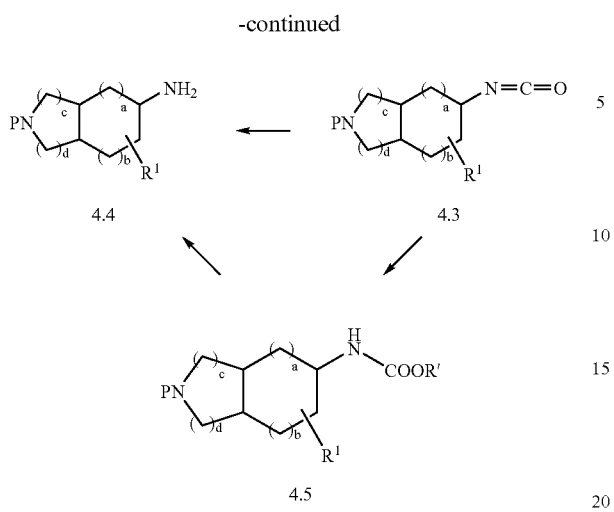

The carboxylic acids and derivatives 4.1 can be prepared using methods well known in the art of organic synthesis. For example, as shown in Scheme 5, a carboxylate ester 5.2 can be prepared by the Diels-Alder reaction of a 3-vinyl-1,4,5,6-tetrahydropyridine 5.1 with an acrylate ester, as reported by C. Ludwig and L. G. Wistrand, *Acta Chem. Scand.*, 1989, 43, 676. Also shown in Scheme 5 is another example, involving the intramolecular Diels-Alder reaction of 5.3 to provide the ester 5.4, as reported by S. Wattarasin, F. G. Kathawala and R. K. Boeckman, *J. Org. Chem.*, 1985, 50, 3810.

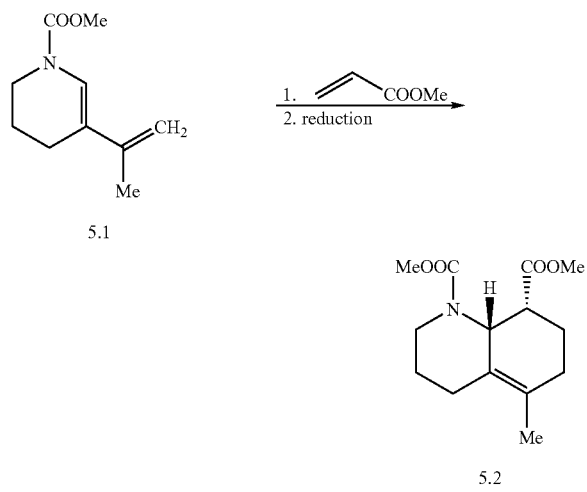

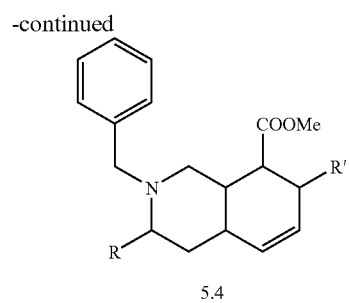

Another method for the preparation of bicyclic diamines 1.1 and protected forms thereof, as shown in Scheme 6, is by conversion of a ketone such as 6.1 to the oxime or substituted oxime (X'=OH or O-benzyl, for example) or imine (X'=$R^3$) 6.2 followed by reduction to an amine 6.3 ($R^{12}$=H) using a reducing agent such as lithium aluminum hydride or borane, as shown in Scheme 5. Alternatively, the oxime or substituted oxime or imine 6.2 can be treated with an organometallic reagent such as $R^{12}$ Li or $R^2$ MgBr, followed by reductive cleavage of the N—O bond in the cases of oximes or substituted oximes, to provide amines 6.3. (In the cases of oximes and substituted oximes, the $R^3$ of 6.3 will be H.) This type of transformation is well known in the literature of organic chemistry. References to some examples are given in R. C. Larock, *Comprehensive Organic Transformations*, VCH, 1989.

Ketones 6.1 can also be converted to amines by reductive amination, using well-known procedures, to provide amines 6.3 ($R^{12}$=H).

Alternatively, ketones 6.1 can be converted to alcohols 6.4 by reduction using reagents such as sodium borohydride or lithium aluminum hydride. The alcohols 6.4 can be converted to the primary amines 6.3 ($R^3$=H, $R^{12}$=H) using several methods, for instance by conversion of the hydroxyl group to a leaving group such as methanesulfonate, trifluoromethanesulfonate or p-toluenesulfonate; displacement of the leaving group with an appropriate nucleophile such as azide anion; and reduction of the resulting azide to an amine using, for example, a method such as catalytic hydrogenation or reduction with triphenylphosphine followed by hydrolysis of the intermediate iminophosphorane with water. Examples of these transformations can be found in Hilpert et al., *J. Med. Chem.*, 1994, 37, 3889; Lebarbier et al., *Synthesis*, 1996, 1371; and Rubiralta et al., *Synth. Commun.*, 1992, 22, 359. The alcohols 6.4 can also be converted directly to the corresponding azides with reagents such as hydrazoic acid or diphenylphosphoryl azide in the presence of a dialkyl azodicarboxylate and triphenylphosphine, for example, as described in Lal et al., *Tetrahedron Lett.*, 1977, 1977; or Hiebl et al., *J. Med. Chem.*, 1991, 34, 1426.

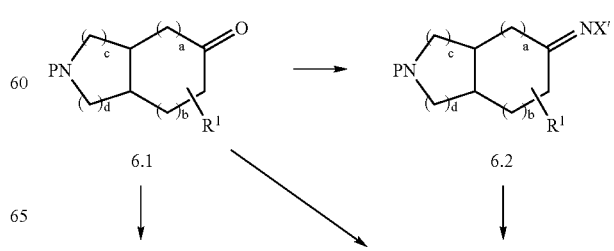

-continued

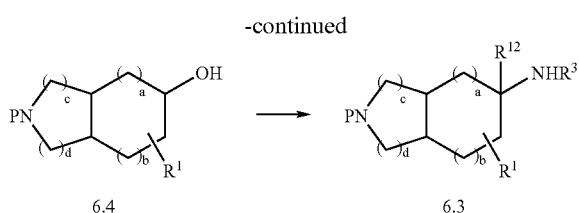

Ketones 6.1 may be prepared using a wide variety of synthetic methods as reported in the literature of organic chemistry. For example, the carboxylic acids 4.1 (R=OH) shown in Scheme 4 may be converted to the corresponding ketones 6.1 using the oxidative decarboxylation method reported by H. Wasserman and B. H. Lipshutz, *Tetrahedron Lett.*, 1975, 4611. Numerous other methods have been reported for preparation of the bicyclic ring systems corresponding to the ketones 6.1, with various substitution on the rings and various protecting groups or substitution on the ring nitrogen. In some cases, the reported methods can directly yield the desired ketones 6.1. In other cases, minor modifications of the reported methods, which will be obvious to one skilled in the art of organic synthesis, can yield the desired ketones 6.1. In still other cases, simple synthetic transformations of the reported products, obvious to one skilled in the art, can yield the desired ketones 6.1. Some examples of such methods are listed below.

Ketones 6.1 (a=0; b=0, 1, or 2; c=0; d=3) can be prepared by cyclization of a 2-(3-aminopropyl)-cyclopentanone derivative followed by hydroboration and oxidation (L. E. Overman, G. M. Robertson, and A. J. Robichaud, *J. Amer. Chem. Soc.*, 1991, 113, 2598; Overman et al., *Tetrahedron*, 1981, 37, 4041) or by cyclization of a 2-cyano-3-(2-alkoxycarbonylethyl)-piperidine derivative followed by acid hydrolysis and decarboxylation (C. H. Heathcock, M. H. Norman and D. A. Dickman, *J. Org. Chem.*, 1990, 55, 798). Ketones 6.1 (a=0; b=1, 2 or 3; c=1; d=1) can be prepared by reaction of an iminiumylide with a 2-cycloalkenone (Eur. Pat. Appl. 0 359 172 A1; M. Ogata et al., *Eur. J. Med. Chem.*, 1991, 26, 889; Tsuge et al., *Bull. Chem. Soc. Japan*, 1987, 60, 4079; K. Miyajima, M. Takemoto and K. Achiwa, *Chem. Pharm. Bull.*, 1991, 39, 3175). Ketones 6.1 (a=0; b=1; c=1; d=2) can be prepared by hydroboration of a 4-vinyl-1,2,5,6-tetrahydropyridine derivative, followed by reaction with potassium cyanide and oxidation (Ogata et al., *Eur. J. Med. Chem.*, 1991, 26, 889).

Ketones 6.1 (a=0; b=2; c=1; d=2) can be prepared by reduction of an 8-nitroisoquinoline derivative followed by subsequent synthetic manipulations (I. W. Mathison and P. H. Morgan, *J. Org. Chem.*, 1974, 39, 3210). Ketones 6.1 (a=0; b=1, 2 or 3; c=0; d=2) can be prepared by cyclization of an N-bromo-3-(2-aminoethyl)-cycloalkene derivative (E. J. Corey, C. P. Chen and G. A. Reichard, *Tetrahedron Lett.*, 1989, 30, 5547) or iodine-induced cyclization of a cycloalken-3-ylacetamide derivative (S. Knapp and A. T. Levorse, *J. Org. Chem.*, 1988, 53, 4006) followed by subsequent synthetic manipulations, or by radical cyclization of a 2,2-dichloro-N-(1-oxocycloalk-2-en-2-yl)acetamide, followed by subsequent synthetic manipulations (A. F. Parsons and D. A. J. Williams, *Tetrahedron*, 2000, 56, 7217).

Ketones 6.1 (a=1; b=0; c=1; d=2) can be prepared by the intramolecular Pauson-Khand reaction of an appropriately substituted 4-aza- or 5-aza-oct-1-ene-7-yne derivative (G. L. Bolton, J. C. Hodges and J. R. Rubin, *Tetrahedron*, 1997, 53, 6611; Pagenkopf et al., *Synthesis*, 2000, 1009), or by the Schmidt reaction of tetrahydropentalene-2,5(1H, 3H)-dione (Vidau et al., *Tetrahedron Asymm.*, 1997, 8, 2893; and Gracias et al., *Tetrahedron*, 1997, 53, 16241) followed by subsequent synthetic manipulations. Ketones 6.1 (a=1; b=1; c=1; d=2) can be prepared by the ring-closing metathesis reaction of a 3,4-diallylpiperidine derivative followed by hydroxylation of the resulting 1,2,3,4,4a,5,8,8a-octahydroisoquinoline (S. Liras, M. P. Allen and J. F. Blake, *Org. Lett.*, 2001, 3, 3483).

Ketones 6.1 (a=1; b=0; c=0; d=2) can be prepared by Dieckmann cyclization of an appropriate dialkyl 2,2'-pyrrolidine-2,3-diyldiacetate derivative (C. L. J. Wang, *Tetrahedron Lett.*, 1983, 24, 477) or by cyclization of the acyliminium ion derived from an appropriate 3-{2-[(trialkylsilyl)methyl]prop-2-en-1-yl}pyrrolidin-2-one derivative (J. C. Gramain and P. Remuson, *Heterocycles*, 1989, 29, 1263). Ketones 6.1 (a=1; b=1; c=0; d=2 or 3) can be prepared by dissolving metal reduction of an appropriate 4-alkoxyphenethylamine or 4-alkoxyphenpropylamine derivative, followed by hydrolysis and cyclization (Bonjoch et al., *Tetrahedron Asymm.*, 1997, 8, 3143; U.S. Pat. No. 4,600,777; Momose et al., *Chem. Pharm. Bull.*, 1977, 25, 1797) or by dissolving metal reduction of an appropriate 6-alkoxyindoline derivative followed by hydrolysis and double bond reduction (H. Iida, Y. Yuasa and C. Kibayashi, *J. Org. Chem.*, 1979, 44, 1074).

Ketones 6.1 (a=1; b=1; c=0; d=3) can be prepared by cyclization of an appropriate 3-(4-oxocyclohex-2-en-1-yl) propanamide followed by amide reduction (A. I. Meyers and D. Berney, *J. Org. Chem.*, 1989, 54, 4673) or by reaction of but-3-en-2-one with an appropriate 1,4,5,6-tetrahydropyridine derivative (Vazquez et al., *Tetrahedron Asymm.*, 2001, 12, 2099). Ketones 6.1 wherein a=0 can, in general, be transformed into ketones 6.1 wherein a=1 by means of 1,2-carbonyl transposition methods, such as those described by Ogata et al., *Eur. J. Med. Chem.*, 1991, 26, 889; W. E. Fristad, T. R. Bailey and L. A. Paquette, *J. Org. Chem.*, 1978, 43, 1620; J. A. Marshall and H. Roebke, *J. Org. Chem.*, 1969, 34, 4188; Y. Tsuda ad S. Hosoi, *Chem. Pharm. Bull.*, 1985, 33, 1745; and T. Nakai and T. Mimura, *Tetrahedron Lett.*, 1979, 531.

When these methods are considered, it is apparent that a large number of compounds of formula 1.1 can be synthesized.

Other features of the invention will become apparent in the course of the following descriptions of exemplary embodiments that are given for illustration of the invention and are not intended to be limiting thereof.

EXAMPLES

Abbreviations used in the Examples are defined as follows: "° C." for degrees Celsius, "g" for gram or grams, "mg" for milligram or milligrams, "mL" for milliliter or milliliters, "mmol" for millimole or millimoles, "μL" for microliter or microliters, "μmol" for micromole or micromoles, "$^1$H" for proton, "h" for hour or hours, "M" for molar, "N" for normal, "min" for minute or minutes, "MHz" for megahertz, "atm" for atmosphere or atmospheres, "MS" for mass spectroscopy, "ES+" for positive electrospray ionization, "m/z" for molecular weight divided by charge, "NMR" for nuclear magnetic resonance spectroscopy, "s" for singlet, "d" for doublet, "dd" for doublet of doublets, "m" for multiplet, "b" for broadened.

Example 1

Part A: Preparation of endo-5-benzylaminooctahydrocyclopenta[c]pyrrole-2-carboxylic acid tert-butyl ester 5-Oxooctahydrocyclopenta[c]pyrrole-2-carboxylic acid tert-butyl ester (prepared according to the procedure described by D. P. Becker and D. L. Flynn, *Tetrahedron*, 1993, 49, 5047; 500 mg, 2.2 mmol) and benzylamine (242 µL, 2.2 mmol) were dissolved in 1,2-dichloroethane (8 mL). Acetic acid (190 µL, 3.3 mmol) and sodium triacetoxyborohydride (706 mg, 3.3 mmol) were added sequentially, and the mixture was stirred at room temperature for 2.75 h. Aqueous sodium hydroxide (1.0 N) was added and the mixture was stirred rapidly for a few minutes. The layers were separated, and the aqueous phase was extracted with dichloromethane. The combined organic phases were dried over sodium sulfate and concentrated under vacuum to yield a residue. The residue was purified by flash chromatography to provide the title compound as a pale yellow oil (538 mg, 77%). $^1$H NMR (400 MHz, CDCl$_3$) δ 7.15 (m, 3H), 7.10 (m, 2H), 3.61 (s, 2H), 3.29 (m, 2H), 3.12 (m, 2H), 2.98 (m, 1H), 2.38 (m, 2H), 2.04 (m, 2H), 1.28 (s, 9H), 1.13 (m, 2H). MS (ES$^+$) m/z 317.21 (M+H$^+$). Also isolated was a mixture of the title product and its exo-isomer (91 mg, 13%).

Part B: Preparation of endo-5-aminooctahydrocyclopenta[c]pyrrole-2-carboxylic acid tert-butyl ester A mixture of endo-5-benzylaminooctahydrocyclopenta[c]pyrrole-2-carboxylic acid tert-butyl ester (525 mg, 1.65 mmol) and 20% palladium hydroxide on carbon (Pearlman's catalyst; 475 mg) in methanol (8 mL) was stirred rapidly under 1 atm of hydrogen at room temperature for 17.5 h. The mixture was filtered through celite and the solids were washed with methanol. The combined filtrates were concentrated to provide a white waxy solid (345 mg, 92%). $^1$H NMR (400 MHz, CDCl$_3$) δ 3.38 (m, 7H), 2.58 (m, 2H), 2.24 (m, 2H), 1.45 (s, 9H), 1.28 (m, 2H). MS (ES$^+$) m/z 227.18 (M+H$^+$).

Part C: Preparation of endo-5-[2-(3-trifluoromethylbenzoylamino)acetylamino]octahydrocyclopenta[c]pyrrole-2-carboxylic acid tert-butyl ester A solution of (3-trifluoromethylbenzoylamino)acetic acid (71 mg, 503 µmol) in tetrahydrofuran (1.5 mL) was treated with N-methylmorpholine (83 µL, 756 µmol). The solution was stirred in an ice/acetone bath, and treated dropwise with isobutyl chloroformate. The resulting mixture was stirred for about 2 min, and then a solution of endo-5-aminooctahydrocyclopenta[c]pyrrole-2-carboxylic acid tert-butyl ester (114 mg, 503 µmol) in tetrahydrofuran (1 mL) and N,N-dimethylformamide (1 mL) containing N-methylmorpholine (50 µL) was added. The mixture was warned to room temperature where it stirred for 40 min. After this time, the mixture was concentrated under vacuum to yield a residue. The residue was partitioned between water and ethyl acetate. The organic phase was washed sequentially with pH 4 buffer, a saturated aqueous sodium hydrogen carbonate solution, water, and a saturated aqueous sodium chloride solution. The organic phase was dried over sodium sulfate and concentrated to yield a residue. The residue was purified by flash column chromatography to provide an amorphous solid (115 mg, 50%). $^1$H NMR (400 MHz, CDCl$_3$) δ 8.04 (s, 1H), 7.95 (d, J=8.1 Hz, 1H), 7.71 (d, J=7.6 Hz, 1H), 7.52 (t, J=7.9 Hz, 1H), 7.33 (bt, J=4.6 Hz, 1H), 6.58 (d, J=7.1 Hz, 1H), 4.19 (m, 1H), 4.04 (d, J=4.6 Hz, 2H), 3.38 (m, 2H), 3.23 (dd, J=11.4, 2.8 Hz, 2H), 2.56 (m, 2H), 2.28 (m, 2H), 1.39 (s, 9H), 1.26 (m, 2H). MS (ES$^+$) m/z 456.27 (M+H$^+$).

Part D: Preparation of N-[(octahydrocyclopenta[c]pyrrol-5-ylcarbamoyl)methyl]-3-trifluoromethylbenzamide trifluoroacetic acid salt A solution of endo-5-[2-(3-trifluoromethylbenzoylamino)acetylamino]octahydrocyclopenta[c]pyrrole-2-carboxylic acid tert-butyl ester (103 mg, 226 µmol) in dichloromethane (4 mL) was treated with trifluoroacetic acid (2 mL). The reaction mixture was stirred for 50 min. After this time, the solution was concentrated under vacuum to yield a residue. The residue was triturated with several portions of diethyl ether, decanted, and dried under vacuum to provide a white powder (96 mg, 90%). $^1$H NMR (400 MHz, methanol-d$_4$) δ 8.23 (s, 1H), 8.15 (d, J=8.1 Hz, 1H), 7.89 (d, J=8.1 Hz, 1H), 7.72 (t, J=7.6 Hz, 1H), 4.14 (m, 1H), 4.03 (s, 2H), 3.40 (dd, J=11.7, 7.6 Hz, 2H), 3.20 (dd, J=12.0, 3.3 Hz, 2H), 2.90 (m, 2H), 2.39 (m, 2H), 1.40 (m, 2H). MS (ES$^+$) m/z 356 (M+H$^+$).

Example 2

Preparation of endo-N-[(2-isopropyloctahydrocyclopenta[c]pyrrol-5-ylcarbamoyl)methyl]-3-trifluoromethylbenzamide trifluoroacetic acid salt The product of Example 1 Part D was converted to the free base by partitioning between ethyl acetate and 1.0 N aqueous sodium hydroxide. The organic phase was dried over sodium sulfate and concentrated. A portion of this material (27 mg, 76 µmol) was dissolved in 1,2-dichloroethane (2 mL) and the resulting solution was treated sequentially with acetone (17 µL, 228 µmol), acetic acid (22 µL, 380 µmol) and sodium triacetoxyborohydride (48 mg, 228 µmol). The mixture was stirred at room temperature for 125 min, then was concentrated under vacuum to yield a residue. The residue was partitioned between ethyl acetate and saturated aqueous sodium hydrogen carbonate. The aqueous phase was extracted twice with additional ethyl acetate. The combined organic phases were dried over sodium sulfate and concentrated under vacuum to provide a glass. $^1$H NMR (400 MHz, methanol-d$_4$) δ 8.11 (s, 1H), 8.04 (d, J=7.6 Hz, 1H), 7.76 (d, J=7.6 Hz, 1H), 7.59 (t, J=5.9 Hz, 1H), 4.07 (m, 1H), 3.90 (s, 2H), 2.62 (d, J=9.2 Hz, 2H), 2.55 (m, 2H), 2.44 (m, 2H), 2.28 (m, 1H), 2.07 (m, 2H), 1.32 (m, 2H), 1.03 (d, J=6.6 Hz, 6H). MS (ES$^+$) m/z 398.21 (M+H$^+$). The glass was dissolved in a small amount of acetonitrile, treated with one drop of trifluoroacetic acid, diluted with water, frozen at –78° C., and lyophilized to provide a white powder (38 mg, 100%).

Example 3

Part A: Preparation of allyl-hex-2-ynyl-carbamic acid tert-butyl ester

A solution of allyl-prop-2-ynyl-carbamic acid tert-butyl ester (prepared according to the method of Boger et al., *J. Am. Chem. Soc.*, 1996, 118, 2109; 1.95 g, 10 mmol) in anhydrous tetrahydrofuran (10 mL) was stirred at 0° C. and treated with n-butyllithium (1.6 M solution in hexane; 7.2 mL, 11.5 mmol) during a 5 min period. After being stirred for an additional 5 min, the solution was treated sequentially with hexamethylphosphoramide (2 mL) and a solution of 1-iodopropane (1.71 mL, 17.5 mmol) in tetrahydrofuran (2 mL). After 65 min, the cooling bath was removed and the mixture was allowed to warm to room temperature where it stirred for 80 min. At the conclusion of this period, saturated aqueous ammonium chloride was added, followed by water to dissolve the solids. The mixture was extracted with ethyl acetate, and the combined organic phases were washed with saturated aqueous sodium chloride, dried over sodium sulfate and concentrated to yield a residue. The residue was purified by flash chromatography to provide a pale yellowish oil (1.67 g, 70%). $^1$H NMR (400 MHz, CDCl$_3$) δ 5.80 (m, 1H), 5.17 (m, 2H), 4.1-3.9 (m, 4H), 2.17 (m, 2H), 1.60 (m, 2H), 1.48 (s, 9H), 0.99 (m, 3H). MS (ES$^+$) m/z 238.27 (M+H$^+$)

Part B: Preparation of 5-oxo-6-propyl-3,3a,4,5-tetrahydro-1H-cyclopenta[c]pyrrole-2-carboxylic acid tert-butyl ester A solution of allyl-hex-2-ynyl-carbamic acid tert-butyl ester (741 mg, 3.12 mmol) in dichloromethane (50 mL) was added to dicobalt octacarbonyl (1.12 g, 3.28 mmol) under an argon atmosphere. The resulting solution was stirred at room temperature for 1.5 h. After this time, N-methylmorpholine N-oxide (2.56 g, 21.9 mmol) was added in portions during a 60 min period. Upon completion of addition, the reaction mixture was stirred for an additional 2.5 h. At the conclusion of this period, the mixture was filtered through silica gel, and the solid was washed with a 1:1 ethyl acetate-hexane solution (200 mL). The filtrate was concentrated under vacuum to yield a residue. The residue was purified by flash column chromatography to provide a light brown oil (321 mg, 38%). $^1$H NMR (400 MHz, CDCl$_3$) δ 5.3-3.9 (m, 3H), 3.17 (m, 1H), 2.80 (m, 1H), 2.67 (m, 1H), 2.29 (m, 1H), 2.13 (m, 2H), 1.51 (m+2s, 11H), 0.91 (m, 3H). MS (ES$^+$) m/z 266.19 (M+H$^+$).

Part C: Preparation of endo-5-oxo-4-propyl-octahydrocyclopenta[c]pyrrole-2-carboxylic acid tert-butyl ester A mixture of 5-oxo-6-propyl-3,3a,4,5-tetrahydro-1H-cyclopenta[c]pyrrole-2-carboxylic acid tert-butyl ester (310 mg, 1.16 mmol), 95% ethanol (6 mL) and 10% palladium on charcoal (160 mg) was stirred vigorously under 1 atm of hydrogen at room temperature for 3.5 h. The mixture was filtered through celite and the solids were washed with ethanol. The combined filtrates were concentrated to provide an oil which was purified by flash chromatography to provide the exo isomer as an oil (11 mg), followed by a mixture of both isomers (ca. 15:85 exo:endo, 105 mg), and the endo isomer (135 mg), in 80% yield (endo:exo ca. 9:1 overall). Endo isomer: $^1$H NMR (400 MHz, CDCl$_3$) δ 3.40 (m, 1H), 3.38 (m, 1H), 3.28 (m, 1H), 2.86 (m, 1H), 2.76 (t, J=10.4 Hz, 1H), 2.63 (m, 1H), 2.48 (dd, J=19.3, 9.2 Hz, 1H), 2.27 (m, 1H), 1.82 (dd, J=19.3, 9.7 Hz, 1H), 1.67 (m, 1H), 1.32 (s, 9H), 1.27 (m, 2H), 1.01 (m, 1H), 0.77 (t, J=7.1 Hz, 3H). MS (ES$^+$) m/z 368.21 (M+H$^+$). Exo isomer: $^1$H NMR (400 MHz, CDCl$_3$) δ 3.72 (t, J=9.2 Hz, 1H), 3.63 (dd, J=11.2, 7.1 Hz, 1H), 3.38 (m, 1H), 3.09 (m, 1H), 2.91 (m, 1H), 2.58 (m, 1H), 2.45 (dd, J=18.8, 8.1 Hz, 1H), 2.26 (dd, J=19.1, 3.3 Hz, 1H), 2.04 (m, 1H), 1.47 (s, 9H), 1.43 (m, 4H), 0.94 (t, J=7.1 Hz, 3H). MS (ES$^+$) m/z 368.21 (M+H$^+$).

Part D: Preparation of 4-endo-5-benzylamino-4-propyloctahydrocyclopenta[c]pyrrole-2-carboxylic acid tert-butyl ester A solution of endo-5-oxo-4-propyl-octahydrocyclopenta[c]pyrrole-2-carboxylic acid tert-butyl ester (264 mg, 987 μmmol) in 1,2-dichloroethane (4 mL) was treated sequentially with benzylamine (108 μL, 987 μmol), acetic acid (85 μL, 1.48 mmol) and sodium triacetoxyborohydride (314 mg, 1.48 mmol). The mixture was stirred at room temperature for 70 h. At the conclusion of this period, the mixture was analyzed by thin layer chromatography, which indicated that some starting material remained. Additional quantities of the reagents as given above were added, and the mixture was stirred for 64 h. After this period, the mixture was concentrated under vacuum to yield a residue. The residue was partitioned between ethyl acetate and saturated aqueous sodium hydrogen carbonate. The aqueous phase was extracted twice more with ethyl acetate, and the combined extracts were dried over sodium sulfate and concentrated under vacuum to yield a residue. The residue was purified by flash column chromatography to yield an oil (184 mg, 52%), which was a mixture of exo and endo amine isomers. MS (ES$^+$) m/z 355 (M+H$^+$)

Part E: Preparation of 4-endo-5-amino-4-propyloctahydrocyclopenta[c]pyrrole-2-carboxylic acid tert-butyl ester A solution of 4-endo-5-benzylamino-4-propyloctahydrocyclopenta[c]pyrrole-2-carboxylic acid tert-butyl ester (200 mg, 557 μmol) in methanol (5 mL) was stirred with 20% palladium hydroxide on charcoal (Pearlman's catalyst; 200 mg) under 1 atm of hydrogen for 18 h. The mixture was filtered through celite, and the solids were washed with methanol. The filtrate was concentrated to provide a glassy foam (154 mg, quantitative) which was a mixture of diastereomers (ca. 7:3) and used without further purification. $^1$H NMR (400 MHz, CDCl$_3$) δ 8.55 (bs, 1.4H), 8.25 (bs, 0.6H), 3.7-2.8 (m, 5H), 2.7-2.2 (m, 2H), 1.9-1.5 (m, 5H), 1.39 (s, 9H), 1.28 (m, 2H), 0.89 (m, 3H). MS (ES$^+$) m/z 269.25 (M+H$^+$).

Part F: Preparation of 4-endo-4-propyl-5-[2-(3-trifluoromethylbenzoylamino)acetylamino]octahydrocyclopenta[c]pyrrole-2-carboxylic acid tert-butyl ester A solution of 4-endo-5-amino-4-propyloctahydrocyclopenta[c]pyrrole-2-carboxylic acid tert-butyl ester (48 mg, 186 μmol) in acetonitrile (1 mL) was treated sequentially with (3-trifluoromethylbenzoylamino)acetic acid (46 mg, 186 μmol), diisopropylethylamine (65 μL, 372 μmol) and TBTU (66 mg, 204 μmol). The mixture was stirred at room temperature for 18.5 h, then was diluted with ethyl acetate. The solution was washed sequentially with 1N aqueous hydrochloric acid, saturated aqueous sodium hydrogen carbonate, water and saturated aqueous sodium chloride, then was dried over sodium sulfate and concentrated under vacuum. The residue was purified by preparative radial thin layer chromatography to provide a pale tan glassy foam (61 mg, 66%) which was a mixture of diastereomers (ca. 3:1) by NMR. $^1$H NMR (400 MHz, CDCl$_3$) δ 8.19 (s, 1H), 8.01 (d, J=7.6 Hz, 1H), 7.87 (d, J=7.6 Hz, 1H), 7.68 (m, 1H), 7.43 (bm, ca. 0.25H), 7.31 (bm, ca. 0.75H), 6.52 (bm, ca. 0.25H), 6.31 (bm, ca. 0.75H), 4.3-4.0 (m, 3H), 3.52 (m, 2H), 3.38 (m, 2H), 2.9-2.6 (m, 1H), 2.5-2.3 (m, 2H), 1.59 (m, 2H), 1.54 (s, 9H), 1.36 (m, 4H), 0.96 (m, 3H). MS (ES$^+$) m/z 498.20 (M+H$^+$), 398.20 ([M+H—COOC4H9]$^+$).

Part G: Preparation of 4-endo-N-[(2-isopropyl-4-propyloctahydrocyclopenta[c]pyrrol-5-ylcarbamoyl)methyl]-3-trifluoromethylbenzamide trifluoroacetic acid salt A solution of 4-endo-4-propyl-5-[2-(3-trifluoromethylbenzoylamino)acetylamino]octahydrocyclopenta[c]-pyrrole-2-carboxylic acid tert-butyl ester (61 mg, 122 µmol) in dichloromethane (2 mL) was treated with trifluoroacetic acid (2 mL) and the mixture was stirred for 2.5 h. The mixture was concentrated under vacuum and partitioned between 1N aqueous sodium hydroxide and ethyl acetate. The aqueous phase was extracted twice more with ethyl acetate, and the combined organic layers were dried over sodium sulfate and concentrated under vacuum to provide a colorless gum (52 mg, quantitative). MS (ES$^+$) m/z 398.22 (M+H$^+$). The colorless gum was dissolved in 1,2-dichloroethane (2 mL) and treated sequentially with acetone (27 µL, 366 µmol), acetic acid (35 µL, 610 µmol) and sodium triacetoxyborohydride (78 mgL, 366 µmol). The mixture was stirred at room temperature for 17.5 h, then was concentrated under vacuum to yield a residue. The residue was partitioned between saturated aqueous sodium hydrogen carbonate and ethyl acetate, and the aqueous phase was extracted twice more with ethyl acetate. The combined organic phases were dried over sodium sulfate and concentrated to yield a residue. The residue was purified by preparative high pressure liquid chromatography, and the desired fraction was lyophilized to provide a white powder (41 mg, 61%), which was a mixture of diastereomers by NMR. $^1$H NMR (400 MHz, methanol-d$_4$) δ 8.11 (s, 1H), 8.04 (d, J=7.1 Hz, 1H), 7.77 (d, J=7.6 Hz, 1H), 7.60 (t, J=7.9 Hz, 1H), 3.95 (m, 3H), 3.73 (m, 2H), 3.32 (m, 2H), 2.79 (m, 2H), 2.6-2.2 (m, 2H), 1.8-1.1 (m, 6H), 1.28 (m, 6H), 0.84 (m, 3H). MS (ES$^+$) m/z 440.25 (M+H$^+$)

Example 4

Part A: Preparation of 4-endo-5-endo-5-(2-{2-[(morpholine-4-carbonyl)amino]-5-trifluoromethylbenzoylamino}acetylamino)-4-propyloctahydrocyclopenta[c]pyrrole-2-carboxylic acid tert-butyl ester Following the procedure of Example 3 Part F, 4-endo-5-amino-4-propyloctahydrocyclopenta[c]pyrrole-2-carboxylic acid tert-butyl ester (prepared according to the procedure of Example 3 Part E; 48 mg, 186 µmol) and {2-[(morpholine-4-carbonyl)amino]-5-trifluoromethylbenzoylamino}acetic acid (prepared according to WO PCT 0250019; 70 mg, 186 µmol) were converted to the title product (34 mg, 29%). $^1$H NMR (400 MHz, CDCl$_3$) δ 11.06 (s, 1H), 8.51 (d, J=9.2 Hz, 1H), 7.75 (s, 1H), 7.72 (bs, 1H), 7.57 (d, J=9.2 Hz, 1H), 6.08 (bt, J=8.7 Hz, 1H), 3.98 (m, 2H), 3.93 (m, 1H), 3.68 (m, 4H), 3.46 (m, 4H), 3.34 (m, 2H), 3.20 (m, 2H), 2.54 (m, 2H), 2.27 (m, 1H), 2.20 (m, 1H), 1.98 (m, 1H), 1.42 (m, 1H), 1.39 (s, 9H), 1.24 (m, 4H), 0.82 (m, 3H). MS (ES$^+$) m/z 625.69 (M+H$^+$). Additional product (43 mg, 37%) was isolated from the chromatographic purification as a 6:4 mixture with the diastereomeric 4-endo-5-exo product.

Part B: Preparation of morpholine-4-carboxylic acid 4-endo-5-endo-(2-{[(2-isopropyl-4-propyloctahydrocyclopenta[c]pyrrol-5-ylcarbamoyl)methyl]carbamoyl}-4-trifluoromethylphenyl)amide trifluoroacetic acid salt Following the procedure of Example 3, Part G, 4-endo-5-endo-5-(2-{2-[(morpholine-4-carbonyl)amino]-5-trifluoromethylbenzoylamino}acetylamino)-4-propyloctahydrocyclopenta[c]pyrrole-2-carboxylic acid tert-butyl ester (34 mg, 54 µmol) was converted to the title product (11 mg, 30%). $^1$H NMR (400 MHz, methanol-d$_4$) δ 8.36 (d, J=8.7 Hz, 1H), 8.02 (s, 1H), 7.65 (d, J=8.7 Hz, 1H), 3.92 (m, 2H), 3.80 (m, 1H), 3.62 (m, 4H), 3.43 (m, 4H), 3.33 (m, 2H), 3.11 (m, 1H), 2.80 (m, 2H), 2.40 (m, 1H), 2.22 (m, 1H), 1.68 (m, 1H), 1.28 (m, 1H), 0.83 (m, 3H). MS (ES$^+$) m/z 568.35 (M+H$^+$)

Example 5

Part A: Preparation of 3-trifluoromethyl-N-[(4-endo-2-trityl-octahydrocyclopenta[c]pyrrol-4-ylcarbamoyl)-methyl]benzamide Following the procedure of Example 3 Part F, endo-2-trityloctahydrocyclopenta[c]pyrrol-4-amine (prepared following the procedures of European Patent Application EP 0359172A1; 100 mg, 271 µmol) was converted into the title product as a glass (136 mg, 84%). $^1$H NMR (400 MHz, CDCl$_3$) δ 8.11 (s, 1H), 7.97 (d, J=7.6 Hz, 1H), 7.80 (d, J=7.6 Hz, 1H), 7.57 (t, J=7.6 Hz, 1H), 7.47 (d, J=7.6 Hz, 6H), 7.32 (m, 1H), 7.27 (m, 6H), 7.17 (t, J=7.3 Hz, 3H), 6.39 (d, J=6.6 Hz, 1H), 4.22 (dd, J=16.3, 5.1 Hz, 1H), 4.10 (m, 1H), 2.74 (m, 1H), 2.56 (m, 1H), 2.27 (m, 4H), 1.93 (m, 1H), 1.78 (m, 2H), 1.61 (m, 2H). MS (ES$^+$) m/z 598.28 (M+H$^+$).

Part B: Preparation of N-[(endo-octahydrocyclopenta-[c]pyrrol-4-ylcarbamoyl)methyl]-3-trifluoromethylbenz-amide 3-Trifluoromethyl-N-[(4-endo-2-trityloctahydrocyclopenta[c]pyrrol-4-ylcarbamoyl)methyl]benzamide (130 mg, 217 mmol) was dissolved in trifluoroacetic acid (4 mL) and stirred at room temperature for 10 min, and then water (4 mL) was added dropwise. Upon completion of addition, the mixture was stirred for 40 min. After this period, the mixture was concentrated to near dryness under vacuum to yield a residue. The residue was dissolved in ethyl acetate. The resulting solution was extracted twice with 1N aqueous hydrochloric acid, and the aqueous phase was made basic with 15% aqueous sodium hydroxide. The resulting mixture was extracted with ethyl acetate. The organic phase was dried over sodium sulfate and concentrated under vacuum to provide a white solid (54 mg, 70%). $^1$H NMR (400 MHz, CDCl$_3$) δ 7.91 (s, 1H), 7.82 (d, J=7.6 Hz, 1H), 7.55 (d, J=7.6 Hz, 1H), 7.36 (t, J=7.6 Hz, 1H), 4.18 (m, 1H), 4.08 (dd, J=16.8, 5.6 Hz, 1H), 3.85 (m, 1H), 2.94 (m, 1H), 2.85 (m, 1H), 2.75-2.5 (m, 4H), 1.76 (m, 1H), 1.56 (m, 1H), 1.28 (m, 1H). MS (ES$^+$) m/z 356.22 (M+H$^+$)

Part C: Preparation of N-[(endo-2-isopropyloctahydrocyclopenta[c]pyrrol-4-ylcarbamoyl)methyl]-3-trifluoromethylbenzamide Following the procedure of Example 3 Part G, N-[(4-endo-octahydrocyclopenta[c]pyrrol-4-ylcarbamoyl)methyl]-3-trifluoromethylbenzamide (21 mg, 59 µmol) was converted into the title product as a white powder after lyophilization (5 mg, 16%). $^1$H NMR (400 MHz, methanol-d$_4$) δ 8.11 (s, 1H), 8.04 (d, J=7.6 Hz, 1H), 7.78 (d, J=7.6 Hz, 1H), 7.60 (t, J=7.6 Hz, 1H), 3.97 (m, 2H), 3.79 (m, 2H), 3.48 (m, 1H), 3.34 (m, 1H), 3.14 (m, 1H), 2.79 (m, 2H), 2.60 (t, J=10.7 Hz, 1H), 1.89 (m, 1H), 1.72 (m, 2H), 1.56 (m, 1H), 1.28 (m, 6H). MS (ES$^+$) m/z 398.22 (M+H$^+$)

Example 6

Part A. Preparation of acetic acid 4-(tert-butoxycarbonylprop-2-ynylamino)-but-2-enyl ester This compound is prepared in the manner described in Boger et al. ((*J. Am. Chem. Soc.*, 1996, 118, 2109)), namely, prop-2-ynylcarbamic acid tert-butyl ester is converted to the title compound with acetic acid 4-chlorobut-2-enyl ester (see Organ et al., *J. Org. Chem.* 2000, 65, 7959) rather than allyl bromide as set forth Boger et al.

Part B. Preparation of 4-acetoxymethyl-5-[2-(3-trifluoromethylbenzoylamino)acetylamino]octahydrocyclopenta[c]pyrrole-2-carboxylic acid tert-butyl ester By sequentially following the procedures of Example 3, Parts B and C, and Example 1, Parts A through C, acetic acid 4-(tert-butoxy-carbonylprop-2-ynylamino)-but-2-enyl ester is converted to the title product.

Part C. Preparation of 4-hydroxymethyl-5-[2-(3-trifluoromethylbenzoylamino)acetylamino]octahydrocyclopenta[c]pyrrole-2-carboxylic acid tert-butyl ester A solution of 4-acetoxymethyl-5-[2-(3-trifluoromethylbenzoylamino)acetylamino]octahydrocyclopenta[c]-pyrrole-2-carboxylic acid tert-butyl ester in tetrahydrofuran is treated with aqueous lithium hydroxide and the mixture is stirred at room temperature until the reaction is complete. The reaction mixture is concentrated under vacuum yielding an aqueous residue. The aqueous residue is extracted with ethyl acetate, and the organic phases are dried over sodium sulfate and concentrated under vacuum yielding a residue. The residue is purified by flash column chromatography providing the title product.

Part D. Preparation of 4-methoxymethyl-5-[2-(3-trifluoromethylbenzoylamino)acetylamino]octahydrocyclopenta[c]pyrrole-2-carboxylic acid tert-butyl ester A solution of 4-hydroxymethyl-5-[2-(3-trifluoromethylbenzoylamino)acetylamino]octahydrocyclopenta[c]-pyrrole-2-carboxylic acid tert-butyl ester in a small amount of DMF and a large excess of iodomethane is treated with silver oxide and stirred at room temperature until the reaction is complete. The reaction mixture is filtered through Celite and concentrated under vacuum yielding a residue. The residue is purified by flash column chromatography providing the title product.

Part E. Preparation of N-[(2-isopropyl-4-methoxymethyloctahydrocyclopenta[c]pyrrol-5-ylcarbamoyl)-methyl]-3-trifluoromethylbenzamide By sequentially following the procedures of Example 1, Part D, and Example 2,4-methoxymethyl-5-[2-(3-trifluoromethylbenzoylamino)acetylamino]octahydrocyclopenta[c]pyrrole-2-carboxylic acid tert-butyl ester is converted to the title product.

Example 7

Part A. Preparation of 4-isopropylsulfanylmethyl-5-[2-(3-trifluoromethylbenzoylamino)acetylamino] octahydrocyclopenta[c]pyrrole-2-carboxylic acid tert-butyl ester A solution of 4-hydroxymethyl-5-[2-(3-trifluoromethylbenzoylamino)acetylamino]octahydrocyclopenta[c]-pyrrole-2-carboxylic acid tert-butyl ester (see Example 6, Part C) in dichloromethane is cooled to 0° C. and treated with triethylamine and methanesulfonyl chloride. The reaction is stirred at room temperature until complete, and then water is added yielding a methanesulfonate mixture. The aqueous phase is extracted with ethyl acetate and concentrated. In a separate flask, propane-2-thiol is dissolved in DMF and cooled to 0° C. Sodium hydride is added, and the mixture is stirred at room temperature for 2 h. The methanesulfonate mixture prepared above is dissolved in DMF and added slowly to the thiolate solution. Upon completion of addition, the mixture is stirred until the reaction is complete. Water and ethyl acetate are added, and the organic phase is dried over sodium sulfate and concentrated yielding a residue. The residue is purified by flash column chromatography providing the title product.

Part B. Preparation of 4-(propane-2-sulfonylmethyl)-5-[2-(3-trifluoromethylbenzoylamino)acetylamino]-octahydrocyclopenta[c]pyrrole-2-carboxylic acid tert-butyl ester A solution of 4-isopropylsulfanylmethyl-5-[2-(3-trifluoromethylbenzoylamino)acetylamino]octahydrocyclopenta[c]pyrrole-2-carboxylic acid tert-butyl ester in isopropanol is treated with a solution of Oxone in water, and the mixture is stirred at room temperature until the reaction is complete. Water and ethyl acetate are added, and the organic layer is separated, dried over sodium sulfate and concentrated under vacuum providing the title product.

Part C. Preparation of N-{[2-isopropyl-4-(propane-2-sulfonylmethyl)octahydrocyclopenta[c]pyrrol-5-ylcarbamoyl]methyl}-3-trifluoromethylbenzamide By sequentially following the procedures of Example 1, Part D, and Example 2,4-(propane-2-sulfonylmethyl)-5-[2-(3-trifluoromethyl-benzoylamino)acetylamino]-octahydrocyclopenta[c]pyrrole-2-carboxylic acid tert-butyl ester is converted to the title product.

Example 8

Part A. Preparation of 4-phenylsulfanylmethyl-5-[2-(3-trifluoromethylbenzoylamino)acetylamino]octahydrocyclopenta[c]pyrrole-2-carboxylic acid tert-butyl ester A mixture of 4-hydroxymethyl-5-[2-(3-trifluoromethylbenzoylamino)acetylamino]octahydrocyclopenta[c]-pyrrole-2-carboxylic acid tert-butyl ester (see Example 6, Part C), diphenyl disulfide, tributylphosphine and tetrahydrofuran is heated at reflux until the reaction is complete. The mixture is cooled to room temperature and concentrated

41 yielding a residue. The residue is purified by flash column chromatography providing the title product.

Part B. Preparation of 4-benzenesulfonylmethyl-5-[2-(3-trifluoromethylbenzoylamino)acetylamino] octahydrocyclopenta[c]pyrrole-2-carboxylic acid tert-butyl ester Following the procedure of Example 7, Part B, 4-phenylsulfanylmethyl-5-[2-(3-trifluoromethylbenzoylamino) acetylamino]octahydrocyclopenta[c]pyrrole-2-carboxylic acid tert-butyl ester is converted to the title product.

Part C. Preparation of N-[(4-benzenesulfonylmethyl-2-isopropyloctahydrocyclopenta[c]pyrrol-5-ylcarbamoyl)-methyl]-3-trifluoromethylbenzamide By sequentially following the procedures of Example 1, Part D, and Example 2,4-benzenesulfonylmethyl-5-[2-(3-trifluoromethylbenzoylamino)acetylamino]octahydrocyclopenta[c]pyrrole-2-carboxylic acid tert-butyl ester is converted to the title product.

Example 9

Part A. Preparation of 4-acetoxymethyl-5-(2-benzyloxycarbonylaminoacetylamino)octahydrocyclopenta [c]-pyrrole-2-carboxylic acid tert-butyl ester By sequentially following the procedures of Example 3, Parts B and C, and Example 1, Parts A and B, acetic acid 4-(tert-butoxy-carbonylprop-2-ynylamino)-but-2-enyl ester is converted to 4-acetoxymethyl-5-aminooctahydrocyclopenta[c]pyrrole-2-carboxylic acid tert-butyl ester. A solution of this material and benzyloxycarbonyl glycine in acetonitrile is treated sequentially with diisopropylethylamine and TBTU, and the resulting mixture is stirred at room temperature until the reaction is complete. The mixture is concentrated under vacuum yielding a residue. The residue is purified by flash column chromatography providing the title product.

Part B. Preparation of 5-(2-benzyloxycarbonylaminoacetylamino)-4-methoxymethyloctahydrocyclopenta[c]-pyrrole 2-carboxylic acid tert-butyl ester By sequentially following the procedures of Example 6, Parts C and D, 4-acetoxymethyl-5-(2-benzyloxycarbonylaminoacetylamino)octahydrocyclopenta[c]-pyrrole-2-carboxylic acid tert-butyl ester is converted to the title product.

Part C. Preparation of [(2-isopropyl-4-methoxymethyloctahydrocyclopenta[c]pyrrol-5-ylcarbamoyl)-methyl]-carbamic acid benzyl ester By sequentially following the procedures of Example 1, Part D, and Example 2,5-(2-benzyloxycarbonylaminoacetylamino)-4-methoxymethyloctahydrocyclopenta[c]-pyrrole-2-carboxylic acid tert-butyl ester is converted to the title product.

Part D. Preparation of 2-amino-N-(2-isopropyl-4-methoxymethyloctahydrocyclopenta[c]pyrrol-5-yl) acetamide A solution of [(2-isopropyl-4-methoxymethyloctahydrocyclopenta[c]pyrrol-5-ylcarbamoyl)methyl]carbamic acid benzyl ester in 30% hydrogen bromide in acetic acid is stirred at room temperature until the reaction is complete. The mixture is diluted with ether and the precipitated material is purified by trituration with additional ether, followed if necessary by reverse phase HPLC and lyophilization, providing the title product.

Part E. Preparation of N-(2-isopropyl-4-methoxymethyloctahydrocyclopenta[c]pyrrol-5-yl)-2-(6-trifluoromethylquinazolin-4-ylamino)acetamide A mixture of 2-amino-N-(2-isopropyl-4-methoxymethyloctahydrocyclopenta[c]pyrrol-5-yl)acetamide, 4-chloro-6-trifluoromethylquinazoline (see Armarego et al., *J. Chem. Soc. B*, 1967, 449) and triethylamine in ethanol is heated at reflux until the reaction is complete. The solution is concentrated under vacuum yielding a residue. The residue is purified by reverse phase HPLC and lyophilization providing the title product.

Utility

Compounds of formula I are shown to be modulators of chemokine receptor activity using assays know by those skilled in the art. In this section, we describe these assays and give their literature reference. By displaying activity in these assays of MCP-1 antagonism, compounds of formula I are expected to be useful in the treatment of human diseases associated with chemokines and their cognate receptors. The definition of activity in these assays is a compound demonstrating an $IC_{50}$ of 20 µM or lower in concentration when measured in a particular assay.

Antagonism of MCP-1 Binding to Human PBMC (Yoshimura et al., *J. Immunol.*, 1990, 145, 292)

Compounds of the present invention have activity in the antagonism of MCP-1 binding to human PBMC (human peripheral blood mononuclear cells) described here.

Millipore filter plates (#MABVN1250) are treated with 100 µl of binding buffer (0.5% bovine serum albumin, 20 mM HEPES buffer and 5 mM magnesium chloride in RPMI 1640 media) for thirty minutes at room temperature. To measure binding, 50 µl of binding buffer, with or without a known concentration compound, is combined with 50 µl of $^{125}$-I labeled human MCP-1 (to give a final concentration of 150 pM radioligand) and 50 µl of binding buffer containing $5 \times 10^5$ cells. Cells used for such binding assays can include human peripheral blood mononuclear cells isolated by Ficoll-Hypaque gradient centrifugation, human monocytes (Weiner et al., *J. Immunol. Methods*, 1980, 36, 89), or the THP-1 cell line which expresses the endogenous receptor. The mixture of compound, cells and radioligand are incubated at room temperature for thirty minutes. Plates are placed onto a vacuum manifold, vacuum applied, and the plates washed three times with binding buffer containing 0.5M NaCl. The plastic skirt is removed from the plate, the plate allowed to air dry, the wells punched out and counted. The percent inhibition of binding is calculated using the total counts obtained in the absence of any competing compound and the background binding determined by addition of 100 nM MCP-1 in place of the test compound.

Antagonism of MCP-1-Induced Calcium Influx (Sullivan et al., *Methods Mol. Biol.*, 114, 125-133 (1999)

Compounds of the present invention have activity in the antagonism of MCP-1-induced calcium influx assay described here.

Calcium mobilization is measured using the fluorescent $Ca^{2+}$ indicator dye, Fluo-3. Cells are incubated at $8\times10^5$ cells/ml in phosphate-buffered saline containing 0.1% bovine serum albumin, 20 mM HEPES buffer, 5 mM glucose, 1% fetal bovine serum, 4 μM Fluo-3 AM and 2.5 mM probenecid for 60 minutes at 37° C. Cells used for such calcium assays can include human monocytes isolated as described by Weiner et al., *J. Immunol. Methods*, 36, 89-97 (1980) or cell lines which expresses the endogenous CCR2 receptor such as THP-1 and MonoMac-6. The cells are then washed three times in phosphate-buffered saline containing 0.1% bovine serum albumin, 20 mM HEPES, 5 mM glucose and 2.5 mM probenecid. The cells are resuspended in phosphate-buffered saline containing 0.5% bovine serum albumin, 20 mM HEPES and 2.5 mM probenecid at a final concentration of $2-4\times10^6$ cells/ml. Cells are plated into 96-well, black-wall microplates (100 μl/well) and the plates centrifuged at 200×g for 5 minutes. Various concentrations of compound are added to the wells (50 μl/well) and after 5 minutes, 50 μl/well of MCP-1 is added to give a final concentration of 10 nM. Calcium mobilization is detected by using a fluorescent-imaging plate reader. The cell monolayer is excited with an argon laser (488 nM) and cell-associated fluorescence measured for 3 minutes, (every second for the first 90 seconds and every 10 seconds for the next 90 seconds). Data are generated as arbitrary fluorescence units and the change in fluorescence for each well determined as the maximum-minimum differential. Compound-dependent inhibition is calculated relative to the response of MCP-1 alone.

Antagonism of MCP-1-Induced Human PBMC Chemotaxis (Bacon et al., *Brit. J. Pharmacol.*, 1988, 95, 966)

Compounds of the present invention have activity in the antagonism of MCP-1-induced human PBMC chemotaxis assay described here.

Neuroprobe MBA96-96-well chemotaxis chamber, Polyfiltronics MPC 96 well plate, and Neuroprobe polyvinylpyrrolidone-free polycarbonate PFD5 8-micron filters are warmed in a 37° C. incubator. Human Peripheral Blood Mononuclear Cells (PBMCS) (Boyum et al., *Scand. J. Clin. Lab Invest. Suppl.*, 1968, 97, 31), freshly isolated via the standard ficoll density separation method, are suspended in DMEM [DMEM?] at $1\times10^7$ c/ml and warmed at 37° C. A 60 nM solution of human MCP-1 is also warmed at 37° C. Dilutions of test compounds are made up at 2× the concentration needed in DMEM. The PBMC suspension and the 60 nm MCP-1 solution are mixed 1:1 in polypropylene tubes with prewarmed DMEM with or without a dilution of the test compounds. These mixtures are warmed in a 37° C. tube warmer. To start the assay, add the MCP-1/compound mixture into the wells of the Polyfiltronics MPC 96 well plate that has been placed into the bottom part of the Neuroprobe chemotaxis chamber. The approximate volume is 400 μl to each well and there should be a positive meniscus after dispensing. The 8 micron filter is placed gently on top of the 96 well plate, a rubber gasket is attached to the bottom of the upper chamber, and the chamber is assembled. A 200 μl volume of the cell suspension/compound mixture is added to the appropriate wells of the upper chamber. The upper chamber is covered with a plate sealer, and the assembled unit is placed in a 37° C. incubator for 45 minutes. After incubation, the plate sealer is removed and all the remaining cell suspension is aspirated off. The chamber is disassembled and the filter gently removed. While holding the filter at a 90-degree angle, unmigrated cells are washed away using a gentle stream of phosphate buffered saline and the top of the filter wiped with the tip of a rubber squeegee. Repeat this wash twice more. The filter is air dried and then immersed completely in Wright Geimsa stain for 45 seconds. The filter is then washed by soaking in distilled water for 7 minutes, and then a 15 second additional wash in fresh distilled water. The filter is again air-dried. Migrated cells on the filter are quantified by visual microscopy.

Mammalian chemokine receptors provide a target for interfering with or promoting immune cell function in a mammal, such as a human. Compounds that inhibit or promote chemokine receptor function are particularly useful for modulating immune cell function for therapeutic purposes.

Accordingly, the present invention is directed to compounds which are useful in the prevention and/or treatment of a wide variety of inflammatory, infectious, and immunoregulatory disorders and diseases, including asthma and allergic diseases, infection by pathogenic microbes (which, by definition, includes viruses), as well as autoimmune pathologies such as the rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation or infectious disease. As a result, one or more inflammatory process, such as leukocyte emigration, adhesion, chemotaxis, exocytosis (e.g., of enzymes, histamine) or inflammatory mediator release, is inhibited.

Similarly, an instant compound which promotes one or more functions of the mammalian chemokine receptor (e.g., a human chemokine) as administered to stimulate (induce or enhance) an immune or inflammatory response, such as leukocyte emigration, adhesion, chemotaxis, exocytosis (e.g., of enzymes, histamine) or inflammatory mediator release, resulting in the beneficial stimulation of inflammatory processes. For example, eosinophils can be recruited to combat parasitic infections. In addition, treatment of the aforementioned inflammatory, allergic and autoimmune diseases can also be contemplated for an instant compound which promotes one or more functions of the mammalian chemokine receptor if one contemplates the delivery of sufficient compound to cause the loss of receptor expression on cells through the induction of chemokine receptor internalization or the delivery of compound in a manner that results in the misdirection of the migration of cells.

In addition to primates, such as humans, a variety of other mammals can be treated according to the method of the present invention. For instance, mammals, including but not limited to, cows, sheep, goats, horses, dogs, cats, guinea pigs, rats or other bovine, ovine, equine, canine, feline, rodent or murine species can be treated. However, the method can also be practiced in other species, such as avian species. The subject treated in the methods above is a mammal, male or female, in whom modulation of chemokine receptor activity is desired. "Modulation" as used herein is intended to encompass antagonism, agonism, partial antagonism and/or partial agonism.

Diseases or conditions of human or other species which can be treated with inhibitors of chemokine receptor function, include, but are not limited to: inflammatory or allergic diseases and conditions, including respiratory allergic diseases such as asthma, allergic rhinitis, hypersensitivity lung diseases, hypersensitivity pneumonitis, eosinophilic cellulitis (e.g., Well's syndrome), eosinophilic pneumonias (e.g., Loeffler's syndrome, chronic eosinophilic pneumonia), eosinophilic fasciitis (e.g., Shulman's syndrome), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), eosinophilia-myalgia syndrome due to the ingestion of contaminated tryptophan, insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as an dermatitis, eczema, atopic dermatitis, allergic contact dermatitis, urticaria; vasculitis (e.g., necrotizing, cutaneous, and hypersensitivity vasculitis); eosinophilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematological malignancies, cytokine-induced toxicity (e.g., septic shock, endotoxic shock), polymyositis, dermatomyositis. Infectious diseases or conditions of human or other species which can be treated with inhibitors of chemokine receptor function, include, but are not limited to, HIV.

Diseases or conditions of humans or other species which can be treated with promoters of chemokine receptor function, include, but are not limited to: immunosuppression, such as that in individuals with immunodeficiency syndromes such as AIDS or other viral infections, individuals undergoing radiation therapy, chemotherapy, therapy for autoimmune disease or drug therapy (e.g., corticosteroid therapy), which causes immunosuppression; immunosuppression due to congenital deficiency in receptor function or other causes; and infections diseases, such as parasitic diseases, including, but not limited to helminth infections, such as nematodes (round worms); (*Trichuriasis, Enterobiasis, Ascariasis, Hookworm, Strongyloidiasis, Trichinosis, filariasis*); trematodes (flukes) (*Schistosomiasis, Clonorchiasis*), cestodes (tape worms) (*Echinococcosis, Taeniasis saginata, Cysticercosis*); visceral worms, visceral larva migraines (e.g., *Toxocara*), eosinophilic gastroenteritis (e.g., *Anisaki* sp., *Phocanema* sp.), cutaneous larva migraines (*Ancylostona braziliense, Ancylostoma caninum*). The compounds of the present invention are accordingly useful in the prevention and treatment of a wide variety of inflammatory, infectious and immunoregulatory disorders and diseases.

In addition, treatment of the aforementioned inflammatory, allergic and autoimmune diseases can also be contemplated for promoters of chemokine receptor function if one contemplates the delivery of sufficient compound to cause the loss of receptor expression on cells through the induction of chemokine receptor internalization or delivery of compound in a manner that results in the misdirection of the migration of cells.

In another aspect, the instant invention may be used to evaluate the putative specific agonists or antagonists of a G protein coupled receptor. The present invention is directed to the use of these compounds in the preparation and execution of screening assays for compounds that modulate the activity of chemokine receptors. Furthermore, the compounds of this invention are useful in establishing or determining the binding site of other compounds to chemokine receptors, e.g., by competitive inhibition or as a reference in an assay to compare its known activity to a compound with an unknown activity. When developing new assays or protocols, compounds according to the present invention could be used to test their effectiveness. Specifically, such compounds may be provided in a commercial kit, for example, for use in pharmaceutical research involving the aforementioned diseases. The compounds of the instant invention are also useful for the evaluation of putative specific modulators of the chemokine receptors. In addition, one could utilize compounds of this invention to examine the specificity of G protein coupled receptors that are not thought to be chemokine receptors, either by serving as examples of compounds which do not bind or as structural variants of compounds active on these receptors which may help define specific sites of interaction.

The compounds of the present invention are used to treat or prevent disorders selected from rheumatoid arthritis, osteoarthritis, septic shock, atherosclerosis, aneurysm, fever, cardiovascular effects, haemodynamic shock, sepsis syndrome, post ischemic reperfusion injury, malaria, Crohn's disease, inflammatory bowel diseases, mycobacterial infection, meningitis, psoriasis, congestive heart failure, fibrotic diseases, cachexia, graft rejection, autoimmune diseases, skin inflammatory diseases, multiple sclerosis, radiation damage, hyperoxic alveolar injury, HIV, HIV dementia, non-insulin dependent diabetes melitus, asthma, allergic rhinitis, atopic dermatitis, idiopathic pulmonary fibrosis, bullous pemphigoid, helminthic parasitic infections, allergic colitis, eczema, conjunctivitis, transplantation, familial eosinophilia, eosinophilic cellulitis, eosinophilic pneumonias, eosinophilic fasciitis, eosinophilic gastroenteritis, drug induced eosinophilia, cystic fibrosis, Churg-Strauss syndrome, lymphoma, Hodgkin's disease, colonic carcinoma, Felty's syndrome, sarcoidosis, uveitis, Alzheimer, Glomerulonephritis, and systemic lupus erythematosus.

In another aspect, the compounds are used to treat or prevent inflammatory disorders selected from rheumatoid arthritis, osteoarthritis, atherosclerosis, aneurysm, fever, cardiovascular effects, Crohn's disease, inflammatory bowel diseases, psoriasis, congestive heart failure, multiple sclerosis, autoimmune diseases, skin inflammatory diseases.

In another aspect, the compounds are used to treat or prevent inflammatory disorders selected from rheumatoid arthritis, osteoarthritis, atherosclerosis, Crohn's disease, inflammatory bowel diseases, and multiple sclerosis.

Combined therapy to prevent and treat inflammatory, infectious and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities. For example, in the treatment or prevention of inflammation, the present compounds may be used in conjunction with an anti-inflammatory or analgesic agent such as an opiate agonist, a lipoxygenase inhibitor, a cyclooxygenase-2 inhibitor, an interleukin inhibitor, such as an interleukin-1 inhibitor, a tumor necrosis factor inhibitor, an NMDA antagonist, an inhibitor or nitric oxide or an inhibitor of the synthesis of nitric oxide, a non-steroidal anti-inflammatory agent, a phosphodiesterase inhibitor, or a cytokine-suppressing anti-inflammatory agent, for example with a compound such as acetaminophen, aspirin, codeine, fentaynl, ibuprofen, indomethacin, ketorolac, morphine, naproxen, phenacetin, piroxicam, a steroidal analgesic, sufentanyl, sunlindac, interferon alpha and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levodesoxy-ephedrine; and antitussive such as codeine, hydrocodone, caramiphen, carbetapentane, or dextramethorphan; a diuretic; and a sedating or non-sedating antihistamine. Likewise, compounds of the present invention may be used in combination with other drugs that are used in the treatment/prevention/suppression or amelioration of the diseases or conditions for which compound of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention may be used. Accordingly, the pharmaceutical compositions of the present invention include those that also contain one or more other active ingredients, in addition to a compound of the present invention.

Examples of other active ingredients that may be combined with a compound of the present invention, either administered separately or in the same pharmaceutical compositions, include, but are not limited to: (a) integrin antagonists such as those for selectins, ICAMs and VLA-4; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as b2-agonists (terbutaline, metaproterenol, fenoterol, isoetharine, albuteral, bitolterol, and pirbuterol), theophylline, cromolyn sodium, atropine, ipratropium bromide, leukotriene antagonists (zafirlukast, montelukast, pranlukast, iralukast, pobilukast, SKB-102,203), leukotriene biosynthesis inhibitors (zileuton, BAY-1005); (f) non-steroidal anti-inflammatory agents (NSAIDs) such as propionic acid derivatives (alminoprofen, benxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (I) other antagonists of the chemokine receptors; (j) cholesterol lowering agents such as HMG-COA reductase inhibitors (lovastatin, simvastatin and pravastatin, fluvastatin, atorvsatatin, and other statins), sequestrants (cholestyramine and colestipol), nicotonic acid, fenofibric acid derivatives (gemfibrozil, clofibrat, fenofibrate and benzafibrate), and probucol; (k) anti-diabetic agents such as insulin, sulfonylureas, biguanides (metformin), a-glucosidase inhibitors (acarbose) and glitazones (troglitazone ad pioglitazone); (1) preparations of interferons (interferon alpha-2a, interferon-2B, interferon alpha-N3, interferon beta-1a, interferon beta-1b, interferon gamma-1b); (m) antiviral compounds such as efavirenz, nevirapine, indinavir, ganciclovir, lamivudine, famciclovir, and zalcitabine; (O) other compound such as 5-aminosalicylic acid an prodrugs thereof, anti-metabolites such as azathioprine and 6-mercaptopurine, and cytotoxic cancer chemotherapeutic agents. The weight ratio of the compound of the present invention to the second active ingredient may be varied and will depend upon the effective doses of each ingredient.

Generally, an effective dose of each will be used. Thus, for example, when a compound of the present invention is combined with an NSAID the weight ratio of the compound of the present invention to the NSAID will generally range from about 1000:1 to about 1:1000, or alternatively from about 200:1 to about 1:200. Combinations of a compound of the present invention and other active ingredients will generally also be within the aforementioned range, but in each case, an effective dose of each active ingredient should be used.

The compounds are administered to a mammal in a therapeutically effective amount. By "therapeutically effective amount" it is meant an amount of a compound of Formula I that, when administered alone or in combination with an additional therapeutic agent to a mammal, is effective to prevent or ameliorate the thromboembolic disease condition or the progression of the disease.

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, or between about 0.01 to 100 mg/kg of body weight per day, or alternatively, between about 1.0 to 20 mg/kg/day. Intravenously, the doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels. Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration may contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field. Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 0.5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin. Where the compounds of this invention are combined with other anticoagulant agents, for example, a daily dosage may be about 0.1 to 100 milligrams of the compound of Formula I and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination. Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low-viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

While the invention has been described in detail and with reference to specific embodiments thereof, it will be apparent to one skilled in the art that various changes and modifications can be made therein without departing from the spirit and scope thereof.

What is claimed is:

1. A compound of formula (I):

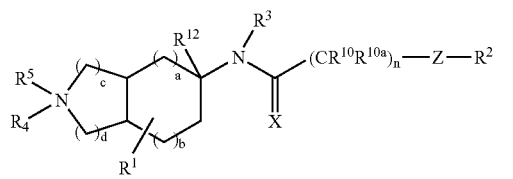

(I)

or a stereoisomer or a pharmaceutically acceptable salt thereof, wherein:
X is O;

Z is selected from a bond, —C(O)—, —C(O)NR$^8$—, —NR$^8$—, —NR$^8$—CR$^{14}$R$^{14}$—, —NR$^8$C(O)—, —NR$^8$C(O)NH—, —NR$^8$C(S)NH—, —NR$^8$SO$_2$—, —NR$^8$SO$_2$NH—, —OC(O)NR$^8$—, —NR$^8$C(O)O—, —(CR$^{25}$R$^{25}$)$_u$—, —CR$^{14}$=CR$^{14}$—, —CR$^{25}$R$^{25}$C(O)—, —C(O)CR$^{25}$R$^{25}$—, —CR$^{25}$R$^{25}$C(=N—OR$^{14}$)—, —O—CR$^{14}$R$^{14}$—, —CR$^{14}$R$^{14}$—O—, —O—, —CHR$^{14}$—NR$^8$—, —S(O)$_p$—, —S(O)$_p$—CR$^{14}$R$^{14}$—, and —S(O)$_p$—NR$^8$—;

$R^1$ is selected from H, $R^6$, $C_{1-6}$ alkyl substituted with 0-3 $R^6$, $C_{2-6}$ alkenyl substituted with 0-3 $R^6$, $C_{2-6}$ alkynyl substituted with 0-3 $R^6$, $C_{6-10}$ aryl group substituted with 0-5 $R^6$, and a 5-10 membered heteroaryl system containing 1-4 heteroatoms selected from N, O, and S, substituted with 0-3 $R^6$;

$R^2$ is selected from a $C_{6-10}$ aryl group substituted with 0-5 $R^7$ and a 5-10 membered heteroaryl system containing 1-4 heteroatoms selected from N, O, and S, substituted with 0-3 $R^7$;

$R^3$ is selected from H, methyl, and ethyl;

$R^4$ is absent, taken with the nitrogen to which it is attached to form an N-oxide, or selected from $C_{1-8}$ alkyl, $C_{2-8}$ alkenyl, $C_{2-8}$ alkynyl, (CR'R')$_r$C$_{3-6}$ cycloalkyl, (CR'R')$_q$C(O)R$^{4b}$, (CR'R')$_q$C(O)NR$^{4a}$R$^{4a}$, (CR'R')$_q$C(O)OR$^{4b}$, and a (CR'R')$_r$—C$_{3-10}$ carbocyclic residue substituted with 0-3 $R^{4c}$;

$R^{4a}$, at each occurrence, is independently selected from H, $C_{1-6}$ alkyl, (CR'R')$_r$C$_{3-6}$ cycloalkyl, and phenyl;

alternatively, two $R^{4a}$s, together with the N to which they are attached, join to form a 3-8 membered heterocycle containing 0-1 additional heteroatoms selected from N, O and S;

$R^{4b}$, at each occurrence, is independently selected from $C_{1-6}$ alkyl, $C_{2-8}$ alkenyl, (CR'R')$_r$C$_{3-6}$ cycloalkyl, $C_{2-8}$ alkynyl, and phenyl;

$R^{4c}$, at each occurrence, is independently selected from $C_{1-6}$ alkyl, $C_{2-8}$ alkenyl, $C_{2-8}$ alkynyl, $C_{3-6}$ cycloalkyl, Cl, F, Br, I, CN, NO$_2$, (CF$_2$)$_r$CF$_3$, (CR'R')$_r$OC$_{1-5}$ alkyl, (CR'R')$_r$OH, (CR'R')$_r$SC$_{1-5}$ alkyl, (CR'R')$_r$NR$^{4a}$R$^{4a}$, and (CR'R')$_r$phenyl;

$R^5$ is selected from H, $C_{1-6}$ alkyl substituted with 0-2 $R^{5e}$, —C(O)R$^{5b}$, —C(O)OR$^{5b}$, —C(O)NR$^{5f}$R$^{5f}$, a $C_{3-10}$ carbocyclic residue substituted with 0-5 $R^{5e}$, and a 5-10 membered heterocyclic system containing 1-4 heteroatoms selected from N, O, and S, substituted with 0-3 $R^{5e}$;

$R^{5b}$, at each occurrence, is selected from $C_{1-6}$ alkyl substituted with 0-3 $R^{5e}$, $C_{3-8}$ alkenyl substituted with 0-2 $R^{5e}$, $C_{3-8}$ alkynyl substituted with 0-2 $R^{5e}$, a (CR'R')$_r$—C$_{3-6}$ carbocyclic residue substituted with 0-2 $R^{5e}$, and a (CR'R')$_r$-5-6 membered heterocyclic system containing 1-4 heteroatoms selected from N, O, and S, substituted with 0-3 $R^{5e}$;

$R^{5e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, NO$_2$, (CF$_2$)$_r$CF$_3$, (CR'R')$_r$OC$_{1-5}$ alkyl, OH, SH, (CR'R')$_r$SC$_{1-5}$ alkyl, (CR'R')$_r$NR$^{5f}$R$^{5f}$, a (CR'R')$_r$C$_{3-6}$ carbocyclic residue substituted with 0-3 $R^{6e}$, and a (CR'R')$_r$-5-6 membered heterocyclic system containing 1-4 heteroatoms selected from N, O, and S, substituted with 0-2 $R^{6e}$;

$R^{5f}$, at each occurrence, is selected from H, $C_{1-6}$ alkyl, and $C_{3-6}$ cycloalkyl;

alternatively, two $R^{5f}$s, together with the N to which they are attached, join to form a 3-8 membered heterocycle containing 0-1 additional heteroatoms selected from N, O and S;

$R^6$, at each occurrence, is selected from $C_{1-8}$ alkyl, $C_{2-8}$ alkenyl, $C_{2-8}$ alkynyl, $(CR'R')_rC_{3-6}$ cycloalkyl, Cl, Br, I, F, $NO_2$, CN, $(CR'R')_rNR^{6a}R^{6a}$, $(CR'R')_rOH$, $(CR'R')_rO$ $(CR'R')_rSH$, $(CR'R')_rS^{6d}$, $(CR'R')_rSC(O)H$, $(CR'R')_rS$ $(CR'R')_rR^{6d}$, $(CR'R')_rSC(O)(CR'R')_rR^{6a}$, $(CR'R')_rC(O)$ OH, $(CR'R')_rC(O)(CR'R')_rR^{6a}$, $(CR'R')_rC(O)NR^{6a}R^{6a}$, $(CR'R')_rNR^{6f}C(O)(CR'R')_rR^{6a}$, $(CR'R')_rC(O)O$ $(CR'R')_r$ $R^{6d}$, $(CR'R')_rOC(O)(CR'R')_rR^{6a}$, $(CR'R')_rOC$ $(O)NR^{6a}(CR'R')_rR^{6d}$, $(CR'R')_rNR^{6a}C(O)NR^{6a}(CR'R')_r$ $R^{6d}$, $(CR'R')_rNR^{6a}C(S)NR^{6a}(CR'R')_rR^{6d}$, $(CR'R')_r$ $NR^{6f}C(O)O(CR'R')_rR^{6a}$, $(CR'R')_rC(=NR^{6f})NR^{6a}R^{6a}$, $(CR'R')_rNHC(=NR^{6f})NR^{6f}R^{6f}$, $(CR'R')_rS(O)_p(CR'R')_r$ $R^{6a}$, $(CR'R')_rS(O)_2NR^{6a}R^{6a}$, $(CR'R')_rNR^{6f}S(O)_2$ $NR^{6a}R^{6a}$, $(CR'R')_rNR^{6f}S(O)_2(CR'R')_rR^{6a}$, $C_{1-6}$ haloalkyl, $C_{2-8}$ alkenyl substituted with 0-3 R', $C_{2-8}$ alkynyl substituted with 0-3 R', $(CR'R')_r$phenyl substituted with 0-3 $R^{6e}$, and a $(CR'R')_r$-5-6 membered heterocyclic system containing 1-2 heteroatoms selected from N, O, and S, substituted with 0-2 $R^{6e}$;

alternatively, two $R^6$s on adjacent atoms on $R^1$ may join to form a cyclic acetal;

$R^{6a}$, at each occurrence, is selected from H, methyl, $C_{2-6}$ alkyl substituted with 0-2 $R^{6e}$, $C_{3-8}$ alkenyl substituted with 0-2 $R^{6e}$, $C_{3-8}$ alkynyl substituted with 0-2 $R^{6e}$, a $(CR'R')$—$C_{3-10}$ carbocyclic residue substituted with 0-5 $R^{6e}$, and a $(CR'R')_r$-5-10 membered heterocyclic system containing 1-4 heteroatoms selected from N, O, and S, substituted with 0-2 $R^{6e}$;

alternatively, two $R^{6a}$s, together with the N to which they are attached, join to form a 3-8 membered heterocycle containing 0-1 additional heteroatoms selected from N, O, and S;

$R^{6d}$, at each occurrence, is selected from $C_{3-8}$ alkenyl substituted with 0-2 $R^{6e}$, $C_{3-8}$ alkynyl substituted with 0-2 $R^{6e}$, methyl, $CF_3$, $C_{2-6}$ alkyl substituted with 0-3 $R^{6e}$, $C_{2-4}$ haloalkyl, a $(CR'R')_r$—$C_{3-10}$ carbocyclic residue substituted with 0-3 $R^{6e}$, and a $(CR'R')_r$-5-6 membered heterocyclic system containing 1-4 heteroatoms selected from N, O, and S, substituted with 0-3 $R^{6e}$;

$R^{6e}$, at each occurrence, is selected from $C_{1-6}$ alkyl, $C_{2-8}$ alkenyl, $C_{2-8}$ alkynyl, $(CR'R')_rC_{3-6}$ cycloalkyl, Cl, F, Br, I, CN, $NO_2$, $(CF_2)_rCF_3$, $(CR'R')_rOC_{1-5}$ alkyl, OH, SH, $(CR'R')_rSC_{1-5}$ alkyl, $(CR'R')_rNR^{6f}R^{6f}$, and $(CR'R')_r$phenyl;

$R^{6f}$, at each occurrence, is selected from H, $C_{1-5}$ alkyl, and $C_{3-6}$ cycloalkyl, and phenyl;

alternatively, two $R^{6f}$s, together with the N to which they are attached, join to form a 3-8 membered heterocycle containing 0-1 additional heteroatoms selected from N, O and S;

$R^7$, at each occurrence, is selected from $C_{1-8}$ alkyl, $C_{2-8}$ alkenyl, $C_{2-8}$ alkynyl, $(CR'R')_rC_{3-6}$ cycloalkyl, Cl, Br, I, F, $NO_2$, CN, $(CR'R')_rNR^{7a}R^{7a}$, $(CR'R')_rOH$, $(CR'R')_rO$ $(CR'R')_rR^{7d}$, $(CR'R')_rSH$, $(CR'R')_rC(O)H$, $(CR'R')_rS$ $(CR'R')_rR^{7d}$, $(CR'R')_rC(O)OH$, $(CR'R')_rC(O)(CR'R')_r$ $R^{7b}$, $(CR'R')_rC(O)NR^{7a}R^{7a}$, $(CR'R')_rNR^{7f}C(O)$ $(CR'R')_r$ $R^{7b}$, $(CR'R')_rC(O)O(CR'R')_rR^{7d}$, $(CR'R')_rOC$ $(O)(CR'R')_rR^{7b}$, $(CR'R')_rOC(O)NR^{7a}(CR'R')_rR^{7a}$, $(CR'R')_r$ $NR^{7a}C(O)NR^{7a}(CR'R')_rR^{7a}$, $(CR'R')_rNR^{7f}C$ $(O)O(CR'R')_rR^{7d}$, $(CR'R')_rC(=NR^{7f})NR^{7a}R^{7a}$, $(CR'R')_r$ $NHC(=NR^{7f})NR^{7f}R^{7f}$, $(CR'R')_rS(O)_p$ $(CR'R')_r$ $R^{7b}$, $(CR'R')_rS(O)_2NR^{7a}R^{7a}$, $(CR'R')_rNR^{7a}S$ $(O)_2$ $NR^{7a}R^{7a}$, $(CR'R')_rNR^{7f}S(O)_2(CR'R')_rR^{7b}$, $C_{1-6}$ haloalkyl, $C_{2-8}$ alkenyl substituted with 0-3 R', $C_{2-8}$ alkynyl substituted with 0-3 R', a $(CR'R')_r$—$C_{3-10}$ carbocyclic residue substituted with 0-3 $R^{7e}$, and a $(CR'R')_r$-5-10 membered heterocyclic system containing 1-4 heteroatoms selected from N, O, and S, substituted with 0-3 $R^{7e}$;

alternatively, two $R^7$s on adjacent atoms on $R^2$ may join to form a cyclic acetal;

$R^{7a}$, at each occurrence, is independently selected from H, methyl substituted with 0-1 $R^{7g}$, $C_{2-6}$ alkyl substituted with 0-2 $R^{7e}$, $C_{3-8}$ alkenyl substituted with 0-2 $R^{7e}$, $C_{3-8}$ alkynyl substituted with 0-2 $R^{7e}$, a $(CR'R')_r$—$C_{3-10}$ carbocyclic residue substituted with 0-5 $R^{7e}$, and a $(CR'R')_r$-5-10 membered heterocyclic system containing 1-4 heteroatoms selected from N, O, and S, substituted with 0-2 $R^{7e}$;

alternatively, two $R^{7a}$s, together with the N to which they are attached, join to form a 3-8 membered heterocycle containing 0-1 additional heteroatoms selected from N, O and S;

$R^{7b}$, at each occurrence, is selected from $C_{1-6}$ alkyl substituted with 0-2 $R^{7e}$, $C_{3-8}$ alkenyl substituted with 0-2 $R^{7e}$, $C_{3-8}$ alkynyl substituted with 0-2 $R^{7e}$, a $(CR'R')_rC_{3-6}$ carbocyclic residue substituted with 0-3 $R^{7e}$, and a $(CR'R')_r$-4-6 membered heterocyclic system containing 1-4 heteroatoms selected from N, O, and S, substituted with 0-2 $R^{7e}$;

$R^{7d}$, at each occurrence, is selected from $C_{3-8}$ alkenyl substituted with 0-2 $R^{7e}$, $C_{3-8}$ alkynyl substituted with 0-2 $R^{7e}$, methyl, $CF_3$, $C_{2-4}$ haloalkyl, $C_{2-6}$ alkyl substituted with 0-3 $R^{7e}$, a $(CR'R')_r$—$C_{3-10}$ carbocyclic residue substituted with 0-3 $R^{7e}$, and a $(CR'R')_r$-5-6 membered heterocyclic system containing 1-4 heteroatoms selected from N, O, and S, substituted with 0-3 $R^{7e}$;

$R^{7e}$, at each occurrence, is selected from $C_{1-6}$ alkyl, $C_{2-8}$ alkenyl, $(CR'R')_r$cyclopropyl, Cl, F, Br, CN, $(CF_2)_rCF_3$, $(CR'R')_rOC_{1-5}$ alkyl, OH, $C(O)OC_{1-5}$ alkyl, $(CR'R')_r$ $NR^{7f}R^{7f}$, and acetyl;

$R^{7f}$, at each occurrence, is selected from H, $C_{1-5}$ alkyl, and $C_{3-6}$ cycloalkyl, and phenyl;

alternatively, two $R^{7f}$s, together with the N to which they are attached, join to form a 3-8 membered heterocycle containing 0-1 additional heteroatoms selected from N, O and S;

$R^{7g}$ is independently selected from —$C(O)R^{7b}$, —$C(O)$ $OR^{7d}$, —$C(O)NR^{7f}R^{7f}$, and $(CR'R')_r$phenyl;

R', at each occurrence, is independently selected from H, methyl, and $C_{2-6}$ alkyl;

alternatively, two R's, along with the carbon atom to which they are attached, join to form a cyclopropyl ring;

$R^8$ is selected from H, $C_{1-4}$ alkyl, and $C_{3-4}$ cycloalkyl;

$R^{10}$ and $R^{10a}$ are independently selected from H and $C_{1-4}$ alkyl substituted with 0-1 $R^{10b}$, $R^{10b}$, at each occurrence, is independently selected from —OH, —SH, —$NR^{10c}R^{10c}$, —$C(O)NR^{10c}R^{10c}$, and —$NHC(O)R^{10c}$;

$R^{10c}$ is selected from H, $C_{1-4}$ alkyl and $C_{3-6}$ cycloalkyl;

alternatively, two $R^{10c}$S, together with the N to which they are attached, join to form a 3-8 membered heterocycle containing 0-1 additional heteroatoms selected from N, O and S;

$R^{12}$ is selected from H and $C_{1-4}$ alkyl;

$R^{14}$, at each occurrence, is independently selected from H and $C_{1-4}$alkyl;

alternatively, two $R^{14}$s, along with the carbon atom to which they are attached, join to form a $C_{3-6}$ carbocyclic ring;

$R^{25}$, at each occurrence, is independently selected from H, $C_{1-4}$alkyl, OH, $NH_2$, —O—$C_{1-4}$ alkyl, $NR^{25a}R^{25a}$, C(O)NR$^{25a}$R$^{25a}$, NR$^{25a}$C(O)R$^{25b}$, NR$^{25a}$C(O)OR$^{25b}$, OC(O)NR$^{25a}$R$^{25a}$, and (CHR)$_r$C(O)OR$^{25b}$;

alternatively, two R$^{25}$s, along with the carbon atom or atoms to which they are attached, join to form a C$_{3-6}$ carbocyclic ring;

R$^{25a}$, at each occurrence, is independently selected from H, and C$_{1-4}$ alkyl;

alternatively, two R$^{25a}$s, together with the N to which they are attached, join to form a 3-8 membered heterocycle containing 0-1 additional heteroatoms selected from N, O and S;

R$^{25b}$, at each occurrence, is independently selected from H, C$_{1-4}$ alkyl, C$_{3-6}$ alkenyl, and C$_{3-6}$ alkynyl;

a is selected from 0 and 1;

b is selected from 0, 1, 2 and 3;

with the proviso that a+b is selected from 1, 2 and 3;

c is 1;

d is 1;

with the proviso that c+d is 2;

n is selected from 1 and 2;

p, at each occurrence, is independently selected from 0, 1, and 2;

q, at each occurrence, is independently selected from 1, 2, 3, and 4;

r, at each occurrence, is independently selected from 0, 1, 2, 3, and 4; and u is selected from 1, 2 and 3.

2. The compound of claim 1, wherein

X is O;

Z is selected from a bond, —C(O)NR$^8$—, —NR$^8$—, —NR$^8$C(O)—, —NR$^8$C(O)NH—, —NR$^8$SO$_2$—, —(CR$^{25}$R$^{25}$)$_u$—, —CR$^{14}$=CR$^{14}$—, and —CR$^{25}$R$^{25}$C(O)—;

R$^1$ is selected from H, R$^6$, C$_{1-6}$ alkyl substituted with 0-3 R$^6$, C$_{6-10}$ aryl group substituted with 0-5 R$^6$, and a 5-10 membered heteroaryl system containing 1-4 heteroatoms selected from N, O, and S, substituted with 0-3 R$^6$;

R$^2$ is selected from a C$_{6-10}$ aryl group substituted with 0-5 R$^7$ and a 5-10 membered heteroaryl system containing 1-4 heteroatoms selected from N, O, and S, substituted with 0-3 R$^7$;

R$^3$ is selected from H and methyl;

R$^4$ is absent, taken with the nitrogen to which it is attached to form an N-oxide, or C$_{1-8}$ alkyl;

R$^5$ is selected from H and C$_{1-6}$ alkyl substituted with 0-2 R$^{5e}$;

R$^{5e}$, at each occurrence, is selected from C$_{1-6}$ alkyl, C$_{2-8}$ alkenyl, C$_{2-8}$ alkynyl, C$_{3-6}$ cycloalkyl, F, (CF$_2$)$_r$CF$_3$, (CR'R')$_r$OC$_{1-5}$ alkyl, and (CR'R')$_r$NR$^{5f}$R$^{5f}$;

R$^{5f}$, at each occurrence, is selected from H and C$_{1-6}$ alkyl;

alternatively, two R$^{5f}$s, together with the N to which they are attached, join to form a 3-8 membered heterocycle containing 0-1 additional heteroatoms selected from N, O and S;

R$^6$, at each occurrence, is selected from C$_{1-8}$ alkyl, C$_{2-8}$ alkenyl, C$_{2-8}$ alkynyl, (CR'R')$_r$C$_{3-6}$ cycloalkyl, (CR'R')$_r$NR$^{6a}$R$^{6a}$, (CR'R')$_r$OH, (CR'R')$_r$O(CR'R')$_r$R$^{6d}$, (CR'R')$_r$S(CR'R')$_r$R$^{6d}$, (CR'R')$_r$C(O)(CR'R')$_r$R$^{6a}$, (CR'R')$_r$C(O)NR$^{6a}$R$^{6a}$, (CR'R')$_r$NR$^{6f}$C(O)(CR'R')$_r$R$^{6a}$, (CR'R')$_r$C(O)O(CR'R')$_r$R$^{6d}$, (CR'R')$_r$OC(O)(CR'R')$_r$R$^{6a}$, (CR'R')$_r$OC(O)NR$^{6a}$(CR'R')$_r$R$^{6d}$, (CR'R')$_r$NR$^{6a}$C(O)NR$^{6a}$(CR'R')$_r$R$^{6d}$, (CR'R')$_r$NR$^{6f}$C(O)O(CR'R')$_r$R$^{6a}$, (CR'R')$_r$S(O)$_p$(CR'R')$_r$R$^{6a}$, (CR'R')$_r$S(O)$_2$NR$^{6a}$R$^{6a}$, (CR'R')$_r$NR$^{6f}$S(O)$_2$NR$^{6a}$R$^{6a}$, (CR'R')$_r$NR$^{6f}$S(O)$_2$(CR'R')$_r$R$^{6a}$, C$_{1-6}$ haloalkyl, (CR'R')$_r$phenyl substituted with 0-3 R$^{6e}$, and a (CR'R')$_r$-5-6 membered heterocyclic system containing 1-2 heteroatoms selected from N, O, and S, substituted with 0-2 R$^{6e}$;

R$^{6a}$, at each occurrence, is selected from H, methyl, C$_{2-6}$ alkyl substituted with 0-2 R$^{6e}$, C$_{3-8}$ alkenyl substituted with 0-2 R$^{6e}$, C$_{3-8}$ alkynyl substituted with 0-2 R$^{6e}$, a (CR'R')$_r$—C$_{3-10}$ carbocyclic residue substituted with 0-5 R$^{6e}$, and a (CR'R')$_r$-5-10 membered heterocyclic system containing 1-4 heteroatoms selected from N, O, and S, substituted with 0-2 R$^{6e}$;

alternatively, two R$^{6a}$s, together with the N to which they are attached, join to form a 3-8 membered heterocycle containing 0-1 additional heteroatoms selected from N, O, and S;

R$^{6d}$, at each occurrence, is selected from methyl, CF$_3$, C$_{2-6}$ alkyl substituted with 0-3 R$^{6e}$, a (CR'R')$_r$—C$_{3-10}$ carbocyclic residue substituted with 0-3 R$^{6e}$, and a (CR'R')$_r$-5-6 membered heterocyclic system containing 1-4 heteroatoms selected from N, O, and S, substituted with 0-3 R$^{6e}$;

R$^{6e}$, at each occurrence, is selected from C$_{1-6}$ alkyl, Cl, F, (CF$_2$)$_r$CF$_3$, and (CR'R')$_r$OC$_{1-5}$ alkyl;

R$^{6f}$, at each occurrence, is selected from H and C$_{1-5}$ alkyl;

R$^7$, at each occurrence, is selected from C$_{1-8}$ alkyl, Cl, Br, F, CN, (CR'R')$_r$NR$^{7a}$R$^{7a}$, (CR'R')$_r$OH, (CR'R')$_r$O(CR'R')$_r$R$^{7d}$, (CR'R')$_r$C(O)(CR'R')$_r$R$^{7b}$, (CR'R')$_r$C(O)NR$^{7a}$R$^{7a}$, (CR'R')$_r$NR$^{7f}$C(O)(CR'R')$_r$R$^{7b}$, (CR'R')$_r$OC(O)NR$^{7a}$(CR'R')$_r$R$^{7a}$, (CR'R')$_r$NR$^{7a}$C(O)NR$^{7a}$(CR'R')$_r$R$^{7a}$, (CR'R')$_r$NR$^{7f}$C(O)O(CR'R')$_r$R$^{7d}$, (CR'R')$_r$S(O)$_p$(CR'R')$_r$R$^{7b}$, (CR'R')$_r$S(O)$_2$NR$^{7a}$R$^{7a}$, (CR'R')$_r$NR$^{7a}$S(O)$_2$NR$^{7a}$R$^{7a}$, (CR'R')$_r$NR$^{7f}$S(O)$_2$(CR'R')$_r$R$^{7b}$, C$_{1-6}$ haloalkyl, a (CR'R')$_r$—C$_{3-10}$ carbocyclic residue substituted with 0-3 R$^{7e}$, and a (CR'R')$_r$-5-10 membered heterocyclic system containing 1-4 heteroatoms selected from N, O, and S, substituted with 0-3 R$^{7e}$;

R$^{7a}$, at each occurrence, is independently selected from H, methyl substituted with 0-1 R$^{7g}$, C$_{2-6}$ alkyl substituted with 0-2 R$^{7e}$, a (CR'R')$_r$—C$_{3-10}$ carbocyclic residue substituted with 0-5 R$^{7e}$, and a (CR'R')$_r$-5-10 membered heterocyclic system containing 1-4 heteroatoms selected from N, O, and S, substituted with 0-2 R$^{7e}$;

alternatively, two R$^{7a}$s, together with the N to which they are attached, join to form a 3-8 membered heterocycle containing 0-1 additional heteroatoms selected from N, O and S;

R$^{7b}$, at each occurrence, is selected from C$_{1-6}$ alkyl substituted with 0-2 R$^{7e}$, C$_{3-8}$ alkenyl substituted with 0-2 R$^{7e}$, a (CR'R')$_r$C$_{3-6}$ carbocyclic residue substituted with 0-3 R$^{7e}$, and a (CR'R')$_r$-4-6 membered heterocyclic system containing 1-4 heteroatoms selected from N, O, and S, substituted with 0-2 R$^{7e}$;

R$^{7d}$, at each occurrence, is selected from methyl, C$_{2-6}$ alkyl substituted with 0-3 R$^{7e}$, a (CR'R')$_r$—C$_{3-10}$ carbocyclic residue substituted with 0-3 R$^{7e}$, and a (CR'R')$_r$-5-6 membered heterocyclic system containing 1-4 heteroatoms selected from N, O, and S, substituted with 0-3 R$^{7e}$;

R$^{7e}$, at each occurrence, is selected from C$_{1-6}$ alkyl, C$_{2-8}$ alkenyl, Cl, F, Br, CN, (CF$_2$)$_r$CF$_3$, (CR'R')$_r$OC$_{1-5}$ alkyl, OH, C(O)OC$_{1-5}$ alkyl, (CR'R')$_r$NR$^{7f}$R$^{7f}$, and acetyl;

R$^{7f}$, at each occurrence, is selected from H and C$_{1-5}$ alkyl;

alternatively, two R$^{7f}$s, together with the N to which they are attached, join to form a 3-8 membered heterocycle containing 0-1 additional heteroatoms selected from N, O and S;

R$^{7g}$ is independently selected from —C(O)R$^{7b}$, —C(O)OR$^{7d}$, —C(O)NR$^{7f}$R$^{7f}$, and (CR'R')$_r$phenyl;

R', at each occurrence, is independently, selected from H, methyl, and $C_{2-6}$ alkyl;

$R^8$ is selected from H, $C_{1-4}$ alkyl, and $C_{3-4}$ cycloalkyl;

$R^{10}$ and $R^{10a}$ are independently selected from H and $C_{1-4}$ alkyl substituted with 0-1 $R^{10b}$, $R^{10b}$, at each occurrence, is independently selected from —OH, —SH, —NR$^{10c}$R$^{10c}$, —C(O)NR$^{10c}$R$^{10c}$, and —NHC(O)R$^{10c}$;

$R^{10c}$ is selected from H, $C_{1-4}$ alkyl and $C_{3-6}$ cycloalkyl;

alternatively, two $R^{10c}$s, together with the N to which they are attached, join to form a 3-8 membered heterocycle containing 0-1 additional heteroatoms selected from N, O and S;

$R^{12}$ is selected from H and $C_{1-4}$ alkyl;

$R^{14}$, at each occurrence, is independently selected from H and $C_{1-4}$alkyl;

alternatively, two $R^{14}$s, along with the carbon atom to which they are attached, join to form a $C_{3-6}$carbocyclic ring;

$R^{25}$, at each occurrence, is independently selected from H, $C_{1-4}$alkyl, OH, NH$_2$, —O—$C_{1-4}$ alkyl, NR$^{25a}$R$^{25a}$, C(O)NR$^{25a}$R$^{25a}$, NR$^{25a}$C(O)R$^{25b}$, NR$^{25a}$C(O)OR$^{25b}$, OC(O)NR$^{25a}$R$^{25a}$, and (CHR)$_r$C(O)OR$^{25b}$;

alternatively, two $R^{25}$s, along with the carbon atom or atoms to which they are attached, join to form a $C_{3-6}$ carbocyclic ring;

$R^{25a}$, at each occurrence, is independently selected from H, and $C_{1-4}$ alkyl, alternatively, two $R^{25a}$s, together with the N to which they are attached, join to form a 3-8 membered heterocycle containing 0-1 additional heteroatoms selected from N, O and S;

$R^{25b}$, at each occurrence, is independently selected from H, $C_{1-4}$ alkyl, $C_{3-6}$ alkenyl, and $C_{3-6}$ alkynyl;

a is selected from 0 and 1;

b is selected from 0 and 1;

with the proviso that a+b is selected from 1 and 2;

c is 1;

d is 1;

with the proviso that c+d is 2;

n is selected from 1 and 2;

p, at each occurrence, is independently selected from 0, 1, and 2;

q, at each occurrence, is independently selected from 1 and 2;

r, at each occurrence, is independently selected from 0, 1, and 2; and u is selected from 1, 2 and 3.

3. The compound of claim 2, wherein

X is O;

Z is selected from a bond, —C(O)NR$^8$—, —NR$^8$— and —NR$^8$C(O)—;

$R^1$ is selected from H, $R^6$, and $C_{1-6}$ alkyl substituted with 0-3 $R^6$;

$R^2$ is selected from a $C_{6-10}$ aryl group substituted with 0-5 $R^7$, wherein the aryl group is selected from phenyl and naphthyl, and a 5-10 membered heteroaryl system containing 1-4 heteroatoms selected from N, O, and S, substituted with 0-3 $R^7$, wherein the heteroaryl is selected from indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolinyl, isoxazolyl, oxazolyl, phthalazinyl, pyrazinyl, pyrazolyl, pyrazolotriazinyl, pyridazinyl, pyridyl, pyridinyl, pyrimidinyl, pyrrolyl, quinazolinyl, quinolinyl, thiazolyl, thienyl, and tetrazolyl;

$R^3$ is H;

$R^4$ is absent, taken with the nitrogen to which it is attached to form an N-oxide, or $C_{1-8}$ alkyl;

$R^5$ is selected from H and $C_{1-6}$ alkyl;

$R^6$, at each occurrence, is selected from $C_{1-8}$ alkyl, (CR'R')$_r$NR$^{6a}$R$^{6a}$, (CR'R')$_r$OH, (CR'R')$_r$O(CR'R')$_r$R$^{6d}$, (CR'R')$_r$C(O)(CR'R')$_r$R$^{6a}$, (CR'R')$_r$C(O)NR$^{6a}$R$^{6a}$, (CR'R')$_r$NR$^{6f}$C(O)(CR'R')$_r$R$^{6a}$, and (CR'R')$_r$S(O)$_p$(CR'R')$_r$R$^{6a}$;

$R^{6a}$, at each occurrence, is selected from H, methyl, $C_{2-6}$ alkyl substituted with 0-2 $R^{6e}$, $C_{3-8}$ alkenyl substituted with 0-2 $R^{6e}$, $C_{3-8}$ alkynyl substituted with 0-2 $R^{6e}$, a (CR'R')$_r$—$C_{3-10}$ carbocyclic residue substituted with 0-5 $R^{6e}$, and a (CR'R')$_r$-5-10 membered heterocyclic system containing 1-4 heteroatoms selected from N, O, and S, substituted with 0-2 $R^{6e}$;

alternatively, two $R^{6a}$s, together with the N to which they are attached, join to form a 3-8 membered heterocycle containing 0-1 additional heteroatoms selected from N, O and S;

$R^{6d}$, at each occurrence, is selected from methyl and $C_{2-6}$ alkyl substituted with 0-3 $R^{6e}$;

$R^{6e}$, at each occurrence, is selected from $C_{1-6}$ alkyl, Cl, F, (CF$_2$)$_r$CF$_3$, and (CR'R')$_r$OC$_{1-5}$ alkyl;

$R^{6f}$, at each occurrence, is selected from H and $C_{1-5}$ alkyl;

$R^7$, at each occurrence, is selected from $C_{1-8}$ alkyl, Cl, Br, F, CN, (CR'R')$_r$NR$^{7a}$R$^{7a}$, (CR'R')$_r$OH, (CR'R')$_r$O(CR'R')$_r$R$^{7d}$, (CR'R')$_r$C(O)(CR'R')$_r$R$^{7b}$, (CR'R')$_r$C(O)NR$^{7a}$R$^{7a}$, (CR'R')$_r$NR$^{7f}$C(O)(CR'R')$_r$R$^{7b}$, (CR'R')$_r$OC(O)NR$^{7a}$(CR'R')$_r$R$^{7a}$, (CR'R')$_r$NR$^{7a}$C(O)NR$^{7a}$(CR'R')$_r$R$^{7a}$, (CR'R')$_r$NR$^{7f}$C(O)O(CR'R')$_r$R$^{7d}$, (CR'R')$_r$S(O)$_p$(CR'R')$_r$R$^{7b}$, (CR'R')$_r$S(O)$_2$NR$^{7a}$R$^{7a}$, (CR'R')$_r$NR$^{7f}$S(O)$_2$(CR'R')$_r$R$^{7b}$, $C_{1-6}$ haloalkyl, and a (CR'R')$_r$—$C_{3-10}$ carbocyclic residue substituted with 0-3 $R^{7e}$;

$R^{7a}$, at each occurrence, is independently selected from H, methyl, $C_{2-6}$ alkyl, a (CR'R')$_r$—$C_{3-10}$ carbocyclic residue substituted with 0-5 $R^{7e}$, and a (CR'R')$_r$-5-10 membered heterocyclic system containing 1-4 heteroatoms selected from N, O, and S, substituted with 0-2 $R^{7e}$;

alternatively, two $R^{7a}$s, together with the N to which they are attached, join to form a 3-8 membered heterocycle containing 0-1 additional heteroatoms selected from N, O and S;

$R^{7b}$, at each occurrence, is selected from $C_{1-6}$ alkyl, $C_{3-8}$ alkenyl, a (CR'R')$_r$C$_{3-6}$ carbocyclic residue substituted with 0-3 $R^{7e}$, and a (CR'R')$_r$-4-6 membered heterocyclic system containing 1-4 heteroatoms selected from N, O, and S, substituted with 0-2 $R^{7e}$;

$R^{7d}$, at each occurrence, is selected from methyl, $C_{2-6}$ alkyl, a (CR'R')$_r$—$C_{3-10}$ carbocyclic residue substituted with 0-3 $R^{7e}$, and a (CR'R')$_r$-5-6 membered heterocyclic system containing 1-4 heteroatoms selected from N, O, and S, substituted with 0-3 $R^{7e}$;

$R^{7e}$, at each occurrence, is selected from $C_{1-6}$ alkyl, $C_{2-8}$ alkenyl, Cl, F, Br, CN, (CF$_2$)$_r$CF$_3$, (CR'R')$_r$OC$_{1-5}$ alkyl, C(O)OC$_{1-5}$ alkyl, (CR'R')$_r$NR$^{7f}$R$^{7f}$, and acetyl;

$R^{7f}$, at each occurrence, is selected from H and $C_{1-4}$ alkyl;

R', at each occurrence, is independently, selected from H and methyl;

$R^8$ is H;

$R^{10}$ and $R^{10a}$ are independently selected from H and $C_{1-4}$ alkyl;

$R^{12}$ is H;

$R^{14}$, at each occurrence, is H;

$R^{25}$, at each occurrence, is independently selected from H, OH, and $NH_2$;

a is 1;
b is 0;
c is 1;
d is 1;
n is 1;
p, at each occurrence, is independently selected from 0, 1, and 2;
q, at each occurrence, is 1;
r, at each occurrence, is independently selected from 0 and 1; and
u is selected from 1 and 2.

4. The compound of claim 3, wherein

X is O;
Z is selected from a bond and —$NR^8$—;
$R^1$ is selected from H, $R^6$, and $C_{1-6}$ alkyl substituted with 0-2 $R^6$;
$R^2$ is a 5-10 membered heteroaryl system containing 1-4 heteroatoms selected from N, O, and S, substituted with 0-3 $R^7$, wherein the heteroaryl is selected from indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolinyl, isoxazolyl, oxazolyl, phthalazinyl, pyrazinyl, pyrazolyl, pyrazolotriazinyl, pyridazinyl, pyridyl, pyridinyl, pyrimidinyl, pyrrolyl, quinazolinyl, quinolinyl, thiazolyl, thienyl, and tetrazolyl;
$R^3$ is H;
$R^4$ is absent, taken with the nitrogen to which it is attached to form an N-oxide, or $C_{1-8}$ alkyl;
$R^5$ is selected from H and $C_{1-6}$ alkyl;
$R^6$, at each occurrence, is selected from $C_{1-4}$ alkyl, $(CH_2)_r NR^{6a}R^{6a}$, $(CH_2)_r OH$, $(CH_2)_r O(CH_2)_r R^{6d}$, $(CH_2)_r C(O)(CH_2)_r R^{6a}$, $(CH_2)_r C(O)NR^{6a}R^{6a}$, $(CH_2)_r NR^{6f}C(O)(CH_2)_r R^{6a}$, and $(CH_2)_r S(O)_p(CH_2)_r R^{6a}$;
$R^{6a}$, at each occurrence, is selected from H, $C_{1-4}$ alkyl, phenyl substituted with 0-3 $R^{6e}$, and a 5-10 membered heterocyclic system containing 1-4 heteroatoms selected from N, O, and S, substituted with 0-2 $R^{6e}$;
alternatively, two $R^{6a}$s, together with the N to which they are attached, join to form a heterocycle wherein the heterocycle is selected from azetidinyl, pyrrolyl, piperidinyl, and morpholinyl;
$R^{6d}$, at each occurrence, is selected from $C_{1-4}$ alkyl;
$R^{6e}$, at each occurrence, is selected from $C_{1-4}$ alkyl, Cl, F, $(CF_2)_r CF_3$, and $(CH_2)_r OC_{1-4}$ alkyl;
$R^{6f}$, at each occurrence, is selected from H, methyl and ethyl;
$R^7$ is selected from $C_{1-6}$ alkyl, phenyl substituted with 0-3 $R^{7e}$, Cl, Br, I, F, CN, $NO_2$, $NR^{7a}R^{7a}$, $NHC(O)NHR^{7a}$, $NR^{7a}C(O)R^{7b}$, $NR^{7a}C(O)OR^{7d}$, $CF_3$, $CF_2CF_3$, $CHF_2$, $CH_2F$, $OCF_3$, $C(O)R^{7b}$, $C(O)OR^{7d}$, $NHC(O)NR^{7a}R^{7a}$, $NHS(O)_2R^{7b}$,

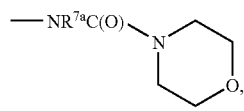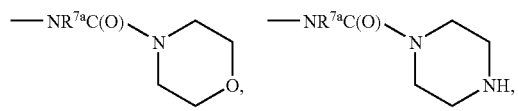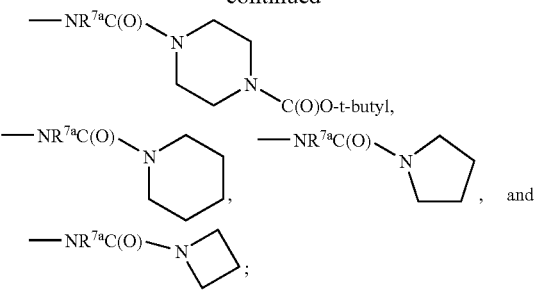

$R^{7a}$, at each occurrence, is independently selected from H and $C_{1-4}$ alkyl;
alternatively, two $R^{7a}$s, together with the N to which they are attached, join to form a heterocycle wherein the heterocycle is selected from azetidinyl, pyrrolyl, piperidinyl, and morpholinyl;
$R^{7b}$, at each occurrence, is selected from $C_{1-6}$ alkyl, a $(CH_2)_r$-$C_{3-6}$ carbocyclic residue substituted with 0-3 $R^{7e}$, and a $(CH_2)_r$-5-6 membered heterocyclic system containing 1-4 heteroatoms selected from N, O, and S, substituted with 0-2 $R^{7e}$;
$R^{7d}$, at each occurrence, is selected from $C_{1-6}$ alkyl, a $(CH_2)_r$-$C_{3-6}$ carbocyclic residue substituted with 0-3 $R^{7e}$, and a $(CH_2)_r$-5-6 membered heterocyclic system containing 1-4 heteroatoms selected from N, O, and S, substituted with 0-2 $R^{7e}$;
$R^{7e}$, at each occurrence, is selected from $C_{1-6}$ alkyl, Cl, F, Br, CN, $(CF_2)_r CF_3$, $(CH_2)_r OC_{1-4}$ alkyl, $C(O)OC_{1-4}$ alkyl, $(CH_2)_r NR^{7f}R^{7f}$, and acetyl;
R7f, at each occurrence, is selected from H, and $C_{1-4}$ alkyl;
$R^8$ is H;
$R^{10}$ and $R^{10a}$ are independently selected from H and $C_{1-4}$ alkyl;
$R^{12}$ is H;
$R^{14}$, at each occurrence, is H;
a is 1;
b is 0;
c is 1;
d is 1;
n is 1;
p, at each occurrence, is independently selected from 0, 1, and 2; and
r, at each occurrence, is independently selected from 0 and 1.

5. The compound of claim 3, wherein

X is O;
Z is selected from —$C(O)NR^8$- and —$NR^8C(O)$—;
$R^1$ is selected from H, $R^6$, and $C_{1-6}$ alkyl substituted with 0-2 $R^6$;
$R^2$ is selected from a $C_{6-10}$ aryl group substituted with 0-3 $R^7$, wherein the aryl group is selected from phenyl and naphthyl, and a 5-10 membered heteroaryl system containing 1-4 heteroatoms selected from N, O, and S, substituted with 0-3 $R^7$, wherein the heteroaryl is selected from indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolinyl, isoxazolyl, oxazolyl, phthalazinyl, pyrazinyl, pyrazolyl, pyrazolotriazinyl, pyridazinyl, pyridyl, pyridinyl, pyrimidinyl, pyrrolyl, quinazolinyl, quinolinyl, thiazolyl, thienyl, and tetrazolyl;

$R^3$ is H;

$R^4$ is absent, taken with the nitrogen to which it is attached to form an N-oxide, or $C_{1-8}$ alkyl;

$R^5$ is selected from H and $C_{1-6}$ alkyl;

$R^6$, at each occurrence, is selected from $C_{1-4}$ alkyl, $(CH_2)_r NR^{6a}R^{6a}$, $(CH_2)_rOH$, $(CH_2)_rO(CH_2)_rR^{6d}$, $(CH_2)_rC(O)(CH_2)_rR^{6a}$, $(CH_2)_rC(O)NR^{6a}R^{6a}$, $(CH_2)_rNR^{6f}C(O)(CH_2)_rR^{6a}$, and $(CH_2)_rS(O)_p(CH_2)_rR^{6a}$;

$R^{6a}$, at each occurrence, is selected from H, $C_{1-4}$ alkyl, phenyl substituted with 0-3 $R^{6e}$, and a 5-10 membered heterocyclic system containing 1-4 heteroatoms selected from N, O, and S, substituted with 0-2 $R^{6e}$;

alternatively, two $R^{6a}$s, together with the N to which they are attached, join to form a heterocycle wherein the heterocycle is selected from azetidinyl, pyrrolyl, piperidinyl, and morpholinyl;

$R^{6d}$, at each occurrence, is selected from $C_{1-4}$ alkyl;

$R^{6e}$, at each occurrence, is selected from $C_{1-4}$ alkyl, Cl, F, $(CF_2)_rCF_3$, and $(CH_2)_rOC_{1-4}$ alkyl;

$R^{6f}$, at each occurrence, is selected from H, methyl and ethyl;

$R^7$ is selected from $C_{1-6}$ alkyl, phenyl substituted with 0-3 $R^{7e}$, Cl, Br, I, F, CN, $NO_2$, $NR^{7a}R^{7a}$, $NHC(O)NHR^{7a}$, $NR^{7a}C(O)R^{7b}$, $NR^{7a}C(O)OR^{7d}$, $CF_3$, $CF_2CF_3$, $CHF_2$, $CH_2F$, $OCF_3$, $C(O)R^{7b}$, $C(O)OR^{7d}$, $NHC(O)NR^{7a}R^{7a}$, $NHS(O)_2R^{7b}$,

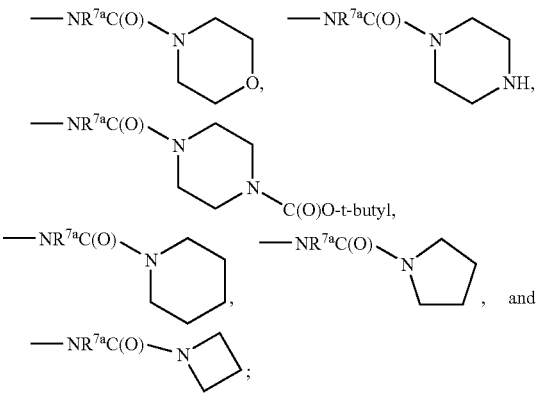

$R^{7a}$, at each occurrence, is independently selected from H and $C_{1-4}$ alkyl;

alternatively, two $R^{7a}$s, together with the N to which they are attached, join to form a heterocycle wherein the heterocycle is selected from azetidinyl, pyrrolyl, piperidinyl, and morpholinyl;

$R^{7b}$, at each occurrence, is selected from $C_{1-6}$ alkyl, a $(CH_2)_rC_{3-6}$ carbocyclic residue substituted with 0-3 $R^{7e}$, and a $(CH_2)_r$-5-6 membered heterocyclic system containing 1-4 heteroatoms selected from N, O, and S, substituted with 0-2 $R^{7e}$;

$R^{7d}$, at each occurrence, is selected from $C_{1-6}$ alkyl, a $(CH_2)_r$—$C_{3-6}$ carbocyclic residue substituted with 0-3 $R^{7e}$, and a $(CH_2)_r$-5-6 membered heterocyclic system containing 1-4 heteroatoms selected from N, O, and S, substituted with 0-2 $R^{7e}$;

$R^{7e}$, at each occurrence, is selected from $C_{1-6}$ alkyl, Cl, F, Br, CN, $(CF_2)_rCF_3$, $(CH_2)_rOC_{1-4}$ alkyl, $C(O)OC_{1-4}$ alkyl, $(CH_2)_rNR^{7f}R^{7f}$, and acetyl;

$R^{7f}$, at each occurrence, is selected from H, and $C_{1-4}$ alkyl;

$R^8$ is H;

$R^{10}$ and $R^{10a}$ are independently selected from H and $C_{1-4}$ alkyl;

$R^{12}$ is H;

$R^{14}$, at each occurrence, is H;

a is 1;

b is 0;

c is 1;

d is 1;

n is 1;

p, at each occurrence, is independently selected from 0, 1, and 2; and r, at each occurrence, is independently selected from 0 and 1.

6. A compound of claim 1, wherein the compound is selected from

N-[(octahydrocyclopenta[c]—pyrrol-5-ylcarbamoyl)methyl]-3 -trifluoromethylbenzamide trifluoroacetic acid salt;

endo-N-[(2-isopropyloctahydrocyclo-penta[c]pyrrol-5-ylcarbamoyl)methyl]-3- trifluoromethyl-benzamide trifluoroacetic acid salt;

4-endo-N-[(2-isopropyl-4-propyloctahydrocyclopenta[c]pyrrol-5-ylcarbamoyl)methyl]-3-trifluoromethylbenzamide trifluoroacetic acid salt;

morpholine-4-carboxylic acid 4-endo-5-endo-(2-{[(2-isopropyl-4-propyloctahydrocyclo-penta[c]pyrrol-5-ylcarbamoyl)methyl]carbamoyl}-4-trifluoromethylphenyl)amide trifluoroacetic acid salt;

N-[(endo-2-isopropyl-octahydrocyclopenta[c]pyrrol-4-ylcarbamoyl)methyl]-3- trifluoromethylbenzamide;

N-[(2-isopropyl-4-methoxymethyloctahydrocyclopenta[c]pyrrol-5-ylcarbamoyl)-methyl]-3-trifluoromethyl-benzamide;

N-{[2-isopropyl-4-(propane-2-sulfonylmethyl)octahydrocyclopenta[c]pyrrol-5-yl-carbamoyl]methyl}-3-trifluoromethylbenzamide;

N-[(4-benzenesulfonylmethyl-2-isopropyloctahydrocyclopenta[c]pyrrol-5-ylcarbamoyl)-methyl]-3 -trifluoromethylbenzamide; or N-(2-isopropyl-4-methoxymethyloctahydrocyclopenta[c]pyrrol-5-yl)-2-(6- trifluoromethylquinazolin-4-ylamino)acetamide.

7. A pharmaceutical composition comprised of a pharmaceutically acceptable carrier and a therapeutically effective amount of a compound of Formula (I)

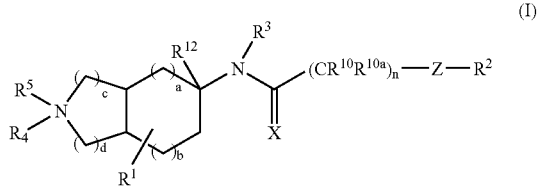

(I)

or stereoisomers or pharmaceutically acceptable salts thereof, wherein

X is O;

Z is selected from a bond, —C(O)—, —C(O)NR$^8$—, —NR$^8$—, —NR$^8$—CR$^{14}$R$^{14}$—, —NR$^8$C(O)—, —NR$^8$C(O)NH—, —NR$^8$C(S)NH—, —NR$^8$SO$_2$—, —NR$^8$SO$_2$NH—, —OC(O)NR$^8$—, —NR$^8$C(O)O—, —(CR$^{25}$R$^{25}$)$_u$—, —CR$^{14}$=CR$^{14}$—, —CR$^{25}$R$^{25}$C (O)—, —C(O)CR$^{25}$R$^{25}$—, —CR$^{25}$R$^{25}$C(=N—OR$^{14}$)—, —O—CR$^{14}$R$^{14}$—, —CR$^{14}$R$^{14}$—O—, —O—, —CHR$^{14}$—NR$^{8}$—, —S(O)$_p$—, —S(O)$_p$—CR$^{14}$R$^{14}$—, and —S(O)$_p$—NR$^{8}$—;

R$^1$ is selected from H, R$^6$, C$_{1-6}$ alkyl substituted with 0-3 R$^6$, C$_{2-6}$ alkenyl substituted with 0-3 R$^6$, C$_{2-6}$ alkynyl substituted with 0-3 R$^6$, C$_{6-10}$ aryl group substituted with 0-5 R$^6$, and a 5-10 membered heteroaryl system containing 1-4 heteroatoms selected from N, O, and S, substituted with 0-3 R$^6$;

R$^2$ is selected from a C$_{6-10}$ aryl group substituted with 0-5 R$^7$ and a 5-10 membered heteroaryl system containing 1-4 heteroatoms selected from N, O, and S, substituted with 0-3 R$^7$;

R$^3$ is selected from H, methyl, and ethyl;

R$^4$ is absent, taken with the nitrogen to which it is attached to form an N-oxide, or selected from C$_{1-8}$ alkyl, C$_{2-8}$ alkenyl, C$_{2-8}$ alkynyl, (CR'R')$_r$C$_{3-6}$ cycloalkyl, (CR'R')$_q$C(O)R$^{4b}$, (CR'R')$_q$C(O)NR$^{4a}$R$^{4a}$, (CR'R')$_q$C(O)OR$^{4b}$, and a (CR'R')$_r$—C$_{3-10}$ carbocyclic residue substituted with 0-3 R$^{4c}$;

R$^{4a}$, at each occurrence, is independently selected from H, C$_{1-6}$ alkyl, (CR'R')$_r$C$_{3-6}$ cycloalkyl, and phenyl;

alternatively, two R$^{4a}$s, together with the N to which they are attached, join to form a 3-8 membered heterocycle containing 0-1 additional heteroatoms selected from N, O and S;

R$^{4b}$, at each occurrence, is independently selected from C$_{1-6}$ alkyl, C$_{2-8}$ alkenyl, (CR'R')$_r$C$_{3-6}$ cycloalkyl, C$_{2-8}$ alkynyl, and phenyl;

R$^{4c}$, at each occurrence, is independently selected from C$_{1-6}$ alkyl, C$_{2-8}$ alkenyl, C$_{2-8}$ alkynyl, C$_{3-6}$ cycloalkyl, Cl, F, Br, I, CN, NO$_2$, (CF$_2$)$_r$CF$_3$, (CR'R')$_r$OC$_{1-5}$ alkyl, (CR'R')$_r$OH, (CR'R')$_r$SC$_{1-5}$ alkyl, (CR'R')$_r$NR$^{4a}$R$^{4a}$, and (CR'R')$_r$phenyl;

R$^5$ is selected from H, C$_{1-6}$ alkyl substituted with 0-2 R$^{5e}$, —C(O)R$^{5b}$, —C(O)OR$^{5b}$, —C(O)NR$^{5f}$R$^{5f}$, a C$_{3-10}$ carbocyclic residue substituted with 0-5 R$^{5e}$, and a 5-10 membered heterocyclic system containing 1-4 heteroatoms selected from N, O, and S, substituted with 0-3 R$^{5e}$;

R$^{5b}$, at each occurrence, is selected from C$_{1-6}$ alkyl substituted with 0-3 R$^{5e}$, C$_{3-8}$ alkenyl substituted with 0-2 R$^{5e}$, C$_{3-8}$ alkynyl substituted with 0-2 R$^{5e}$, a (CR'R')—C$_{3-6}$ carbocyclic residue substituted with 0-2 R$^{5e}$, and a (CR'R')$_r$-5-6 membered heterocyclic system containing 1-4 heteroatoms selected from N, O, and S, substituted with 0-3 R$^{5e}$;

R$^{5e}$, at each occurrence, is selected from C$_{1-6}$ alkyl, C$_{2-8}$ alkenyl, C$_{2-8}$ alkynyl, C$_{3-6}$ cycloalkyl, Cl, F, Br, I, CN, NO$_2$, (CF$_2$)$_r$CF$_3$, (CR'R')$_r$OC$_{1-5}$ alkyl, OH, SH, (CR'R')$_r$ SC$_{1-5}$ alkyl, (CR'R')$_r$NR$^{5f}$R$^{5f}$, a (CR'R')$_r$C$_{3-6}$ carbocyclic residue substituted with 0-3 R$^{6e}$, and a (CR'R')$_r$-5-6 membered heterocyclic system containing 1-4 heteroatoms selected from N, O, and S, substituted with 0-2 R$^{6e}$;

R$^{5f}$, at each occurrence, is selected from H, C$_{1-6}$ alkyl, and C$_{3-6}$ cycloalkyl;

alternatively, two R$^{5f}$s, together with the N to which they are attached, join to form a 3-8 membered heterocycle containing 0-1 additional heteroatoms selected from N, O and S;

R$^6$, at each occurrence, is selected from C$_{1-8}$ alkyl, C$_{2-8}$ alkenyl, C$_{2-8}$ alkynyl, (CR'R')$_r$C$_{3-6}$ cycloalkyl, Cl, Br, I, F, NO$_2$, CN, (CR'R')$_r$NR$^{6a}$R$^{6a}$, (CR'R')$_r$OH, (CR'R')$_r$O (CR'R')$_r$R$^{6d}$, (CR'R')$_r$SH, (CR'R')$_r$C(O)H, (CR'R')$_r$S (CR'R')$_r$R$^{6d}$, (CR'R')$_r$SC(O)(CR'R')$_r$R$^{6a}$, (CR'R')$_r$C(O) OH, (CR'R')$_r$C(O)(CR'R')$_r$R$^{6a}$, (CR'R')$_r$C(O)NR$^{6a}$R$^{6a}$, (CR'R')$_r$NR$^{6f}$C(O)(CR'R')$_r$R$^{6a}$, (CR'R')$_r$C(O)O (CR'R')$_r$ R$^{6d}$, (CR'R')$_r$OC(O)(CR'R')$_r$R$^{6a}$, (CR'R')$_r$OC (O)NR$^{6a}$(CR'R')$_r$R$^{6d}$, (CR'R')$_r$NR$^{6a}$C(O)NR$^{6a}$(CR'R')$_r$ R$^{6d}$, (CR'R')$_r$NR$^{6a}$C(S)NR$^{6a}$(CR'R')$_r$ R$^{6d}$, (CR'R')$_r$NR$^{6f}$C(O)O(CR'R')$_r$R$^{6a}$, (CR'R')$_r$C(=NR$^{6f}$)NR$^{6a}$R$^{6a}$, (CR'R')$_r$NHC(=NR$^{6f}$)NR$^{6f}$R$^{6f}$, (CR'R')$_r$S(O)$_p$(CR'R')$_r$ R$^{6a}$, (CR'R')$_r$S(O)$_2$NR$^{6a}$R$^{6a}$, (CR'R')$_r$NR$^{6f}$S(O)$_2$ NR$^{6a}$R$^{6a}$, (CR'R')$_r$NR$^{6f}$S(O)$_2$(CR'R')$_r$R$^{6a}$, C$_{1-6}$ haloalkyl, C$_{2-8}$ alkenyl substituted with 0-3 R', C$_{2-8}$ alkynyl substituted with 0-3 R', (CR'R')$_r$phenyl substituted with 0-3 R$^{6e}$, and a (CR'R')$_r$-5-6 membered heterocyclic system containing 1-2 heteroatoms selected from N, O, and S, substituted with 0-2 R$^{6e}$;

alternatively, two R$^6$s on adjacent atoms on R$^1$ may join to form a cyclic acetal;

R$^{6a}$, at each occurrence, is selected from H, methyl, C$_{2-6}$ alkyl substituted with 0-2 R$^{6e}$, C$_{3-8}$ alkenyl substituted with 0-2 R$^{6e}$, C$_{3-8}$ alkynyl substituted with 0-2 R$^{6e}$, a (CR'R')—C$_{3-10}$ carbocyclic residue substituted with 0-5 R$^{6e}$, and a (CR'R')$_r$-5-10 membered heterocyclic system containing 1-4 heteroatoms selected from N, O, and S, substituted with 0-2 R$^{6e}$;

alternatively, two R$^{6a}$s, together with the N to which they are attached, join to form a 3-8 membered heterocycle containing 0-1 additional heteroatoms selected from N, O, and S;

R$^{6d}$, at each occurrence, is selected from C$_{3-8}$ alkenyl substituted with 0-2 R$^{6e}$, C$_{3-8}$ alkynyl substituted with 0-2 R$^{6e}$, methyl, CF$_3$, C$_{2-6}$ alkyl substituted with 0-3 R$^{6e}$, C$_{2-4}$ haloalkyl, a (CR'R')$_r$—C$_{3-10}$ carbocyclic residue substituted with 0-3 R$^{6e}$, and a (CR'R')$_r$-5-6 membered heterocyclic system containing 1-4 heteroatoms selected from N, O, and S, substituted with 0-3 R$^{6e}$;

R$^{6e}$, at each occurrence, is selected from C$_{1-6}$ alkyl, C$_{2-8}$ alkenyl, C$_{2-8}$ alkynyl, (CR'R')$_r$C$_{3-6}$ cycloalkyl, Cl, F, Br, I, CN, NO$_2$, (CF$_2$)$_r$CF$_3$, (CR'R')$_r$OC$_{1-5}$ alkyl, OH, SH, (CR'R')$_r$SC$_{1-5}$ alkyl, (CR'R')$_r$NR$^{6f}$R$^{6f}$, and (CR'R')$_r$ phenyl;

R$^{6f}$, at each occurrence, is selected from H, C$_{1-5}$ alkyl, and C$_{3-6}$ cycloalkyl, and phenyl;

alternatively, two R$^{6f}$s, together with the N to which they are attached, join to form a 3-8 membered heterocycle containing 0-1 additional heteroatoms selected from N, O and S;

R$^7$, at each occurrence, is selected from C$_{1-8}$ alkyl, C$_{2-8}$ alkenyl, C$_{2-8}$ alkynyl, (CR'R')$_r$C$_{3-6}$ cycloalkyl, Cl, Br, I, F, NO$_2$, CN, (CR'R')$_r$NR$^{7a}$R$^{7a}$, (CR'R')$_r$OH, (CR'R')$_r$O (CR'R')$_r$R$^{7d}$, (CR'R')$_r$SH, (CR'R')$_r$C(O)H, (CR'R')$_r$S (CR'R')$_r$R$^{7d}$, (CR'R')$_r$C(O)OH, (CR'R')$_r$C(O)(CR'R')$_r$ R$^{7b}$, (CR'R')$_r$C(O)NR$^{7a}$R$^{7a}$, (CR'R')$_r$NR$^{7f}$C(O) (CR'R')$_r$ R$^{7b}$, (CR'R')$_r$C(O)O(CR'R')$_r$R'7d, (CR'R')$_r$OC (O)(CR'R')$_r$R$^{7b}$, (CR'R')$_r$OC(O)NR$^{7a}$(CR'R')$_r$R$^{7a}$, (CR'R')$_r$ NR$^{7a}$C(O)NR$^{7a}$(CR'R')$_r$R$^{7a}$, (CR'R')$_r$NR$^{7f}$C (O)O(CR'R')$_r$R$^{7d}$, (CR'R')$_r$C(=NR$^{7f}$)NR$^{7a}$R$^{7a}$, (CR'R')$_r$ NHC(=NR$^{7f}$)NR$^{7f}$R$^{7f}$, (CR'R')$_r$S(O)$_p$ (CR'R')$_r$ R$^{7b}$, (CR'R')$_r$S(O)$_2$NR$^{7a}$R$^{7a}$, (CR'R')$_r$NR$^{7a}$S (O)$_2$ NR$^{7a}$R$^{7a}$, (CR'R')$_r$NR$^{7f}$S(O)$_2$(CR'R')$_r$R$^{7b}$, C$_{1-6}$ haloalkyl, C$_{2-8}$ alkenyl substituted with 0-3 R', C$_{2-8}$ alkynyl substituted with 0-3 R', a (CR'R')$_r$—C$_{3-10}$ carbocyclic residue substituted with 0-3 R$^{7e}$, and a (CR'R')$_r$-5-10 membered heterocyclic system containing 1-4 heteroatoms selected from N, O, and S, substituted with 0-3 R$^{7e}$;

alternatively, two R$^7$s on adjacent atoms on R$^2$ may join to form a cyclic acetal;

$R^{7a}$, at each occurrence, is independently selected from H, methyl substituted with 0-1 $R^{7g}$, $C_{2-6}$ alkyl substituted with 0-2 $R^{7e}$, $C_{3-8}$ alkenyl substituted with 0-2 $R^{7e}$, $C_{3-8}$ alkynyl substituted with 0-2 $R^{7e}$, a $(CR'R')_r$—$C_{3-10}$ carbocyclic residue substituted with 0-5 $R^{7e}$, and a $(CR'R')_r$-5-10 membered heterocyclic system containing 1-4 heteroatoms selected from N, O, and S, substituted with 0-2 $R^{7e}$;

alternatively, two $R^{7a}$s, together with the N to which they are attached, join to form a 3-8 membered heterocycle containing 0-1 additional heteroatoms selected from N, O and S;

$R^{7b}$, at each occurrence, is selected from $C_{1-6}$ alkyl substituted with 0-2 $R^{7e}$, $C_{3-8}$ alkenyl substituted with 0-2 $R^{7e}$, $C_{3-8}$ alkynyl substituted with 0-2 $R^{7e}$, a $(CR'R')_r C_{3-6}$ carbocyclic residue substituted with 0-3 $R^{7e}$, and a $(CR'R')_r$-4-6 membered heterocyclic system containing 1-4 heteroatoms selected from N, O, and S, substituted with 0-2 $R^{7e}$;

$R^{7d}$, at each occurrence, is selected from $C_{3-8}$ alkenyl substituted with 0-2 $R^{7e}$, $C_{3-8}$ alkynyl substituted with 0-2 $R^{7e}$, methyl, $CF_3$, $C_{24}$ haloalkyl, $C_{2-6}$ alkyl substituted with 0-3 $R^{7e}$, a $(CR'R')_r$—$C_{3-10}$ carbocyclic residue substituted with 0-3 $R^{7e}$, and a $(CR'R')_r$-5-6 membered heterocyclic system containing 1-4 heteroatoms selected from N, O, and S, substituted with 0-3 $R^{7e}$;

$R^{7e}$, at each occurrence, is selected from $C_{1-6}$ alkyl, $C_{2-8}$ alkenyl, $(CR'R')_r$cyclopropyl, Cl, F, Br, CN, $(CF_2)_r CF_3$, $(CR'R')_r OC_{1-5}$ alkyl, OH, $C(O)OC_{1-5}$ alkyl, $(CR'R')_r NR^{7f}R^{7f}$, and acetyl;

$R^{7f}$, at each occurrence, is selected from H, $C_{1-5}$ alkyl, and $C_{3-6}$ cycloalkyl, and phenyl;

alternatively, two $R^{7f}$s, together with the N to which they are attached, join to form a 3-8 membered heterocycle containing 0-1 additional heteroatoms selected from N, O and S;

$R^{7g}$ is independently selected from —$C(O)R^{7b}$, —$C(O)OR^{7d}$, —$C(O)NR^{7f}R^{7f}$, and $(CR'R')_r$phenyl;

R', at each occurrence, is independently, selected from H, methyl, and $C_{2-6}$ alkyl;

alternatively, two R's, along with the carbon atom to which they are attached, join to form a cyclopropyl ring;

$R^8$ is selected from H, $C_{1-4}$ alkyl, and $C_{3-4}$ cycloalkyl;

$R^{10}$ and $R^{10a}$ are independently selected from H and $C_{1-4}$ alkyl substituted with 0-1 $R^{10b}$, $R^{10b}$, at each occurrence, is independently selected from —OH, —SH, —$NR^{10c}R^{10c}$, —$C(O)NR^{10c}R^{10c}$, and —$NHC(O)R^{10c}$;

$R^{10c}$ is selected from H, $C_{1-4}$ alkyl and $C_{3-6}$ cycloalkyl;

alternatively, two $R^{10c}$s, together with the N to which they are attached, join to form a 3-8 membered heterocycle containing 0-1 additional heteroatoms selected from N, O and S;

$R^{12}$ is selected from H and $C_{1-4}$ alkyl;

$R^{14}$ at each occurrence, is independently selected from H and $C_{1-4}$alkyl;

alternatively, two $R^{14}$s, along with the carbon atom to which they are attached, join to form a $C_{3-6}$ carbocyclic ring;

$R^{25}$, at each occurrence, is independently selected from H, $C_{1-4}$alkyl, OH, $NH_2$, —O—$C_{1-4}$ alkyl, $NR^{25a}R^{25a}$, $C(O)NR^{25a}R^{25a}$, $NR^{25a}C(O)R^{25b}$, $NR^{25a}C(O)OR^{25b}$, $OC(O)NR^{25a}R^{25a}$, and $(CHR)_rC(O)OR^{25b}$;

alternatively, two $R^{25}$s, along with the carbon atom or atoms to which they are attached, join to form a $C_{3-6}$ carbocyclic ring;

$R^{25a}$, at each occurrence, is independently selected from H, and $C_{1-4}$ alkyl;

alternatively, two $R^{25a}$s, together with the N to which they are attached, join to form a 3-8 membered heterocycle containing 0-1 additional heteroatoms selected from N, O and S;

$R^{25b}$, at each occurrence, is independently selected from H, $C_{1-4}$ alkyl, $C_{3-6}$ alkenyl, and $C_{3-6}$ alkynyl;

a is selected from 0 and 1;

b is selected from 0, 1, 2 and 3;

with the proviso that a+b is selected from 1, 2 and 3;

c is 1;

d is 1;

with the proviso that c+d is 2;

n is selected from 1 and 2;

p, at each occurrence, is independently selected from 0, 1, and 2;

q, at each occurrence, is independently selected from 1, 2, 3, and 4;

r, at each occurrence, is independently selected from 0, 1, 2, 3, and 4; and u is selected from 1, 2 and 3.

\* \* \* \* \*

UNITED STATES PATENT AND TRADEMARK OFFICE
CERTIFICATE OF CORRECTION

PATENT NO. : 7,381,738 B2
APPLICATION NO. : 11/060250
DATED : June 3, 2008
INVENTOR(S) : Douglas G. Batt et al.

It is certified that error appears in the above-identified patent and that said Letters Patent is hereby corrected as shown below:

Title Page, Column 1, Foreign Patent Documents
Line 9, "WO WO 02/50019 A2 6/2000" should read -- WO WO 02/50019 A2 6/2002 --.

Title Page, Column 2, Other Publications
Line 6, ""Indentification" should read -- "Identification --.

Title Page, Column 2, Attorney
Line 1, "Terrance J. Bogie" should read -- Terence J. Bogie --.

Column 1
Line 4, Please insert the following heading under the title of the invention:
-- CROSS-REFERENCE TO RELATED APPLICATION --.

Column 52
Line 49, "$C_3$-8 alkynyl" should read -- $C_{3-8}$ alkynyl --.

Column 54
Line 56, "$R^{10c}S$," should read -- $R^{10c}s$, --.

Column 57
Line 65, "isoquinolinyl" should read -- isoquinolinyl, --.

Column 59
Lines 27-28, "isoquinolinyl" should read -- isoquinolinyl, --.

Column 60
Line 34, "R7f," should read -- $R^{7f}$, --;
Line 53, "—C(O)NR$^8$-" should read -- —C(O)NR$^8$— --;
Line 65, "isoquinolinyl" should read -- isoquinolinyl, --.

Column 61
Line 63, "1-4heteroatoms" should read -- 1-4 heteroatoms --.

Signed and Sealed this

Ninth Day of November, 2010

David J. Kappos
*Director of the United States Patent and Trademark Office*

CERTIFICATE OF CORRECTION (continued)
U.S. Pat. No. 7,381,738 B2

Column 62
Line 1, "R7f," should read -- $R^{7f}$, --;
Line 29, "propyloctahydrocyclo-penta[c]" should read -- propyloctahydrocyclopenta[c] --;
Line 38, "pyrrol-- 5-yl-carbamoyl]" should read -- pyrrol-- 5-ylcarbamoyl] --.

Column 63
Line 34, "$(CR'R')_rSC_{1-5}$ alkyl," should read -- $(CR'R')_rSC_{1-5}$ alkyl, --.

Column 64
Line 53, "$(CR'R')_rC(O)O(CR'R')_rR'7d$," should read -- $(CR'R')_rC(O)O(CR'R')_rR^{7d}$, --.

Column 65
Line 22, "$C_{24}$ haloalkyl," should read -- $C_{2-4}$ haloalkyl, --.